(12) United States Patent  (10) Patent No.: US 6,890,940 B2
Ishiwata et al.  (45) Date of Patent: May 10, 2005

(54) BIS(2-ARYL-5-PYRIDYL) DERIVATIVES

(75) Inventors: Hiroyuki Ishiwata, Ichikawa (JP); Seiichi Sato, Tokyo (JP); Mototsugu Kabeya, Higashimurayama (JP); Soichi Oda, Higashimurayama (JP); Makoto Suda, Higashimurayama (JP); Manabu Shibasaki, Chiba (JP)

(73) Assignee: Kowa Co., Ltd., Nagoya (JP)

( * ) Notice: Subject to any disclaimer, the term of this patent is extended or adjusted under 35 U.S.C. 154(b) by 164 days.

(21) Appl. No.: 09/893,680

(22) Filed: Jun. 29, 2001

(65) Prior Publication Data

US 2003/0022886 A1 Jan. 30, 2003

(51) Int. Cl.[7] .................. A61K 31/44; A61P 37/00; C07D 213/00
(52) U.S. Cl. .................. 514/332; 546/264
(58) Field of Search .................. 514/332; 546/264

(56) References Cited

FOREIGN PATENT DOCUMENTS

| EP | 0 787 491 | 8/1997 |
|---|---|---|
| JP | 59-167564 | 9/1984 |
| JP | 1-106818 | 4/1989 |
| JP | 7-017506 | 3/1995 |
| JP | 8-092216 | 4/1996 |
| JP | 8-109177 | 4/1996 |
| JP | 10-324631 | 12/1998 |
| JP | 11-269192 | 10/1999 |
| WO | WO 96/11682 | 4/1996 |
| WO | WO 98/04508 | 2/1998 |
| WO | WO 98/07702 | 2/1998 |
| WO | WO 98/16497 | 4/1998 |
| WO | WO 99/19291 | 4/1999 |
| WO | WO 99/35140 | 7/1999 |
| WO | WO 99/38829 | 8/1999 |
| WO | WO 99/42446 | 8/1999 |
| WO | WO 00/05198 | 2/2000 |

OTHER PUBLICATIONS

Robert B. Fick, Jr., Current Opinion in Pulmonary Medicine, vol. 5, pp. 76–80, "Anti–IgE as Novel Therapy for the Treatment of Asthma", 1999.
Farhad Imani, Emerging Therapeutic Targets, vol. 3, No. 2, pp. 229–240, "Emerging Therapeutic Targets in Asthma and Allergy: Modulation of IgE", 1999.
Naosuke Matsuura, et al., Jpn. Pahrmacol. Ther., vol. 22, No. 3, pp. 1369–1383, "An Immunopharmacological Study of (±) —[2- [- (3–Ethoxy–2–Hydroxypropoxy) Phenylcarbamoyl] Ethyl] Dimethylsulfonium p–Toluenesulfonate (Suplatast Tosilate, IPD–1151T)", 1994.
Henry Milgrom, et al., The New England Journal of Medicine, vol. 341, No. 26, pp. 1966–1973, "Treatment of Allergic Asthma with Monoclonal Anti–IgE Antibody", Dec. 23, 1999.

*Primary Examiner*—Brenda Coleman
(74) *Attorney, Agent, or Firm*—Oblon, Spivak, McClelland, Maier & Neustadt, P.C.

(57) ABSTRACT

A bis(2-aryl-5-pyridyl) compound having formula (1) or a salt thereof:

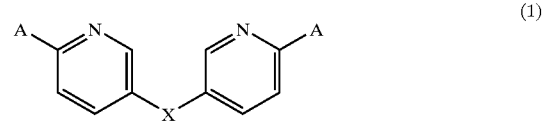

(1)

wherein A is a substituted or unsubstituted aromatic hydrocarbon group, and X is a substituent having one of the following formulas (2) to (4):

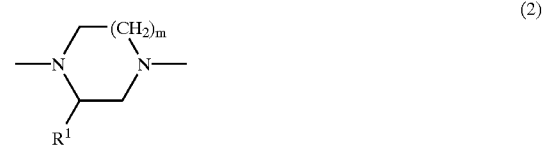

(2)

(3)

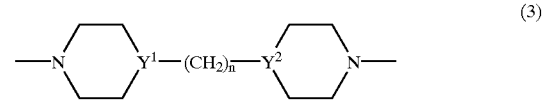

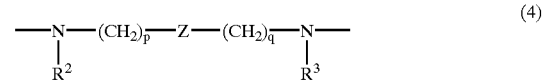

(4)

wherein, in formula (2), $R^1$ is a hydrogen atom or a di(lower alkyl)amino(lower alkyl) group, and m is an integer of 1 or 2; in formula (3), $Y^1$ and $Y^2$ each is a nitrogen atom or a CH group, and n is 0 or an integer of 1 to 6; in formula (4), $R^2$ and $R^3$ each is a hydrogen atom or a lower alkyl group, Z represents a single bond, a substituted methylene group, a substituted imino group, an oxygen atom or a cycloalkylene group, and p and q each is 0 or an integer of 1 to 6.

19 Claims, No Drawings

BIS(2-ARYL-5-PYRIDYL) DERIVATIVES

BACKGROUND OF THE INVENTION

1. Field of the Invention

The present invention relates to bis(2-aryl-5-pyridyl) derivatives or salts thereof, and to medicinal materials which comprise the bis(2-aryl-5-pyridyl) derivatives or salts thereof as active ingredients and are useful for the prevention or treatment of allergic immune diseases.

2. Discussion of the Background

IgE, a class of immunoglobulin (Ig), is an allergen-specific molecule produced by IgE producing cells differentiated from B cells, when triggered by contact of immunocytes with an allergen in the body.

IgE is produced in a target organ exhibiting an allergic response, and binds to a receptor on the surfaces of mast cells, which are principal effector cells, in an allergic reaction or basophils (sensitized state). Allergic chemical mediators such as histamine, leucotrienes, prostaglandins, and PAF, and tissue destructive enzymes such as tryptase are released from the mast cells, which are stimulated as a result of intrusion of the allergen into the body after sensitization and its reaction with specific IgE, to provoke immediate responses of an allergic reaction such as increased vasopermeability, smooth muscle constriction and vasodilation. Cytokines, such as IL-4, which activate other immune system cells, are also secreted from the stimulated mast cells. As a result, eosinophils, basophils or the like infiltrate tissues, and an allergic chemical mediator or tissue destructive protein such as MBP, which are secreted by these inflammatory cells, induce late responses of the allergic reaction and protract and worsen an allergic symptom.

As can be appreciated from what is stated above, abnormality in IgE production is highly relevant to various allergic immune diseases such as asthma, atopic dermatitis, allergic rhinitis, inflammatory bowel disease, contact dermatitis and allergic ophthalmopathy. It is known that inhibition of IgE production makes it possible to prevent and/or treat these diseases (Emerging Therapeutic Targets In Asthma And Allergy: Modulation Of IgE. *Emerging Therapeutic Targets*, 3, 229–240 (1990); Anti-IgE As Novel Therapy For The Treatment Of Asthma. *Curr. Opin. Plum. Med.*, 5, 76–80 (1999); Treatment Of Allergic Asthma With Monoclonal Anti-IgE Antibody., *N. Eng. J. Med.*, 341, 1966–1973 (1999); Anti-IgE Antibody Therapy For Asthma. *N. Eng. J. Med.*, 341, 2006–2008 (1999).).

From the foregoing, IgE is believed to be a substance which is involved in the manifestation of an allergic disease from the very beginning. With the objective of developing antiallergic agents, some small molecules with IgE antibody production inhibiting activity have been found and have been reported to date (WO 98/04058, WO 98/07702, WO 98/16497, JP 10-324631A, WO 99/19291, WO 99/35140, WO 99/38829, WO 99/42446, JP 11-269192A, WO 00/05198, "Yakuri to Chiryo (Basic Pharmacology & Therapeutic)", 22(3), 1369 (1994), JP 1-106818A, JP 7-17506B, JP 8-92216A, JP 8-109177A, WO 96/11682, JP 59-167564A). These compounds, however, involve problems such as low solubility in water, and thus they are not fully satisfactory for the stated reason and other reasons.

SUMMARY OF THE INVENTION

Accordingly, one object of the present invention is to provide a compound having excellent IgE antibody production inhibiting activity and also a medicinal composition comprising the compound as an active ingredient.

Briefly, this object and other objects of the present invention as hereinafter will become more readily apparent can be attained by a bis(2-aryl-5-pyridyl) derivative having formula (1) or a salt thereof:

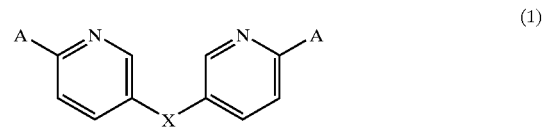

wherein A is a substituted or unsubstituted aromatic hydrocarbon group, and X is a group selected from one of the following formulas (2) to (4):

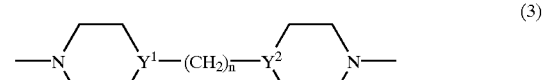

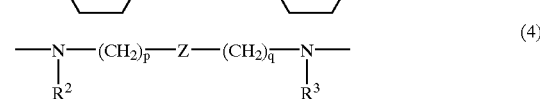

wherein in formula (2), $R^1$ is a hydrogen atom or a di(lower alkyl)amino(lower alkyl) group, and m is 1 or 2; in formula (3), $Y^1$ and $Y^2$ are each a nitrogen atom or a CH group, and n is 0 or an integer of 1 to 6; in formula (4), $R^2$ and $R^3$ each are a hydrogen atom or a lower alkyl group, Z is a single bond, a substituted methylene group, a substituted imino group, an oxygen atom or a cycloalkylene group, and p and q are each 0 or an integer of 1 to 6.

Another aspect of the invention is a medicinal composition comprising the bis(2-aryl-5-pyridyl) derivative or the salt thereof and a pharmacologically acceptable carrier.

Still another aspect of the invention is a method of treating a subject for an allergic immune disease by administering the bis(2-aryl-5-pyridyl) derivative or the salt thereof to a subject.

DESCRIPTION OF THE PREFERRED EMBODIMENTS

As a result of investigation, it has now been found that compounds represented by formula (1) have excellent IgE antibody production inhibiting activity and also good solubility in water and hence, are useful as medicines for the prevention or treatment of allergic immune diseases.

Illustrative of embodiments of lower alkyl in "lower alkyl groups", "lower alkoxy groups", "halogeno(lower alkoxy) groups", "lower alkoxy(lower alkoxy) groups", "hydroxy(lower alkoxy) groups", "(lower alkoxy)carbonyl groups", "lower alkanoyl groups", "lower alkanoyloxy groups", "(lower alkyl)- and/or (lower alkoxy)-substituted carbamoyl groups", "(lower alkyl)thio groups", "(lower alkyl)amino groups", "(lower alkyl)sulfonylamino groups" as used herein include linear, branched or cyclic alkyl groups having 1 to 6 carbon atoms. Suitable examples include methyl, ethyl, n-propyl, isopropyl, n-butyl, isobutyl, sec-butyl, tert-butyl, pentyl, hexyl, cyclopropyl, and cyclohexyl. Suitable examples of "halogen atoms" are fluorine, chlorine, bromine, and iodine.

In formula (1), the aromatic hydrocarbon group represented by A is preferably a group which has 6 to 14 carbon atoms, with a phenyl or naphthyl group being more preferred and a phenyl group being particularly preferred. These groups may contain 1 to 3 substituents. Suitable examples of such substituents include lower alkyl groups, lower alkoxy groups, halogeno(lower alkyl) groups, lower alkoxy(lower alkyl) groups, hydroxy(lower alkyl) groups, carboxyl group, (lower alkoxy)carbonyl groups, unsubstituted or lower alkyl- and/or (lower alkoxy)-substituted carbamoyl groups, lower lkanoyl groups, formyl group, lower alkanoyloxy groups, halogen atoms, hydroxyl group, yano, (lower alkyl)thio groups, amino group, mono- or di-(lower alkyl)amino groups, (lower alkyl)sulfonylamino groups, pyrrolidinyl groups, and alkylenedioxy groups.

Preferred specific examples of these substituents include methyl, methoxy, ethoxy, n-propoxy, isopropoxy, trifluoroethoxy, methoxyethoxy, hydroxyethoxy, hydroxy, cyano, methylthio, dimethylamino, pyrrolidinyl, carboxyl, ethoxycarbonyl, t-butoxycarbonyl, butyryloxy, N-methyl-N-methoxycarbamoyl, acetyl, and methylenedioxy.

Among the groups represented by X, the group of formula (2) contains the di(lower alkyl)amino(lower alkyl) group represented by $R^1$. As the di(lower alkyl)amino group in the di(lower alkyl)amino(lower alkyl) group, a dimethylamino group or the like is particularly preferred.

In formula (3), n preferably ranges from 2 to 4.

In formula (4), the substituted methylene group represented by Z contains one or two substituents, examples of which include lower alkyl, hydroxy, pyrrolidinyl and benzyloxy groups. The substituted imino group represented by Z contains one or two substituents, examples of which include lower alkyl groups. Illustrative of the cycloalkylene represented by Z are cyclopentylene, cyclohexylene, and cycloheptylene.

Further, p and q preferably range from 0 to 4.

Preferred specific examples of bis(2-aryl-5-pyridyl) derivative (1) of the present invention include N,N'-bis[2-(3,4,5-trimethoxyphenyl)-5-pyridyl]-N,N'-dimethylethylenediamine dimethanesulfonate, N,N'-bis[2-(4-hydroxy-3,5-dimethoxyphenyl)-5-pyridyl]-N,N'-dimethylethylenediamine dimethanesulfonate, 1,4-bis[2-(3,4,5-trimethoxyphenyl)-5-pyridyl]hexahydro-1,4-diazepine dimethanesulfonate, N,N'-bis[2-(3,4,5-trimethoxyphenyl)-5-pyridyl]-N,N'-diethylethylenediamine dimethanesulfonate, N,N'-bis[2-(3,4,5-trimethoxyphenyl)-5-pyridyl]-N,N'-dimethyl-1,3-propanediamine dimethanesulfonate, N,N'-bis[2-(3,4,5-trimethoxyphenyl)-5-pyridyl]-N,N',2,2-tetramethyl-1,3-propanediamine dimethanesulfonate, 2-hydroxy-N,N'-bis[2-(3,4,5-trimethoxyphenyl)-5-pyridyl]-N,N'-dimethyl-1,3-propanediamine, N,N-bis[N-[2-(3,4,5-trimethoxyphenyl)-5-pyridyl]-N-methyl-2-aminoethyl]methylamine trihydrochloride, N,N-bis[N-[2-(3,4,5-trimethoxyphenyl)-5-pyridyl]-N-methyl-3-aminopropyl]methylamine, bis[N-[2-(3,4,5-trimethoxyphenyl)-5-pyridyl]-2-aminoethyl]ether dimethanesulfonate, 2-dimethylaminomethyl-1,4-bis[2-(3,4,5-trimethoxyphenyl)-5-pyridyl]piperazine trihydrochloride, N,N'-bis[2-(3,4,5-trimethoxyphenyl)-5-pyridyl]-N,N'-dimethyl-1,6-hexanediamine dimethanesulfonate, N,N-bis[N-[2-[3,5-dimethoxy-4-(2,2,2-trifluoroethoxy)phenyl]-5-pyridyl]-N-methyl-3-aminopropyl]methylamine trihydrochloride.

Compound (1) of the present invention can be produced, for example, by the reaction steps of the below-described processes, although no particular limitation is imposed on the process of synthesis employed.

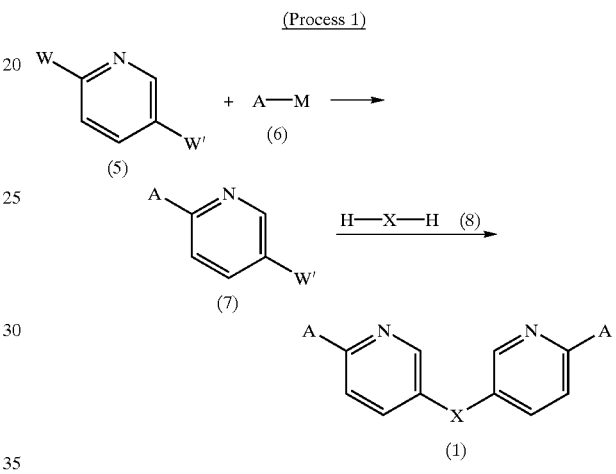

wherein A and X have the same meanings as defined above, W and W' represent halogen or $-OSO_2(C_rF_{2r+1})$ in which r is 0 or an integer of 1 to 4, and M represents dihydroxyboron, di(lower alkoxy)boron, di(lower alkyl)boron, dihalo(lower alkyl)silicon, halogenated zinc, tri(lower alkyl)tin, halogenated magnesium or the like.

Described specifically, compound (1) of the present invention can be prepared by adding compound (6) and a catalyst to a solution or suspension of compound (5), conducting the reaction optionally in the presence of a ligand and a base to prepare compound (7) and then treating compound (7) with compound (8).

1) Synthesis of the Compound (7) (Cross-Coupling Reaction)

Compound (7) can be obtained by adding compound (6), the catalyst and, if necessary, the ligand and the base to the solution or suspension of compound (5) and then conducting the reaction at room temperature to 200° C. for 0.5 to 10 hours (Metal-catalyzed Cross-coupling Reactions; Diederich, F., Stang, P. J., Eds.; Wiley-VHC: Weinheim (1998). Stanforth, S. P. *Tetrahedron*, 54, 263–303 (1998)).

Illustrative of a solvent usable in the above reaction include benzene, toluene, xylene, diethyl ether, tetrahydrofuran, dimethoxyethane, dioxane, acetonitrile, dimethylformamide, N-methylpiperidone, methanol, ethanol, and water. Examples of the catalyst include tetrakis(triphenylphosphine)palladium(0), tris(bisbenzylideneacetone)dipalladium(0), palladium(II) acetate, palladium(II) chloride, dichlorobis (triphenylphosphine)palladium(II), dichloro[1,2-bis (diphenylphosphino)ethane]palladium(II), dichloro[1,4-bis (diphenylphosphino)butane]palladium(II), dichloro[1,1'-bis (diphenylphosphino)ferrocene]palladium(II), tetrakis (triphenylphosphine)nickel(0) and bis(acetylacetonato) nickel (II).

Suitable examples of the ligand of the metal complexes include tri(t-butyl)phosphine, triphenylphosphine, tri(o-tolyl)phosphine, tri(2-furyl)phosphine, 2,2'-bis (diphenylphosphino)-1,1'-binaphthyl, 1,2-bis (diphenylphosphino)-ethane, 1,3-bis(diphenylphosphino) propane, 1,4-bis(diphenylphosphino)butane, and 1,1'-bis (diphenylphosphino)ferrocene. Suitable examples of a base include sodium acetate, potassium carbonate, sodium carbonate, sodium hydrogencarbonate, potassium phosphate, sodium hydroxide, potassium hydroxide, barium hydroxide, sodium methoxide, sodium ethoxide, cesium fluoride, tetrabutylammonium fluoride, and triethylamine.

The reaction can be conducted preferably by following the procedure disclosed by Stille et al (Stille, J. K., *Angew. Chem. Int. Ed. Engl.*, 25, 508–524 (1986).), the procedure disclosed by Suzuki et al (Miyaura, N.; Suzuki, A. *Chem. Rev.*, 95, 2457–2483 (1995)) or the procedure disclosed by Mitchell et al, (Mitchell, M. B.; Wallbank, P. J., *Tetrahedron Lett.*, 32, 2273–2276 (1991)). That is, compound (6) in which M is a tri(lower alkyl)tin can be used under conditions of tetrakis(triphenylphosphine)palladium(0)/toluene/100 to 150° C./10 to 30 hours. Also compound (6) in which M is a dihydroxyboron can be used under conditions of tetrakis (triphenylphosphine)palladium(0)/sodium carbonate (or potassium carbonate)/water-ethanol(or methanol)-toluene/ 60 to 110° C./0.5 to 3 hours. Still further, compound (6) in which M is a dihydroxyboron can be used under conditions of dichloro[1,2-bis(diphenylphosphino)ethane]palladium (II)[or dichloro[1,4-bis(diphenylphosphino)butane] palladium(II)]/sodium carbonate(or potassium carbonate)/ water-ethanol(or methanol)-toluene/80 to 120° C./1 to 24 hours.

2) Synthesis of the Compound (1) (Condensation)

Compound (1) may also be obtained by adding compound (8), a catalyst, a base and, if necessary, a ligand to a solution of compound (7) and then conducting the reaction at room temperature to 200° C. for 0.5 to 100 hours, preferably at 80 to 120° C. for 5 to 15 hours (Yang, B. H., Buchwald, S. L., *J. Organomet. Chem.*, 576, 125–146 (1999). Hartwig. J. F., *Angew. Chem. Int. Ed. Engl.*, 37, 2046–2067 (1998). Nishiyama, M., Yamamoto, T., Koike, Y., *Tetrahedron Lett.*, 39, 617–620 (1998)).

Suitable solvents for the reaction include toluene, xylene, dimethoxyethane, tetrahydrofuran, and dioxane. Suitable catalyst embodiments include tetrakis(triphenylphosphine) palladium(0), tris(bisbenzylideneacetone)dipalladium(0), palladium(II) acetate, and dichloro[1,1'-bis (diphenylphosphino)ferrocene]palladium(II), with tetrakis (triphenylphosphine)palladium(0) and tris (bisbenzylideneacetone)dipalladium(0) being particularly preferred. Suitable embodiments of the base include sodium t-butoxide, potassium t-butoxide, potassium phosphate, potassium carbonate, cesiumn carbonate, lithium tetramethyldisilazide, triethylamine, and 1,8-diazabicyclo[5, 4,0]-7-undecene(DBU), with sodium t-butoxide, potassium t-butoxide and potassium carbonate being particularly preferred. Suitable examples of the ligand include tri(t-butyl) phosphine, triphenylphosphine, tri(o-tolyl)phosphine, tri(2-furyl)phosphine, 2,2'-bis(diphenyl-phosphino)-1,1'-binaphthyl, 1,2-bis(diphenylphosphino)ethane, 1,3-bis (diphenylphosphino)propane, 1,4-bis(diphenylphosphino) butane, and 1,1'-bis(diphenyl-phosphino)ferrocene.

(Production Process 2)

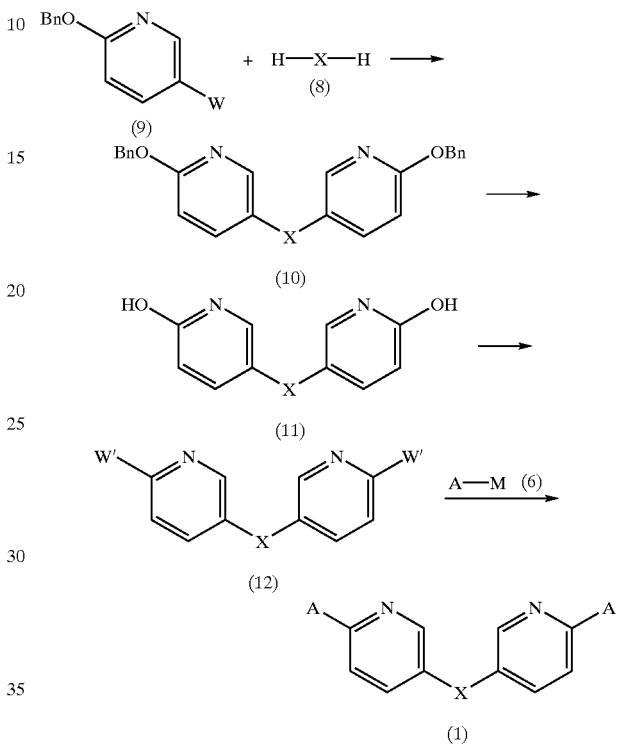

wherein A, X, W, W' and M have the same meanings as defined above.

More specifically, compound (1) can be prepared by subjecting compound (9) and compound (8) to a condensation reaction thereby preparing compound (10), removing the benzyl group of compound (10) to yield compound (11), modifying the hydroxyl groups of compound (11) to prepare compound (12), and then treating compound (12) with compound (6).

1) Synthesis of the Compound (10) (Condensation)

The compound (10) may be prepared by treating 2-benzyloxy-5-halopyridine (9) with compound (8) under similar conditions as in the reaction of compound (7) and compound (8) in Process 1 above.

2) Synthesis of the Compound (11) (Removal of the Benzyl Group)

Compound (11) may be prepared by adding an acid to a solution of compound (10) and then conducting the reaction at −20 to 100° C. for 0.5 to 100 hours, preferably at 30 to 60° C. for 1 to 6 hours.

Illustrative of suitable solvents include chloroform, methylene chloride, dichloroethane, and ethyl acetate. Suitable examples of the acid include hydrogen chloride and trifluoroacetic acid. It is also possible to use the acid as a solvent.

3) Synthesis of the Compound (12) (Conversion of the Hydroxyl Group into a Better Leaving Group)

Compound (12) can be prepared by adding a base and $ClSO_2(C_sF_{2s+1})$ or $[SO_2(C_sF_{2s+1})]_2O$ (being $[SO_2(CF_3)]_2O$ preferred)(s is 0 or an integer of 1 to 4) to a solution or suspension of compound (11) and stirring the resulting mixture at −78 to 100° C. for 5 minutes to 10 hours, preferably at −78 to 0° C. for 10 minutes to 2 hours.

Illustrative of suitable solvents include methylene chloride, chloroform, dichloroethane, benzene, toluene, xylene, diethyl ether, tetrahydrofuran, dimethoxyethane, dioxane, and acetonitrile. Suitable examples of the base include sodium acetate, potassium carbonate, sodium hydrogencarbonate, potassium phosphate, triethylamine, N,N-diisopropylethylamine, and pyridine, with triethylamine and N,N-diisopropylethylamine being preferred.

In an alternative process, compound (12) can be prepared by treating compound (11) with a halogenating reagent at room temperature to 200° for 0.5 minutes to 200 hours, preferably at 50 to 120° C. for 5 to 12 hours. A solvent can also be used as needed.

Suitable halogenating reagents include phosphorus pentachloride, phosphorus oxychloride, phosphorus tribromide, and phosphorus oxybromide, with phosphorus oxychloride-phosphorus pentachloride being particularly preferred. Suitable examples of the solvent include chloroform, methylene chloride and dichloroethane.

4) Synthesis of the Compound (1) (Cross-coupling Reaction)

Compound (1) can be prepared by treating compound (12) with compound (6) under similar conditions as in the cross-coupling of compound (5) with compound (6) in Process 1 above.

(Production Process 3)

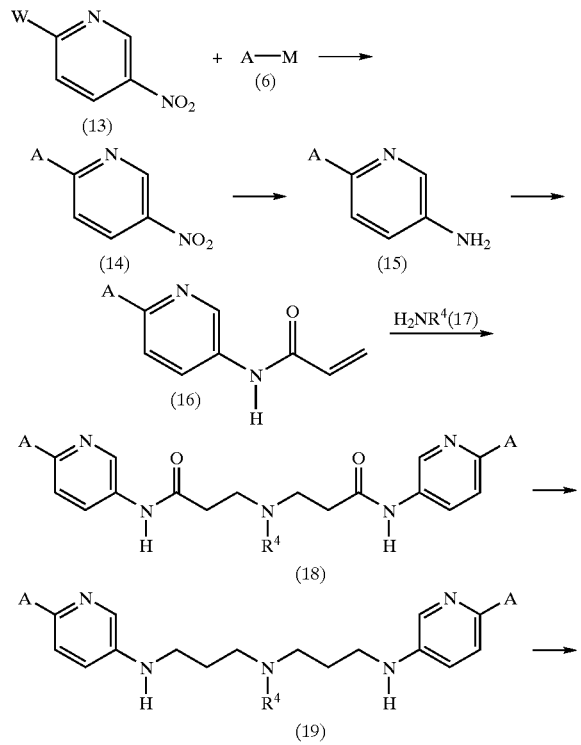

-continued

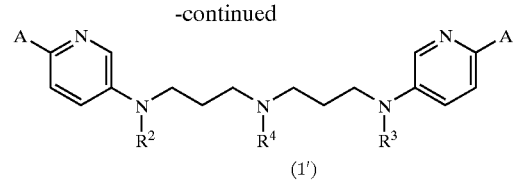

wherein A, W, M, $R^2$ and $R^3$ have the same meanings as defined above, and $R^4$ represents a lower alkyl group.

Among compounds (1), compounds (1') in which X is a group of formula (4), p and q are 3, and Z is a substituted imino group can be prepared by the reaction steps of the above-described Process 3.

1) Synthesis of Compound (14) (Cross-Coupling Reaction)

Compound (14) can be prepared by treating 2-halo-5-nitropyridine (13) with compound (6) under similar conditions as described in the cross-coupling reaction between compound (5) and compound (6) in Process 1 above.

2) Synthesis of Compound (15) (Reduction of the Nitro Group)

Compound (15) can be prepared by reducing compound (14) in a manner known per se in the art. As a specific reducing reaction, a catalyst and a hydrogen source are added to a solution of compound (14), followed by conducting the reaction at 0 to 100° C. for 5 minutes to 100 hours, preferably at 20 to 60° C. for 0.5 to 5 hours (Process A); or an acid and a metal or metal salt are added to a solution or suspension of compound (14), followed by conducting the reaction at room temperature to 100° C. for 5 minutes to 100 hours, preferably at 50 to 100° C. for 0.5 to 3 hours (Process B).

For Process A, suitable solvents include tetrahydrofuran, dimethoxyethane, dioxane, ethyl acetate, methanol, ethanol. Suitable examples of catalysts include palladium on charcoal, platinum black, platinum, and Raney nickel; and illustrative sources of hydrogen include hydrogen, ammonium formate, and hydrazine.

As representative of specific conditions for Process B, suitable solvents include ethanol and water. Suitable examples of acids include hydrochloric acid and acetic acid; and illustrative examples of metals or metal salts include zinc powder, tin powder, iron powder, and stannous chloride.

3) Synthesis of Compound (16) (Acylation)

Compound (16) can be prepared by adding a base and acryloyl chloride to a solution of compound (15) and treating them at −78 to 50° C. for 5 minutes to 100 hours, preferably at −30 to 30° C. for 10 minutes to 1 hour.

Suitable solvents include methylene chloride, chloroform, dichloroethane, benzene, toluene, xylene, diethyl ether, tetrahydrofuran, dimethoxyethane, dioxane, and acetonitrile, with methylene chloride and tetrahydrofuran being particularly preferred. Suitable bases include sodium acetate, potassium carbonate, sodium hydrogencarbonate, potassium phosphate, triethylamine, and N,N-diisopropylethylamine, with triethylamine and N,N-diisopropylethylamine being particularly preferred.

4) Synthesis of Compound (18) (Michael Addition)

Compound (18) can be prepared by treating compound (16) with amine (17) at 0 to 200° C. for 0.5 to 100 hours, preferably at 20 to 100° C. for 1 to 15 hours.

Here, a solvent may be used if necessary. Suitable solvents include methylene chloride, chloroform, dichloroethane, benzene, toluene, xylene, diethyl ether, tetrahydrofuran, dimethoxyethane, dioxane, acetonitrile, and dimethylformamide.

5) Synthesis of Compound (19) (Reduction)

Compound (19) can be prepared by adding a reducing agent to a solution of compound (18) and treating the prepared material at 0 to 100° C. for 5 minutes to 100 hours, preferably at 20 to 80° C. for 30 minutes to 3 hours.

Suitable solvents include toluene, diethyl ether, tetrahydrofuran, and dimethoxyethane. Suitable reducing agents include lithium aluminum hydride, diisobutylaluminum hydride, and borane.

6) Synthesis of Compound (1') (Alkylating Reaction)

Compound (1') can be prepared by adding a reducing agent and an acid to a solution of compound (19) and a carbonyl compound and conducting the reaction at −20 to 50° C. for 0.5 to 100 hours, preferably at 0 to 30° C. for 1 to 15 hours.

Suitable carbonyl compounds include formaldehyde, lower alkylaldehydes, and di(lower alkyl) ketone. Suitable solvents include methylene chloride, chloroform, tetrahydrofuran, dimethoxyethane, dioxane, acetonitrile, methanol, and ethanol. Suitable reducing agents include lithium aluminum hydride, sodium borohydride, sodium cyanoborohydride, and borane, Suitable acids include hydrochloric acid, acetic acid, and trifluoroacetic acid.

1) Synthesis of Compound (21) (Amide Formation)

Compound (21) can be prepared by coupling intermediate (15) in Process 3 with dicarboxylic acid (20) in a manner known per se in the art.

More specifically, intermediate (15) and dicarboxylic acid (20) can be treated in a solvent, in the presence of a coupling agent, in the presence of a base added as needed, at 0 to 100° C. for 0.5 to 30 hours (Process A); or intermediate (15) and a reactive derivative of dicarboxylic acid (20) are treated in a solvent, in the presence of a base added as needed, at 0 to 100° C. for 0.5 to 30 hours (Process B). In each of Process A and Process B, the reaction is preferably conducted at 0 to 50° C. for 0.5 to 5 hours.

Illustrative of suitable solvents employed in these reactions include dimethylformamide, tetrahydrofuran, dioxane, acetonitrile, methylene chloride, and dichloroethane. Illustrative of bases include organic bases such as pyridine, triethylamine, and N,N-diisopropylethylamine; and inorganic bases such as sodium carbonate and sodium hydrogencarbonate.

Further, examples of the coupling agent used in the process A include 1,3-dicyclohexylcarbodiimide, 1-cyclohexyl-3-morpholinoethylcarbodiimide, 1-(3-dimethylaminopropyl)-3-ethylcarbodiimide, 1,1'-carbonyldiimidazole, diethyl phosphorocyanidate, diphe- (Process 4):

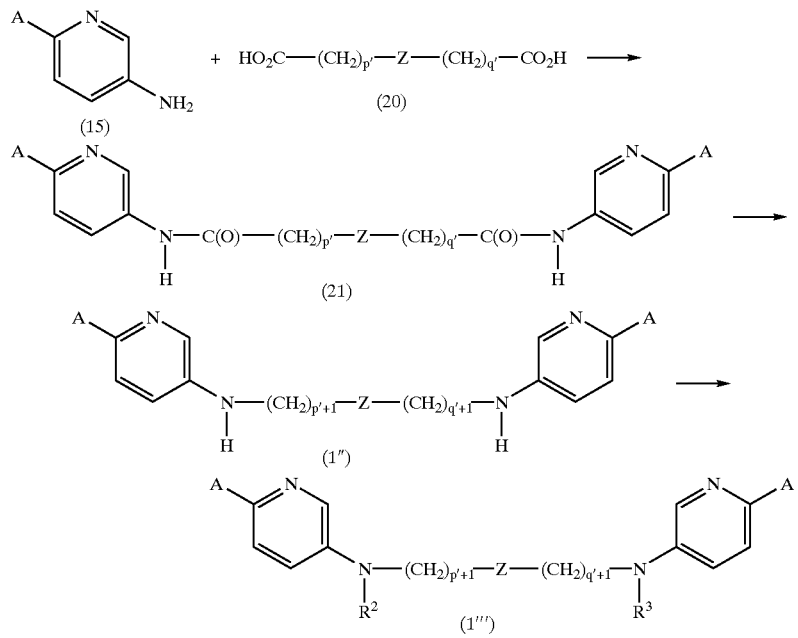

wherein the compounds of the reaction sequence above, A, Z, $R^2$ and $R^3$ have the same meanings as defined above, and p' and q' denote an integer of 1 to 5.

Embodiments of compound (1) include compounds (1") and (1'''), in each of which X is a group of formula (4) and p and q are integers of 2 to 6. The compound embodiments can be prepared by the reaction steps of Process 4.

nylphosphoryl azide, bis(2-oxo-3-oxazolidinyl)phosphonic chloride, and 2-chloro-1-methylpyridinium iodide. Suitable examples of the reactive derivative of the dicarboxylic acid (20) in Process B include acid halides such as acid chlorides, acid azides, mixed anhydrides with pivalic acid or the like, and activated esters such as cyanomethyl esters and p-nitrophenyl esters.

2) Synthesis of Compound (1") (Reduction)

Compound (1") can be prepared by treating compound (21) under similar conditions as in the reduction of compound (18) in Process 3.

3) Synthesis of Compound (1''') (Alkylation)

Compound (1''') can be prepared by treating compound (1") under similar conditions as in the alkylation of compound (19) in Process 3.

The intermediate and objective compounds prepared in the above reactions, respectively, can be isolated and purified by subjecting them to a purification procedure commonly employed in organic synthetic chemistry, for example, filtration, extraction, washing, drying, concentration, recrystallization, one or more of various types of chromatography, and the like. Further, the intermediate can be provided for use in the next reaction without specifically purifying the intermediate.

In addition, the intermediates and objective compounds may also be prepared in the form of solvates with reaction solvents, recrystallization solvents or the like, especially as hydrates. Further, compound (1) of the present invention may include various isomers depending on the kinds and combination of the substituents. It is to be noted that the present invention encompasses all of such isomers.

Compound (1) obtained as described above can be converted into an acid addition salt or a basic salt by a method known per se in the art. No particular limitation is imposed on such salts insofar as they are pharmacologically acceptable salts. When compound (1) is a basic compound, examples of pharmacologically acceptable salt include mineral acid salts such as the hydrochloride, sulfate and nitrate; and organic acid salts such as the methanesulfonate, acetate, oxalate and citrate. When compound (1) is an acidic compound, on the other hand, examples of its pharmacologically acceptable salt include alkali metal salts such as the sodium and potassium salts; alkaline earth metal salts such as the calcium and magnesium salts; and organic base salts such as the pyridine, picoline and triethylamine salts.

The bis (2-aryl-5-pyridyl) derivative (1) of the present invention has excellent IgE antibody production inhibiting activity as will be demonstrated in tests to be described subsequently herein and also, IL-4 production inhibiting activity and IL-5 production inhibiting activity. The compound is also useful as a medicinal agent for the prevention or treatment of various allergic diseases, for example, asthma, atopic dermatitis, allergic rhinitis, inflammatory bowel disease, contact skin dermatitis and allergic opthalmopathy, and also as an IgE antibody production inhibitor.

The medicinal agent of the present invention comprises, as an active ingredient, the bis(2-aryl-5-pyridyl) derivative or the salt thereof. By adding pharmacologically acceptable, inorganic or organic carriers, the bis(2-aryl-5-pyridyl) derivative or the salt thereof can be formulated into medicinal compositions, for example, various oral preparations or parenteral preparations such as solid, semi-solid or liquid preparations by methods known per se in the art.

Illustrative of preparations for oral administration include tablets, pills, granules, soft or hard capsules, triturates, subtilized granules, powders, emulsions, syrups, pellets, and elixirs. On the other hand, illustrative of preparations for parenteral administration include injections, drips, infusions, ointments, lotions, tonics, sprays, suspensions, medicinal oils, emulsions, suppositories, and instillations.

To formulate such preparations, methods known per se in the art can be followed. The active ingredient of the present invention can be used in combination with pharmacologically acceptable surfactants, excipients, coloring matters, flavoring agents, preservatives, stabilizers, buffering agents, suspending agents, isotonicities and the like as needed.

The dosage of the medicinal agent of the present invention varies inter alia depending on the medicine, the target disease to be treated or prevented, the method of administration, the treatment period, and the age, sex and weight of the patient. Nonetheless, the medicinal agent is preferably administered at a daily dosage ranging from 0.01 to 1,000 mg/kg weight in terms of the compound represented by formula (1). This dosage can be administered at once or in several portions, for example, 2 to 6 portions in a day.

Having now generally described this invention, a further understanding can be obtained by reference to certain specific examples which are provided herein for purposes of illustration only and are not intended to be limiting unless otherwise specified.

REFERENCE EXAMPLE 1

N,N'-bis(2-trifluoromethanesulfonyloxy-5-pyridyl)-N,N'-dimethylethylenediamine

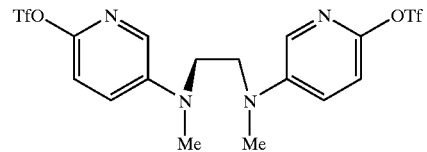

Under argon, tri-t-butylphosphine (5.0 mL, 20 mmol), sodium t-butoxide (10.78 g, 112 mmol), 2-benzyloxy-5-bromopyridine [*J. Am. Chem. Soc.*, 71, 70–73 (1949).] (29.20 g, 110 mmol) and a solution of N,N'-dimethylethylenediamine (4.40 g, 50.0 mmol) in o-xylene (30 mL) were added to a solution of bis (dibenzylideneacetone)palladium (2.86 g, 5.00 mmol) in o-xylene (80 mL). After stirring at 120° C. for 3 hours, water was added, and the resulting mixture was extracted with chloroform. The organic layer was washed with water, dried over anhydrous sodium sulfate, and concentrated under reduced pressure. The residue was purified by column chromatography on silica gel to afford N,N'-bis(2-benzyloxy-5-pyridyl)-N,N'-dimethylethylenediamine as a pale yellow crystalline powder (melting point: 95.0–97.0° C.) (18.59 g, yield: 81%).

A solution of N,N'-bis(2-benzyloxy-5-pyridyl)-N,N'-dimethylethylenediamine (18.50 g, 400 mmol) in trifluoroacetic acid (105 mL) was stirred at 50° C. for 4 hours. Diethyl ether (630 mL) was added to the ice-cold reaction mixture, and the mixture was stirred for 1 hour. Precipitated crystals were collected by filtration and then washed with diethyl ether to give N,N'-bis(2-hydroxy-5-pyridyl)-N,N'- dimethylethylenediamine ditrifluoroacetate as a yellow crystalline powder (melting point: 180.0–182.0° C.)(17.24 g, yield 86%).

N,N'-Bis(2-hydroxy-5-pyridyl)-N,N'-dimethylethylenediamine ditrifluoroacetate (18.00 g, 35.8 mmol) was suspended in methylene chloride (350 mL) and N,N-diisopropylethylamine (48 mL, 280 mmol) was added. The resulting mixture was cooled to −10° C., and trifluoromethanesulfonic anhydride (21 mL, 120 mmol) was added. After stirring for 30 minutes, N,N-diisopropylethylamine (12 mL, 70 mmol) and trifluoromethanesulfonic anhydride (21 mL, 120 mmol) were added. After being stirred further at −10° C. for 30 minutes, N,N-diisopropylethylamine (5.0 mL, 29 mmol) and trifluoromethanesulfonic anhydride (5.0 mL, 28 mmol) were added additionally, and the mixture was stirred for 1 hour in an ice bath. A saturated aqueous sodium carbonate (180 mL) and sodium carbonate (18 g, 0.17 mmol) were added, and the resulting mixture was extracted with methylene chloride. The organic layer was washed with brine, dried over anhydrous sodium sulfate, and concentrated under reduced pressure. The residue was purified by column chromatography on silica gel to obtain crude crystals. The crude crystals were recrystallized from chloroform-hexane to afford the title compound as pale brown needles (melting point: 146.0–148.0° C. )(13.44 g, yield: 70%).

REFERENCE EXAMPLE 2

5-Chloro-2-(3,4,5-trimethoxyphenyl)pyridine

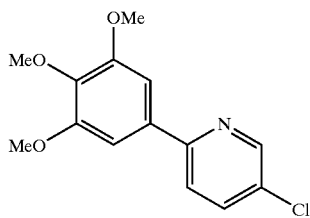

Under argon, 3,4,5-trimethoxyphenylboronic acid (5.05 g, 24.0 mmol), dichloro[1,2-bis(diphenylphosphino)ethane] palladium (574.0 mg, 1.00 mmol) and a 2.0 M aqueous sodium carbonate (20 mL, 40 mmol) were added to a solution of 2,5-dichloropyridine (2.95 g, 20.0 mmol) in ethanol-toluene (1:5, 54.0 mL). After stirring at 100° C. for 3 hours, water was added, and the mixture was extracted with ethyl acetate. The organic layer was dried over anhydrous sodium sulfate and concentrated under reduced pressure. The residue was purified by column chromatography on silica gel to afford the title compound as a colorless crystalline powder (melting point: 61.0–63.0° C.)(4.13 g, yield 73%)

REFERENCE EXAMPLE 3

4-Ethoxy-3,5-dimethoxyphenylboronic acid

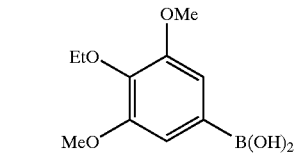

To a solution of 4-iodo-2,6-dimethoxyphenol (JP61-207432A) (100.0 mg, 0.360 mmol) in dimethylformamide (1.0 mL) were added ethyl iodide (84.0 mg, 0.540 mmol) and a 50% dispersion of sodium hydride in mineral oil (19.0 mg, 0.40 mmol). After stirring at room temperature for 1 hour, the reaction mixture was poured into 0.10 M hydrochloric acid, and the resulting mixture was extracted with diethyl ether. The organic layer was washed with saturated aqueous sodium hydrogencarbonate and brine, dried over anhydrous sodium sulfate, and concentrated under reduced pressure. The residue was purified by column chromatography on silica gel to afford 4-ethoxy-1-iodo-3,5-dimethoxybenzene as a colorless amorphous powder (102.0 mg, yield: 93%).

Under argon, a 1.60 M solution of n-butyllithium in hexane (2.5 mL, 4.1 mmol) was added to anhydrous tetrahydrofuran (7.0 mL) stirred in a dry ice-acetone bath, followed by dropwise addition of a solution of 4-ethoxy-1-iodo-3,5-dimethoxybenzene (570.0 mg, 1.85 mmol) in anhydrous tetrahydrofuran (1.5 mL). After the mixture was stirred for 20 minutes in the dry ice-acetone bath, triisopropyl borate (0.50 mL, 2.2 mmol) was added, and the mixture was additionally stirred for 20 minutes. The reaction mixture was stirred at room temperature for 1 hour, and concentrated under reduced pressure. To the residue, a 0.1 M aqueous sodium hydroxide (4.4 mL) solution was added. The aqueous solution was washed with chloroform, acidified by the addition of concentrated hydrochloric acid, and extracted with chloroform. The organic layer was washed with brine, dried over anhydrous sodium sulfate, and concentrated under reduced pressure. Chloroform-hexane was added to the residue and the resulting precipitate was collected by filtration to afford the title compound as a colorless amorphous powder (162.0 mg, yield: 39%).

REFERENCE EXAMPLE 4

3,5-Dimethoxy-4-(2,2,2-trifluoroethoxy)phenylboronic acid

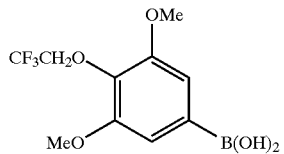

To a solution of methyl syringate (2.10 g, 9.90 mmol) in dimethylformamide (21.0 mL) were added potassium carbonate (13.60 g, 9.90 mmol) and 2,2,2-trifluoroethyl trifluoromethanesulfonate (purity: 25%) (J. Org. Chem., 30, 4322–4324 (1965)) (10.90 g, 12 mmol). After stirring at room temperature for 1 hour and at 50° C. for 3 hours, water was added and the resulting mixture was extracted with diethyl ether. The organic layer was washed with brine, dried over anhydrous sodium sulfate, and concentrated under reduced pressure to prepare an oil (2.69 g) containing methyl 3,5-dimethoxy-4-(2,2,2-trifluoroethoxy)benzoate.

To a solution of the oil (2.69 g) obtained in methanol (14 mL) was added a 5.0 M aqueous sodium hydroxide (14 mL, 70 mmol), and the resulting mixture was stirred at 80° C. for 30 minutes. The reaction mixture was concentrated under reduced pressure to remove the methanol, acidified by the addition of concentrated hydrochloric acid, and extracted with chloroform. The organic layer was washed with brine, dried over anhydrous sodium sulfate, and concentrated under reduced pressure to yield an oil (2.56 g) containing 3,5-dimethoxy-4-(2,2,2-trifluoroethoxy)benzoic acid.

To a solution of the oil (2.45 g) prepared by the above-described procedure in t-butyl alcohol (37 mL) were added triethylamine (0.93 g, 9.2 mmol) and diphenylphosphoryl azide (2.53 g, 9.20 mmol). After stirring at 100° C. for 2 hours, the reaction mixture was concentrated under reduced pressure. A solution of the residue in ethyl acetate was washed with saturated aqueous sodium hydrogencarbonate and brine, dried over anhydrous sodium sulfate, and concentrated under reduced pressure. The residue was purified by column chromatography on silica gel to provide N-t-butoxycarbonyl-3,5-dimethoxy-4-(2,2,2-trifluoroethoxy) aniline as a colorless oil (1.10 g, yield: 36% based on methyl syringate).

N-t-butoxycarbonyl-3,5-dimethoxy-4-(2,2,2-trifluoroethoxy)aniline (1.10 g, 3.13 mmol) was added to a 10% solution of hydrogen chloride in methanol (20 mL, 55 mmol), and the resulting solution was stirred at 50° C. for 30 minutes. The reaction mixture was concentrated under reduced pressure to give crude 3,5-dimethoxy-4-(2,2,2-trifluoroethoxy)aniline hydrochloride.

The crude 3,5-dimethoxy-4-(2,2,2-trifluoroethoxy)-aniline hydrochloride prepared by the above-described procedure was suspended in water (16 mL), and to the ice-cold suspension were added concentrated hydrochloric acid (0.26 mL, 3.1 mmol) and a solution of sodium nitrite (227.0 mg, 3.29 mmol) in water (2.0 mL) dropwise over about 5 minutes. The resulting mixture was stirred for 15 minutes, and a solution of potassium iodide (562.0 mg, 3.44 mmol) in water (2.0 mL) was added. The reaction mixture was stirred at room temperature for 1 hour and at 50° C. for 15 minutes, then extracted with ethyl acetate. The organic layer was washed with brine, dried over anhydrous sodium sulfate, and concentrated under reduced pressure. The residue was purified by column chromatography on silica gel to yield 1-iodo-3,5-dimethoxy-4-(2,2,2-trifluoroethoxy) benzene as a colorless oil [1.00 g, yield: 88% based on N-t-butoxy-carbonyl-3,5-dimethoxy-4-(2,2,2-trifluoroethoxy)aniline].

Applying the synthetic procedure of 4-ethoxy-3,5-dimethoxyphenylboronic acid from 4-ethoxy-1-iodo-3,5-dimethoxybenzene in Reference Example 3, the title compound was prepared as a colorless amorphous powder (369.0 mg, yield: 48%) from 1-iodo-3,5-dimethoxy-4-(2,2,2-trifluoroethoxy)-benzene (1.00 g, 2.76 mmol).

REFERENCE EXAMPLE 5

4-(2-Methoxyethoxy)-3,5-dimethoxyphenylboronic acid

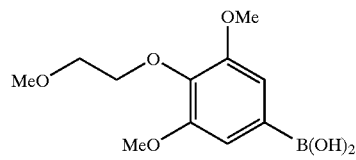

To a solution of 4-iodo-2,6-dimethoxyphenol (JP61-207432A) (280.0 mg, 1.00 mmol) in dimethylformamide (3.0 mL) were added potassium carbonate (184.0 mg, 1.10 mmol) and ethyl bromoacetate (184.0 mg, 1.10 mmol). After the resulting mixture was stirred at room temperature for 1 hour and at 50° C. for 1 hour, water was added, and resulting mixture was extracted with diethyl ether. The organic layer was washed with brine, dried over anhydrous sodium sulfate, and concentrated under reduced pressure to afford an oil (351.0 mg) containing 4-ethoxy-carbonylmethyloxy-1-iodo-3,5-dimethoxybenzene.

Lithium aluminum hydride (11.0 mg, 0.29 mmol) was added to an ice-cold solution of the oil (155.0 mg, approx. 0.42 mmol) prepared by the above-described procedure in anhydrous diethyl ether (2.0 mL), and the mixture was stirred for 10 minutes. After the resulting mixture was stirred at room temperature for 1 hour, 3.0 M hydrochloric acid was added, and the aqueous layer was extracted with diethyl ether. The organic layer was washed with saturated aqueous sodium hydrogencarbonate and brine, dried over anhydrous sodium sulfate, and concentrated under reduced pressure. The residue was purified by column chromatography on silica gel to afford 4-(2-hydroxyethoxy)-1-iodo-3,5-dimethoxybenzene as a colorless oil (83.0 mg, yield: 59% based on 4-iodo-2,6-dimethoxyphenol).

Methyl iodide (0.010 mL, 0.16 mmol) and a 50% dispersion of sodium hydride in mineral oil (12.0 mg, 0.24 mmol) were added to a solution of 4-(2-hydroxyethoxy)-1-iodo-3, 5-dimethoxybenzene (39.0 mg, 0.120 mmol) in anhydrous tetrahydrofuran (1.0 mL), and the mixture was stirred at room temperature for 1 hour. Water was added to the reaction mixture, and the mixture was extracted with diethyl ether. The organic layer was washed with 3.0 M hydrochloric acid, saturated aqueous sodium hydrogencarbonate and brine, dried over anhydrous sodium sulfate, and then concentrated under reduced pressure. The residue was purified by column chromatography on silica gel to yield 1-iodo-3, 5-dimethoxy-4-(2-methoxyethoxy)benzene as a colorless oil (40.0 mg, yield: 98%).

Applying the synthetic procedure of 4-ethoxy-3,5-dimethoxyphenylboronic acid from 4-ethoxy-1-iodo-3,5-dimethoxybenzene in Reference Example 3, the title compound was obtained as a colorless amorphous powder (276.0 mg, yield: 54%) from 1-iodo-3,5-dimethoxy-4-(2-methoxyethoxy)benzene (673.0 mg, 2.00 mmol).

REFERENCE EXAMPLE 6

4-[2-(t-butyldimethylsiloxy)ethoxy]-3,5-dimethoxyphenylboronic acid

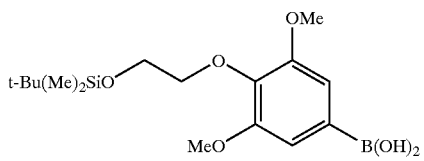

To a solution of 4-(2-hydroxyethoxy)-1-iodo-3,5-dimethoxybenzene (2.76 g, 8.52 mmol) synthesized by the process shown in Reference Example 5 in dimethylformamide (25 mL) were added imidazole (1.16 g, 17.0 mmol) and t-butylchlorodimethylsilane (1.61 g, 10.7 mmol), and the mixture was stirred at 50° C. for 3 hours. Water was added to the reaction mixture, and the mixture was extracted with ethyl acetate-hexane (1:1). The organic layer was washed with water and brine, dried over anhydrous sodium sulfate, and concentrated under reduced pressure. The residue was purified by column chromatography on silica gel to yield 4-[2-(t-butyldimethylsiloxy)-ethoxy]-1-iodo-3,5-dimethoxybenzene as a colorless oil (3.56 g, yield: 95%).

Applying the synthetic procedure of 4-ethoxy-3,5-dimethoxyphenylboronic acid from 4-ethoxy-1-iodo-3,5-dimethoxybenzene in Reference Example 3, the title compound was obtained as a colorless amorphous powder (1.15 g; quantitative) from 4-[2-(t-butyldimethylsiloxy)ethoxy]-1-iodo-3,5-dimethoxybenzene (1.42 g, 3.24 mmol).

REFERENCE EXAMPLE 7

3,5-Dimethoxy-4-(N-methoxy-N-methylcarbamoyl)phenylboronic acid

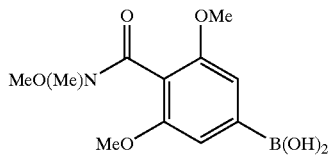

To a solution of 4-iodo-2,6-dimethoxybezoic acid (308.0 mg, 1.00 mmol) in methylene chloride (5.0 mL) were added dimethylformamide (0.020 mL, 0.26 mmol) and oxalyl chloride (0.13 mL, 1.5 mmol), and the resulting mixture was stirred for 30 minutes. The reaction mixture was poured into an ice-cold solution of N,O-dimethylhydroxyamine hydrochloride (488.0 mg, 5.00 mmol) and N,N-diisopropylethylamine (1.74 mL, 10.0 mmol) in methylene chloride (5.0 mL). The ice bath was removed, and the mixture was stirred at room temperature for 30 minutes. 0.1 M Hydrochloric acid was added to the reaction mixture, and the resulting mixture was extracted with chloroform. The organic layer was washed with 0.1 M aqueous sodium hydroxide and brine, dried over anhydrous sodium sulfate, and concentrated under reduced pressure. Hexane was added to the residue and the resulting precipitate was collected by filtration to yield crude 4-iodo-N,2,6-trimethoxy-N-methylbenzamide as a pale yellow crystalline powder (305.0 mg, yield: approx. 87%).

Applying the synthetic procedure of 4-ethoxy-3,5-dimethoxyphenylboronic acid from 4-ethoxy-1-iodo-3,5-dimethoxybenzene in Reference Example 3, the title compound was obtained as a pale yellow amorphous powder (91.0 mg, yield: 36% based on 4-iodo-2,6-dimethoxybenzoic acid) from the crude 4-1-iodo-N,2,6-trimethoxy-N-methylbenzamide (287.0 mg, approx. 0.82 mmol).

REFERENCE EXAMPLE 8

(4-Acetyl-3,5-dimethoxyphenyl)trimethyltin

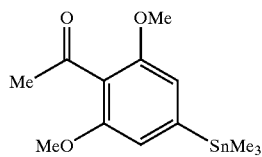

Aluminum chloride (87.05 g, 653.0 mmol) was gradually added to a solution of 3,5-dimethoxyaniline (20.0 g, 13 1.0 mmol) and acetic anhydride (30.9 mL, 328 mmol) in methylene chloride (650 mL) stirred in a sodium chloride-ice bath. The resulting mixture was stirred in the sodium chloride-ice bath for 20 minutes and at room temperature for 1 hour. The reaction mixture was poured into ice water, and the mixture was extracted with chloroform. The organic layer was washed with saturated aqueous sodium hydrogencarbonate and brine, dried over anhydrous sodium sulfate, and concentrated under reduced pressure. The residue was purified by column chromatography on silica gel to prepare crude crystals. The crude crystals were recrystallized from diethyl ether-hexane to yield 4-acetamido-2,6-dimethoxyacetophenone as a pale yellow crystalline powder (melting point 184.0–187.0° C. )(9.42 g, yield: 26%).

To a suspension of 4-acetamido-2,6-dimethoxyacetophenone (9.42 g, 39.7 mmol) in ethanol (400 mL) was added a 5.0 M aqueous sodium hydroxide solution (80 mL, 400 mL) and the mixture was stirred at 95° C. for 3 hours. The reaction mixture was concentrated under reduced pressure, water was added to the residue, and the resulting mixture was extracted with chloroform. The organic layer was washed with brine, dried over anhydrous sodium sulfate, and concentrated under reduced pressure. The residue was suspended in diethyl ether-hexane (1:4) and collected by filtration to yield 4-amino-2,6-dimethoxyacetophenone as a pale yellow crystalline powder (melting point: 155.0–158.0° C.) (7.58 g, yield: 98%).

To a suspension of 4-amino-2,6-dimethoxyacetophenone (7.58 g, 38.8 mmol) in water (155 mL) stirred in a sodium chloride-ice bath was added concentrated hydrochloric acid (6.5 mL, 78 mmol) to provide a homogeneous solution. To the solution stirred in the sodium chloride-ice bath was added a solution of sodium nitrite (2.81 g, 40.7 mmol) in water (8.0 mL) gradually and the resulting mixture was stirred in an ice bath for 15 minutes. A solution of potassium iodide (7.08 g, 42.7 mmol) in water (8.0 mL) and ethyl acetate (48 mL) were added, and the mixture was stirred at room temperature for 1 hour and at 50° C. for 15 minutes. After cooling, the aqueous layer was extracted with ethyl acetate. The organic layers were combined, washed with saturated aqueous sodium hydrogencarbonate, a 10% aqueous sodium thiosulfate and brine, dried over anhydrous sodium sulfate, and concentrated under reduced pressure. The residue was purified by column chromatography on silica gel to yield 4-iodo-2,6-dimethoxyacetophenone, obtained as a colorless crystalline powder (melting point: 124.0–129.0° C. )(9.50 g, yield: 80%).

Under nitrogen, to a solution of 4-iodo-2,6-dimethoxyacetophenone (287.0 mg, 1.86 mmol) in anhydrous 1,4-dioxane (12 mL) were added hexamethylditin (609.0 mg, 1.86 mmol) and tetrakis(triphenylphosphine)palladium (215.0 mg, 0.190 mmol), and the mixture was stirred at 110° C. for 4 hours. After cooling, water was added and the mixture was extracted with benzene. The organic layer was dried over anhydrous sodium sulfate and concentrated under reduced pressure. The residue was purified by column chromatography on silica gel to yield the title compound as a colorless oil (450.0 mg, yield: 71%).

REFERENCE EXAMPLE 9

N,N'-Bis(2-chloro-5-pyridyl)-N,N'-dimethylethylenediamine

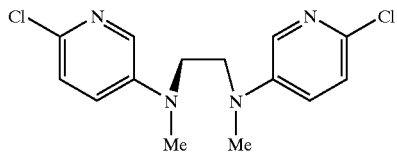

To phosphorus oxychloride (16.4 mL) were added N,N'-bis(2-hydroxy-5-pyridyl)-N,N'-dimethylethylenediamine ditrifluoroacetate (824.0 mg, 1.64 mmol) synthesized by the method described in Reference Example 1 and phosphorus pentachloride (171.0 mg, 0.820 mmol). The resulting mixture was stirred at 100° C. for 8 hours. After cooling, the reaction mixture was poured into ice water. The mixture was rendered basic by adding sodium hydroxide and then extracted with chloroform. The organic layer was dried over anhydrous sodium sulfate and concentrated under reduced pressure to afford crude crystals of the title compound as a pale brown crystalline powder (melting point: 173.0–179.0° C.)(439.0 mg, yield: approx. 86%).

REFERENCE EXAMPLE 10

2-Benzyloxy-N,N'-dimethyl-1,3-propanediamine

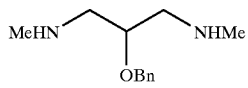

To a solution of 2-hydroxy-1,3-propanediamine (0.90 g, 10 mmol) in tetrahydrofuran (40 mL) was added triethylamine (3.94 g, 39 mmol). To the ice-cold solution was added a solution of ethyl chloroformate (3.58 g, 33 mmol) in tetrahydrofuran (10 mL) dropwise. The resulting mixture was stirred for 15 hours, and filtered to remove insoluble materials. The filtrate was dried over anhydrous sodium sulfate and concentrated under reduced pressure to yield an oil (1.95 g) containing N,N'-bis(ethoxycarbonyl)-2-ethoxycarbonyloxy-1,3-propanediamine.

Lithium aluminum hydride (780.0 mg, 20.7 mmol) was added to a solution of the oil (1.95 g, approx. 6.5 mmol) prepared by the above-described procedure in tetrahydrofuran (40 mL). An ice bath was removed, and the mixture was stirred at 80° C. for 17 hours. After cooling, anhydrous sodium sulfate (25.0 g) was added to the reaction mixture. Insoluble materials were removed by filtration through Celite, and the filtrate was concentrated under reduced pressure. The residue was purified by column chromatography on silica gel to give 2-hydroxy-N,N'-dimethyl-1,3-propanediamine as a pale yellow oil (277.0 mg, yield: 23% based on 2-hydroxy-1,3-propanediamine).

To a solution of 2-hydroxy-N,N'-dimethyl-1,3-propanediamine (165.0 mg, 1.39 mmol) in acetonitrile (5.0 mL) were added triethylamine (564.0 mg, 5.58 mmol) and di-t-butyl dicarbonate (912.0 mg, 4.18 mmol). After stirring at room temperature for 15 hours, 0.10 M hydrochloric acid was added and the mixture was extracted with chloroform. The organic layer was washed with brine, dried over anhydrous sodium sulfate, and concentrated under reduced pressure. The residue was purified by column chromatography on silica gel to provide N,N'-bis(t-butoxycarbonyl)-2-hydroxy-N,N'-dimethyl-1,3-propanediamine as a pale yellow oil (163.0 mg, yield: 36%).

To an ice-cold solution of N,N'-bis(t-butoxy-carbonyl)-2-hydroxy-N,N'-dimethyl-1,3-propanediamine (87.0 mg, 0.27 mmol) in tetrahydrofuran (4.0 mL) were added benzyl bromide (230.0 mg, 1.35 mmol) and a 50% dispersion of sodium hydride in mineral oil (35.0 mg, 0.81 mmol). The reaction mixture was stirred at room temperature for 15 hours and concentrated under reduced pressure. Water was added to the residue, and the mixture was extracted with ethyl acetate. The organic layer was washed with brine, dried over anhydrous sodium sulfate, and concentrated under reduced pressure. The residue was purified by column chromatography on silica gel to yield 2-benzyloxy-N,N'-bis(t-butoxycarbonyl)-N,N'-dimethyl-1,3-propanediamine, obtained as a colorless oil (54.0 mg, yield: 49%).

To a solution of 2-benzyloxy-N,N'-bis(t-butoxycarbonyl)-N,N'-dimethyl-1,3-propanediamine (73.0 mg, 0.17 mmol) in methylene chloride (2.0 mL) was added a 4.0 M solution of hydrogen chloride in ethyl acetate (1.0 mL, 4.0 mmol), and the mixture was stirred at room temperature for 4 hours. The reaction mixture was concentrated under reduced pressure, ethanol (5.0 mL) was added to the residue, and the resulting mixture was concentrated under reduced pressure. An approx. 10% solution of ammonia in methanol (2.0 mL, approx. 12 mmol) was added to the residue, insoluble materials were removed by filtration, and the filtrate was concentrated under reduced pressure. The residue was purified by column chromatography on silica gel to yield the title compound as a colorless oil (35.0 mg, yield: 98%).

REFERENCE EXAMPLE 11

5-Amino-2-(3,4,5-trimethoxyphenyl)pyridine

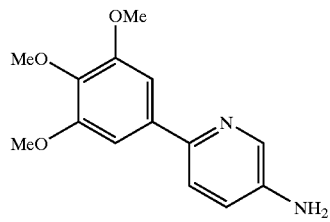

Under nitrogen, tetrakis(triphenylphosphine)palladium (504.6 mg, 0.437 mmol) and a 2.0 M aqueous sodium carbonate (25 mL, 50 mmol) were added to a solution of 2-bromo-5-nitropyridine (2.87 g, 14.1 mmol) and 3,4,5-trimethoxyphenylboronic acid (3.00 g, 14.2 mmol) in ethanol-toluene (1:5, 90 mL), and the resulting mixture was stirred at 70° C. for 12 hours. Water was added to the reaction mixture, and the aqueous layer was extracted with ethyl acetate. The organic layers were combined, dried over anhydrous sodium sulfate, and concentrated under reduced pressure. The residue was purified by column chromatography on silica gel and crude crystals were obtained. The crude crystals were recrystallized from chloroform-hexane to provide 5-nitro-2-(3,4,5-trimethoxyphenyl)pyridine as yellow needles (melting point: 134.0–136.5° C.)(3.31 g, yield: 81%).

To a solution of 5-nitro-2-(3,4,5-trimethoxyphenyl)pyridine (1.50 g, 5.17 mmol) in methanol-ethyl acetate (1:4, 50 mL) was added 10% palladium on charcoal (158.6 mg), and the resulting mixture was stirred at 45° C. for 2 hours and 30 minutes under hydrogen. Insoluble materials were removed by filtration through Celite, and the filtrate was concentrated under reduced pressure. The residue was recrystallized from ethyl acetate-hexane to yield the title compound as colorless needles (melting point: 153.5–155.5° C.)(1.25 g, yield: 93%).

REFERENCE EXAMPLE 12

N,N'-Dimethyl-3-(1-pyrrolidinyl)-1,5-pentanediamine

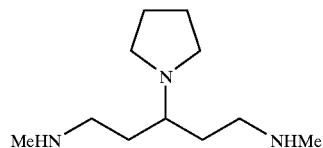

Following the process described in the publication [*J. Am. Chem. Soc.*, 110, 6127–6179 (1988)], N,N'-dibenzyl-N,N'-dimethyl-3-(1-pyrrolidinyl)glutaramide was prepared as a colorless oil (2.81 g, yield: 90% based on 6-chloro-2-pyrone) from 6-chloro-2-pyrone (1.00 g, 7.66 mmol) and N-methylbenzylamine (3.71 g, 30.6 mmol) via crude N,N'-dibenzyl-N,N'-dimethylglutaconamide (2.67 g).

Under nitrogen, lithium aluminum hydride (0.44 g, 12 mmol) was added to a solution of N,N'-dibenzyl-N,N'-dimethyl-3-(1-pyrrolidinyl)glutaramide (1.16 g, 2.85 mmol) in anhydrous tetrahydrofuran (20 mL) stirred in an ice bath, and the mixture was stirred at 65° C. for 2 hours. Methanol (3.0 mL, 74 mmol) was added to the ice-cold reaction mixture, and the ice bath was removed. Water (2.0 mL), diethyl ether (150 mL) and anhydrous magnesium sulfate (15 g) were added, and the mixture was stirred at room temperature for 1 hour. Insoluble materials were removed by filtration through Celite, an the filtrate was concentrated under reduced pressure. The residue was purified by column chromatography on silica gel to yield N,N'-dibenzyl-N,N'-dimethyl-3-(1-pyrrolidinyl)-1,5-pentanediamine as a colorless oil (917.3 mg, yield: 85%).

To a solution of N,N'-dibenzyl-N,N'-dimethyl-3-(1-pyrrolidinyl)-1,5-pentanediamine (249.1 mg, 0.657 mmol) in methanol (3.0 mL) were added concentrated hydrochloric acid (0.33 mL, 4.0 mmol) and 10% palladium on charcoal (50.0 mg), and the mixture was stirred at 50° C. for 14 hours under hydrogen. Insoluble materials were removed by filtration through a membrane filter, and the filtrate was concentrated under reduced pressure. The residue was adsorbed on an alumina column, and eluted with methanol-chloroform (1:4). The eluate was concentrated under reduced pressure to afford the title compound as a colorless oil (101.9 mg, yield: 78%).

EXAMPLE 1

N,N'-Bis[2-(2,3-dimethoxyphenyl)-5-pyridyl]-N,N'-dimethylethylenediamine

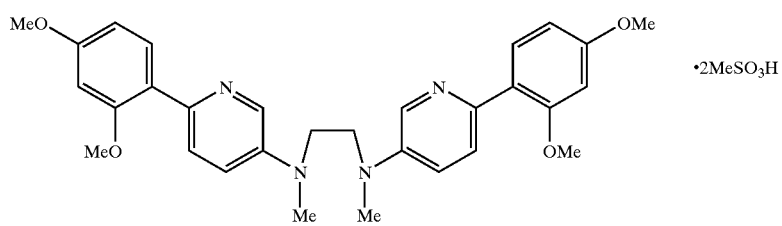

To a solution of N,N'-bis(2-trifluoromethanesulfonyloxy-5-pyridyl)-N,N'-dimethylethylenediamine (108.0 mg, 0.200 mmol) synthesized in Reference Example 1 in ethanol-toluene (1:6, 3.5 mL) were added 2,4-dimethoxyphenylboronic acid (108.0 mg, 0.200 mmol), tetrakis-(triphenylphosphine)palladium (46.0 mg, 0.040 mmol) and a 2.0 M aqueous sodium carbonate solution (0.20 mL, 0.40 mmol). After stirring at 80° C. for 2 hours, brine was added, and the mixture was extracted with chloroform. The organic layer was washed with brine, dried over anhydrous sodium sulfate, and concentrated under reduced pressure. The residue was purified column chromatography on silica gel to provide N,N'-bis[2-(2,4-dimethoxyphenyl)-5-pyridyl]-N,N'-dimethylethylenediamine as a colorless amorphous powder (109.0 mg; quantitative).

To a solution of N,N'-bis[2-(2,4-dimethoxyphenyl)-5-pyridyl]-N,N'-dimethylethylenediamine (108.0 mg, 0.200 mmol) in methanol (2.0 mL) was added a 1.0 M solution of methanesulfonic acid in methanol (0.44 mL, 0.44 mmol), and the reaction mixture was concentrated under reduced pressure. The residue was recrystallized from methanol-diethyl ether to yield the title compound as a yellow crystalline powder (melting point: 195.0–197.0° C.) (61.0 mg, yield: 43%).

$^1$H-NMR (DMSO-$d_6$, 120° C. )(ammonium salt $NH^+$ protons were not observed) δ: 2.38(s, 6H), 3.07(s, 6H), 3.75(s, 4H), 3.85(s, 12H), 6.70(dd, J=2.4, 8.5 Hz, 2H), 6.74(d, J=2.4 Hz, 2H), 7.51(d, J=8.5 Hz, 2H), 7.69(dd, J=2.9, 9.2 Hz, 2H),7.82(d, J=9.2 Hz, 2H), 8.01(d, J=2.9 Hz, 2H).

EXAMPLE 2

N,N'-Bis[2-(2,3-dimethoxyphenyl)-5-pyridyl]-N,N'-dimethylethylenediamine dimethanesulfonate

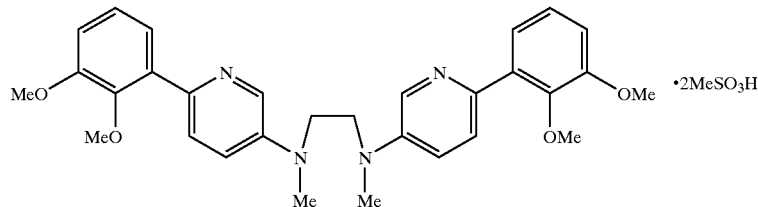

Following the procedure of Example 1, N,N'-bis[2-(2,3-dimethoxyphenyl)-5-pyridyl]-N,N'-dimethylethylenediamine was prepared as a colorless oil (33.0 mg, yield: 31%) from N,N'-bis(2-trifluoromethanesulfonyloxy-5-pyridyl)-N,N'-dimethylethylenediamine (114.0 mg, 0.212 mmol) synthesized as in Reference Example 1 and 2,3-dimethoxyphenylboronic acid (128.0 mg, 0.850 mmol).

To a solution of N,N'-bis[2-(2,3-dimethoxyphenyl)-5-pyridyl]-N,N'-dimethylethylenediamine (33.0 mg, 0.0641 mmol) in chloroform (3.0 mL) was added a 1.0 M solution of methanesulfonic acid in methanol (0.13 mL, 0.13 mmol), and the reaction mixture was concentrated under reduced pressure. Methanol-diethyl ether was added to the residue and the resulting precipitate was collected by filtration to yield the title compound as a yellow crystalline powder (melting point: 191.5–194.5° C.)(39.5 mg, yield: 87%).

$^1$H-NMR (CDCl$_3$)(ammonium salt $NH^+$ protons were not observed) δ: 2.85(s, 6H), 3.39(s, 6H), 3.79(s, 6H), 3.83(s, 4H), 3.92(s, 6H), 7.03–7.40(m, 6H), 7.61(br d, J=9.2 Hz, 2H), 7.97(d, J=9.2 Hz, 2H), 8.95(br s, 2H).

EXAMPLE 3

N,N'-Bis[2-(2,6-dimethoxyphenyl)-5-pyridyl]-N,N'dimethylethylenediamine dimethanesulfonate

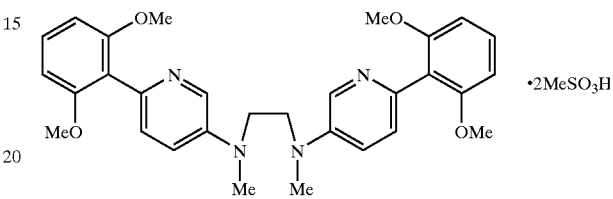

Following the procedure of Example 1, crude crystals were obtained from N,N'-bis(2-trifluoromethanesulfonyloxy-5-pyridyl)-N,N'-dimethylethylenediamine (150.0 mg, 0.279 mmol) synthesized in Reference Example 1 and 2,6-dimethoxyphenylboronic acid (150.7 mg, 1.00 mmol). The crude crystals were recrystallized from chloroform-diethyl ether-hexane to yield N,N'-bis[2-(2,6-dimethoxyphenyl)-5-pyridyl]-N,N'-dimethylethylenediamine as a colorless crystalline powder (77.3 mg, yield: 54%).

To a solution of N,N'-bis[2-(2,6-dimethoxyphenyl)-5-pyridyl]-N,N'-dimethylethylenediamine (72.3 mg, 0.141 mmol) in methanol-chloroform (9:1, 10 mL) was added a 1.0 M aqueous methanesulfonic acid solution (0.35 mL, 0.35 mmol), and the reaction mixture was concentrated under reduced pressure. Ethanol (5.0 mL) was added to the residue, and the mixture was concentrated under reduced pressure. The residue was recrystallized from ethanol-diethyl ether to provide the title compound as a pale yellow crystalline powder (melting point: 243.0–245.0° C. )(94.1 mg, yield: 95%).

$^1$H-NMR (CDCl$_3$)(ammonium salt $NH^+$ protons were not observed) δ: 2.79(s, 6H), 3.28(s, 6H), 3.79(s, 4H), 3.83(s, 12H), 6.65(d, J=8.5 Hz, 4H), 7.39(t, J=8.5 Hz, 2H), 7.52(br dd, J=3.1, 9.2 Hz, 2H), 7.69(br d, J=9.2 Hz, 2H), 8.91(br d, J=3.1 Hz, 2H).

EXAMPLE 4

N,N'-Bis[2-(3,5-dimethoxyphenyl)-5-pyridyl]-N,N'-dimethylethylenediamine

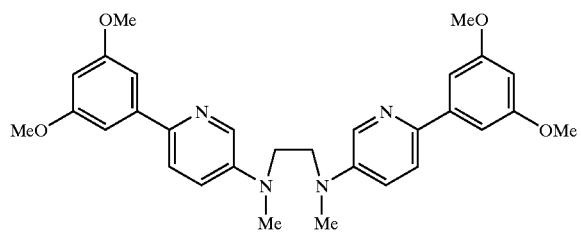

Following the procedure of Example 1, an oil was obtained from N,N'-bis(2-trifluoromethanesulfonyloxy-5-pyridyl)-N,N'-dimethylethylenediamine (108.0 mg, 0.200 mmol) synthesized in Reference Example 1 and 2,5-dimethoxyphenylboronic acid (91.0 mg, 0.500 mmol). Chloroform-diethyl ether-hexane was added to the oil and the resulting precipitate was collected by filtration to yield the title compound as a pale yellow crystalline powder (melting point: 139.0–141.0° C. )(41.2 mg, yield: 40%).

$^1$H-NMR (CDCl$_3$) δ: 3.02(s, 6H), 3.66(s, 4H), 3.87(s, 12H), 6.46(br s, 2H), 6.99(br d, J=9.2 Hz, 2H), 7.11 (br s, 4H), 7.57(br d, J=9.2 Hz, 2H), 8.22(br s, 2H).

EXAMPLE 5

N,N'-Bis[2-(2,3,5-trimethoxyphenyl)-5-pyridyl]-N,N'-dimethylethylenediamine

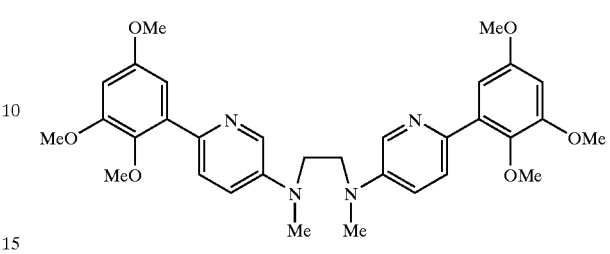

Following the procedure of Example 1, crude crystals were obtained from N,N'-bis(2-trifluoromethanesulfonyloxy-5-pyridyl)-N,N'-dimethylethylenediamine (150.0 mg, 0.280 mmol) synthesized in Reference Example 1 and 2,3,5-trimethoxyphenylboronic acid (131.0 mg, 0.620 mmol). The crude crystals were recrystallized from chloroform-hexane to yield the title compound as pale brown needles (melting point: 171.0–172.0° C. )(37.0 mg, yield: 56%).

$^1$H-NMR (CDCl$_3$) δ: 3.05(s, 6H), 3.60(s, 6H), 3.67(s, 4H), 3.85(s, 6H), 3.88(s, 6H), 6.50(d, J=2.9 Hz, 2H), 6.95(d, J=2.9 Hz, 2H), 7.01(dd, J=2.9, 8.8 Hz, 2H), 7.85(d, J=8.8 Hz, 2H), 8.25(d, J=2.9 Hz, 2H).

EXAMPLE 6

N,N'-Bis[2-(2,4,6-trimethoxyphenyl)-5-pyridyl]-N,N'-dimethylethylenediamine

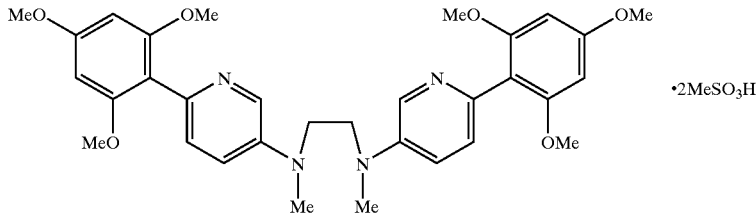

Following the procedure of Example 1, N,N'-bis[2-(2,4,6-trimethoxyphenyl)-5-pyridyl]-N,N'-dimethylethylenediamine was obtained as a colorless oil (20.1 mg, yield: 13%) from N,N'-bis(2-trifluoromethanesulfonyloxy-5-pyridyl)-N,N'-dimethylethylenediamine (150.3 mg, 0.279 mmol) synthesized in Reference Example 1 and 2,4,6-trimethoxyphenylboronic acid (124.5 mg, 0.692 mmol).

To a solution of N,N'-bis[2-(2,4,6-trimethoxyphenyl)-5-pyridyl]-N,N'-dimethylethylenediamine (20.1 mg, 0.0350 mmol) in methanol-chloroform (1:1, 5 mL) was added a 1.0 M aqueous methanesulfonic acid solution (0.090 mL, 0.090 mmol), and the reaction mixture was concentrated under reduced pressure. Ethanol (5.0 mL) was added to the residue, and the mixture was concentrated under reduced pressure. The residue was recrystallized from methanol-diethyl ether to yield the title compound as pale yellow fine flakes (melting point: 264.0–265.0° C.)(15.6 mg, yield: 59%).

$^1$H-NMR [CD$_3$OD-CDCl$_3$(1:20)](ammonium salt NH$^+$ protons were not observed) δ: 2.77(s, 6H), 3.19(s, 6H), 3.80(s, 4H), 3.82(s, 12H), 3.88(s, 6H), 6.21(s, 4H), 7.59(dd, J=3.1, 9.3 Hz, 2H), 7.69(d, J=9.3 Hz, 2H), 8.50(dd, J=3.1 Hz, 2H).

EXAMPLE 7

N,N'-Bis[2-(3,4,5-trimethoxyphenyl)-5-pyridyl]-N,N'-dimethylethylenediamine dimethanesulfonate mmol) and the reaction mixture was concentrated under reduced pressure. Ethanol (5.0 mL) was added to the residue and the mixture was concentrated under reduced pressure. The residue was recrystallized from methanol-methylene chloride-diethyl ether to provide the title compound as a yellow crystalline powder (melting point: 247.0–249.0° C.)(140.0 mg, yield: 76%).

$^1$H-NMR [DMSO-d$_6$, 120° C.](ammonium salt NH$^+$ protons were not observed) δ: 2.43(s, 6H), 3.05(s, 6H), 3.73(s, 4H), 3.76(s, 6H), 3.86(s, 12H), 7.16(s, 4H), 7.47(dd, J=3.1, 9.0 Hz, 2H), 7.86(d, J=9.0 Hz, 2H), 8.07(d, J=3.1 Hz, 2H).

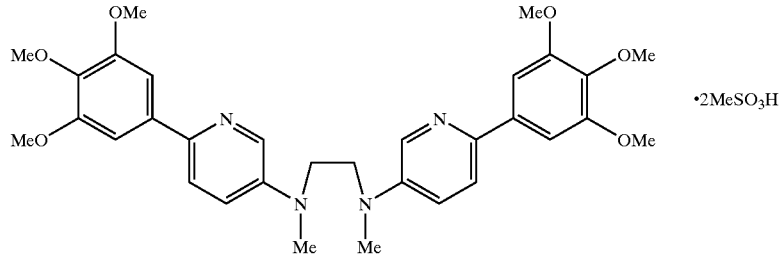

Under argon, tri-t-butylphosphine (101.0 mg, 0.500 mmol) was added to a solution of bis(dibenzylideneacetone)palladium (71.0 mg, 0.120 mmol) in o-xylene (3.0 mL). To the resulting solution were added 5-chloro-2-(3,4,5-trimethoxyphenyl)pyridine (335.0 mg, 1.20 mmol) synthesized in Reference Example 2, N,N'-dimethylethylenediamine (44.0 mg, 0.500 mmol), and sodium t-butoxide (106.0 mg, 1.10 mmol). After stirring at 120° C. for 12 hours, water was added to the reaction mixture and the aqueous layer was extracted with chloroform. The organic layers were combined, dried over anhydrous sodium sulfate, and concentrated under reduced pressure. The residue was purified by column chromatography on silica gel to yield N,N'-bis[2-(3,4,5-trimethoxyphenyl)-5-pyridyl]-N,N'-dimethylethylenedi amine as a pale yellow amorphous powder (167.0 mg, yield: 58%).

To a solution of N,N'-bis[2-(3,4,5-trimethoxyphenyl)-5-pyridyl]-N,N'-dimethylethylenediamine (140.0 mg, 0.240 mmol) in methanol-methylene chloride (1:1, 6.0 mL) was added a 1.0 M aqueous methanesulfonic acid (0.48 mL, 0.48

EXAMPLE 8

N,N'-Bis[2-(4-ethoxy-3,5-dimethoxyphenyl)-5-pyridyl]-N,N'-dimethylethylenediamine dimethanesulfonate

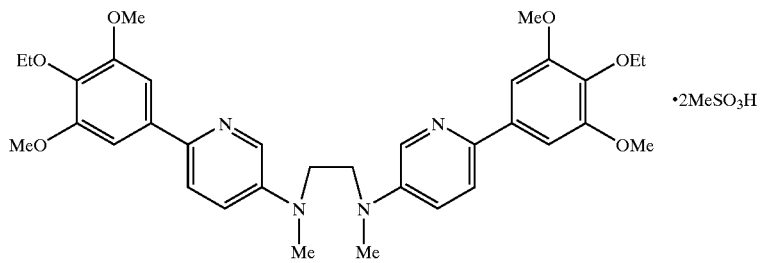

Following the procedure of Example 1, N,N'-bis[2-(4-ethoxy-3,5-dimethoxyphenyl)-5-pyridyl]-N,N'-dimethylethylenediamine was obtained as a colorless oil (133.0 mg, yield: 79%) from N,N'-bis(2-trifluoromethanesulfonyloxy-5-pyridyl)-N,N'-dimethylethylenediamine (150.0 mg, 0.280 mmol) synthesized in Reference Example 1 and 4-ethoxy-3,5-dimethoxyphenylboronic acid (140.0 mg, 0.620 mmol) synthesized in Reference Example 3.

To a solution of N,N'-bis[2-(4-ethoxy-3,5-dimethoxyphenyl)-5-pyridyl]-N,N'-dimethylethylenediamine (133.0 mg, 0.220 mmol) in methanol (2.0 mL) was added a 1.0 M aqueous methanesulfonic acid solution (0.44 mL, 0.44 mmol), and the reaction mixture was concentrated under reduced pressure. Ethanol (5.0 mL) was added to the residue, and the mixture was concentrated under reduced pressure. The residue was recrystallized from methanol-diethyl ether to afford the title compound as a yellow crystalline powder (melting point: 232.0–234.0° C.)(120.0 mg, yield: 54%).

$^1$H-NMR [CDCl$_3$](ammonium salt NH$^+$ protons were not observed) δ: 1.38(t, J=7.1 Hz, 6H), 2.87(s, 6H), 3.32(s, 6H), 3.80(s, 4H), 3.95(s, 12H), 4.12(q, J=7.1 Hz, 4H), 7.05(s, 4H), 7.70(dd, J=2.9, 9.3 Hz, 2H), 7.88(d, J=9.3, Hz, 2H), 8.71(d, J=2.9 Hz, 2H).

EXAMPLE 9

N,N'-Bis[2-(3,5-dimethoxy-4-propoxyphenyl)-5-pyridyl]-N,N'-dimethylethylenediamine dimethanesulfonate

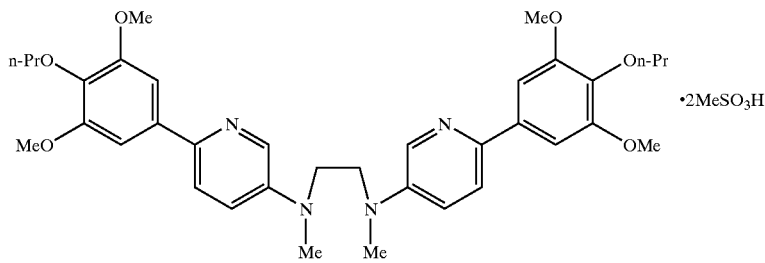

Following the procedure of Example 1, N,N'-bis[2-(3,5-dimethoxy-4-propoxyphenyl)-5-pyridyl]-N,N'-dimethylethylenediamine was obtained as a colorless oil (124.0 mg, yield: 98%) from N,N'-bis(2-trifluoromethanesulfonyloxy-5-pyridyl)-N,N'-dimethylethylenediamine (108.0 mg, 0.200 mmol) synthesized in Reference Example 1 and 4-propoxy-3,5-dimethoxyphenylboronic acid (105.0 mg, 0.440 mmol) synthesized by a similar procedure as described in Reference Example 3.

To a solution of N,N'-bis[2-(3,5-dimethoxy-4-propoxyphenyl)-5-pyridyl]-N,N'-dimethylethylenediamine (124.0 mg, 0.196 mmol) in methanol-chloroform (1:2, 3.0 mL) was added a 1.0 M aqueous methanesulfonic acid (0.41 mL, 0.41 mmol), and the reaction mixture was concentrated under reduced pressure. Ethanol (5.0 mL) was added to the residue, and the mixture was concentrated under reduced pressure. The residue was recrystallized from ethanol-diethyl ether-hexane to afford the title compound as yellow a crystalline powder (melting point: 241.0–243.0° C. ) (91.0 mg, yield: 56%).

$^1$H-NMR [DMSO-d$_6$, 120° C.](ammonium salt NH$^+$ protons were not observed) δ: 0.98(t, J=7.0 Hz, 6H), 1.67(tq, J=7.0, 7.0 Hz, 4H), 2.44(s, 6H), 3.06(s, 6H), 3.73(s, 4H), 3.85(s, 12H), 3.91(t, J=7.0 Hz, 4H), 7.16(s, 4H), 7.47(dd, J=2.9, 9.0 Hz, 2H), 7.86(d, J=9.0 Hz, 2H), 8.06(d, J=2.9 Hz, 2H).

EXAMPLE 10

N,N'-Bis[2-(4-isopropoxy-3,5-dimethoxyphenyl)-5-pyridyl]-N,N'-dimethylethylenediamine dimethanesulfonate

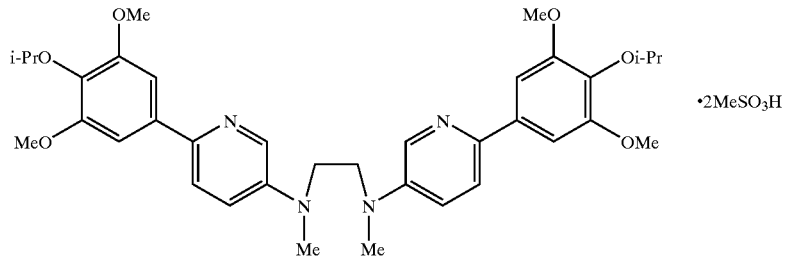

Following the procedure of Example 1, N,N'-bis[2-(4-isopropoxy-3,5-dimethoxyphenyl)-5-pyridyl]-N,N'-dimethylethylenediamine was obtained as a colorless oil (74.0 mg, yield: 92%) from N,N'-bis(2-trifluoromethanesulfonyloxy-5-pyridyl)-N,N'-dimethylethylenediamine (69.0 mg, 0.130 mmol) synthesized as described in Reference Example 1 and 4-isopropoxy-3,5-dimethoxyphenylboronic acid (61.0 mg, 0.260 mmol) synthesized by a similar procedure as described in Reference Example 3.

To a solution of N,N'-bis[2-(4-isopropoxy-3,5-dimethoxyphenyl)-5-pyridyl]-N,N'-dimethylethylenediamine (74.0 mg, 0.12 mmol) in methanol (2.0 mL) was added a 1.0 M aqueous methanesulfonic acid solution (0.26 mL, 0.26 mmol), and the reaction mixture was concentrated under reduced pressure. Ethanol (5.0 mL) was added to the residue, and the mixture was concentrated under reduced pressure. The residue was recrystallized from methanol-diethyl ether to afford the title compound as a yellow crystalline powder (melting point: 250.0–253.0° C.) (60.0 mg, yield: 57%).

$^1$H-NMR [CDCl$_3$](ammonium salt NH$^+$ protons were not observed) δ: 1.31(d, J=6.1 Hz, 12H), 2.86(s, 6H), 3.32(s, 6H), 3.80(s, 4H), 3.94(s, 12H), 4.46(qq, J=6.1, 6.1 Hz, 2H), 7.06(s, 4H), 7.68(dd, J=3.2, 9.3 Hz, 2H), 7.87(d, J=9.3 Hz, 2H), 8.74(d, J=3.2 Hz, 2H).

EXAMPLE 11

N,N'-Bis[2-[3,5-dimethoxy-4-(2,2,2-trifluoroethoxy)-phenyl]-5-pyridyl]-N,N'-dimethylethylenediamine dimethanesulfonate (80.0 mg, yield: 46%) from N,N'-bis(2-trifluoromethanesulfonyloxy-5-pyridyl)-N,N'-dimethylethylenediamine (128.0 mg, 0.240 mmol) synthesized in Reference Example 1 and 3,5-dimethoxy-4-(2,2,2-trifluoroethoxy)phenylboronic acid (146.0 mg, 0.530 mmol) synthesized as described in Reference Example 4.

To a solution of N,N'-bis[2-[3,5-dimethoxy-4-(2,2,2-trifluoroethoxy)phenyl]-5-pyridyl]-N,N'-dimethylethylenediamine (80.0 mg, 0.11 mmol) in methanol (2.0 mL) was added a 1.0 M aqueous methanesulfonic acid (0.22 mL, 0.22 mmol), and the reaction mixture was concentrated under reduced pressure. Ethanol (5.0 mL) was added to the residue, and the mixture was concentrated under reduced pressure. The residue was recrystallized from methanol-diethyl ether to afford the title compound as a yellow crystalline powder (melting point: 253.0–257.0° C. )(47.0 mg, yield: 22%).

$^1$H-NMR [DMSO, 120° C.](ammonium salt NH$^+$ protons were not observed) δ: 2.41(s, 6H), 3.04(s, 6H), 3.70(s, 4H), 3.88(s, 12H), 4.46(q, $^3J_{HF}$=9.0 Hz, 4H), 7.22(s, 4H), 7.32 (dd, J=3.2, 9.0 Hz, 2H), 7.80(d, J=9.0 Hz, 2H), 8.11 (d, J=3.2 Hz, 2H).

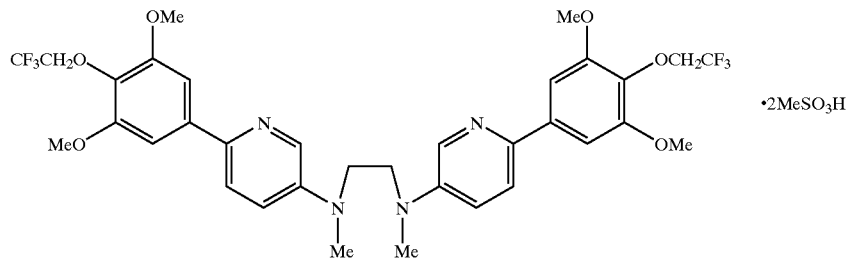

Following the procedure of Example 1, N,N'-bis[2-[3,5-dimethoxy-4-(2,2,2-trifluoroethoxy)phenyl]-5-pyridyl]-N,N'-dimethylethylenediamine was obtained as a colorless oil

EXAMPLE 12

N,N'-Bis[2-[4-(2-methoxyethoxy)-3,5-dimethoxyphenyl]-5-pyridyl]-N,N'-dimethylethylenediamine dimethanesulfonate

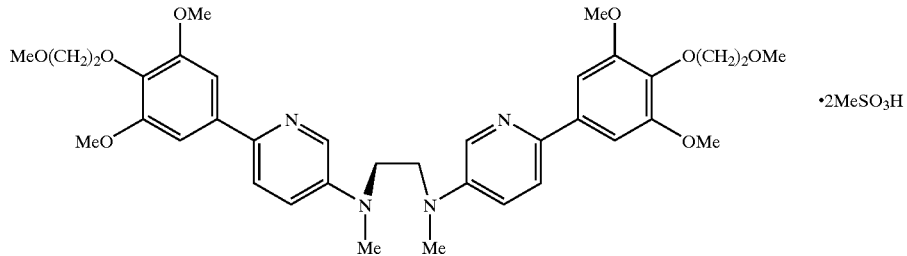

Following the procedure of Example 1, N,N'-bis[2-[4-(2-methoxyethoxy)-3,5-dimethoxyphenyl]-5-pyridyl]-N,N'-dimethylethylenediamine was obtained as a colorless oil (139.0 mg, yield: 75%) from N,N'-bis(2-trifluoromethanesulfonyloxy-5-pyridyl)-N,N'-dimethylethylenediamine (150.0 mg, 0.280 mmol) synthesized as described in Reference Example 1 and 4-(2-methoxyethoxy)-3,5-dimethoxyphenylboronic acid (158.0 mg, 0.620 mmol) synthesized as described in Reference Example 5.

To a solution of N,N'-bis[2-[4-(2-methoxyethoxy)-3,5-dimethoxyphenyl]-5-pyridyl]-N,N'-dimethylethylenediamine (139.0 mg, 0.21 mmol) in methanol (2.0 mL) was added a 1.0 M aqueous methanesulfonic acid solution (0.42 mL, 0.42 mmol) was added, and the reaction mixture was concentrated under reduced pressure. Ethanol (5.0 mL) was added to the residue, and the mixture was concentrated under reduced pressure. The residue was recrystallized from methanol-diethyl ether to afford the title compound as a yellow crystalline powder (melting point: 211.0–214.0° C.) (127.0 mg, yield: 71%).

$^1$H-NMR [CDCl$_3$](ammonium salt NH$^+$ protons were not observed) δ: 2.86(s, 6H), 3.32(s, 6H), 3.44(s, 6H), 3.69–3.74 (m, 4H), 3.80(s, 4H), 3.95(s, 12H), 4.16–4.21(m, 4H), 7.05(s, 4H), 7.69(dd, J=2.9, 9.3 Hz, 2H), 7.88(d, J=9.3 Hz, 2H), 8.73(d, J=2.9 Hz, 2H).

EXAMPLE 13

N,N'-Bis[2-[4-(2-hydroxyethoxy)-3,5-dimethoxyphenyl]-5-pyridyl]-N,N'-dimethylethylenediamine

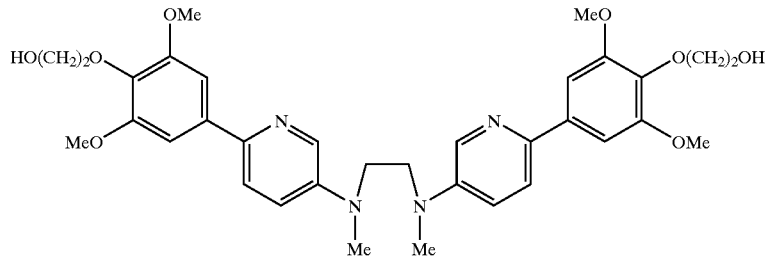

Following the procedure of Example 1, an oil (357.0 mg) containing N,N'-bis[2-[4-[2-(t-butyldimethylsiloxy)ethoxy]-3,5-dimethoxyphenyl]-5-pyridyl]-N,N'-dimethylethylenediamine was obtained from N,N'-bis(2-trifluoromethanesulfonyloxy-5-pyridyl)-N,N'-dimethylethylenediamine (162.0 mg, 0.300 mmol) synthesized as described in Reference Example 1 and 4-[2-(t-butyldimethylsiloxy)ethoxy]-3,5-dimethoxyphenylboronic acid (374.0 mg, 1.05 mmol) synthesized as described in Reference Example 6.

To a solution of the oil (357.0 mg) obtained by the preceding procedure in acetonitrile (19 mL) was added 46% hydrofluoric acid (1.0 mL). After stirring for 3 hours, a 1.0 M aqueous sodium hydroxide was added to the reaction mixture, and the resulting mixture was concentrated under reduced pressure to remove the organic solvent. The residue was extracted with chloroform, and the organic layer was dried over anhydrous sodium sulfate and concentrated under reduced pressure. The residue was purified by column chromatography on silica gel to obtain an oil. Methanol-chloroform-diethyl ether-hexane was added to the oil and the resulting precipitate was collected by filtration to afford the title compound as a yellow crystalline powder (melting point: 178.0–180.5° C.)[141.0 mg, yield: 74% based on N,N'-bis(2-trifluoromethanesulfonyloxy-5-pyridyl)-N,N'-dimethylethylenediamine].

$^1$H-NMR [CDCl$_3$] δ: 3.03(s, 6H), 3.53(br s, 2H), 3.67(s, 4H), 3.69–3.79(m, 4H), 3.96(s, 12H), 4.14–4.25(m, 4H), 6.99(dd, J=3.0, 8.8 Hz, 2H), 7.18(s, 4H), 7.55(d, J=8.8 Hz, 2H), 8.21(d, J=3.0 Hz, 2H).

EXAMPLE 14

N,N'-Bis[2-(4-hydroxy-3,5-dimethoxyphenyl)-5-pyridyl]-N,N'-dimethylethylenediamine dimethanesulfonate

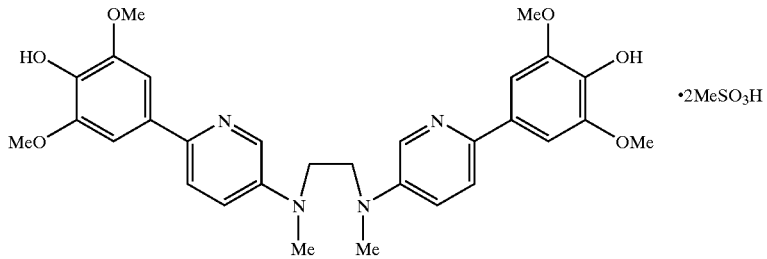

Following the procedure of Example 1, N,N'-bis[2-(4-benzyloxy-3,5-dimethoxyphenyl)-5-pyridyl]-N,N'-dimethylethylenediamine was obtained as a colorless viscous oil (64.0 mg, yield: 63%) from N,N'-bis(2-trifluoromethanesulfonyloxy-5-pyridyl)-N,N'-dimethylethylenediamine (75.0 mg, 0.140 mmol) synthesized as described in Reference Example 1 and 4-benzyloxy-3,5-dimethoxyphenylboronic acid (81.0 mg, 0.280 mmol).

To a solution of N,N'-bis[2-(4-benzyloxy-3,5-dimethoxyphenyl)-5-pyridyl]-N,N'-dimethylethylenediamine (64.0 mg, 0.090 mmol) in acetic acid (1.0 mL) was added 10% palladium on charcoal (43.0 mg). Under hydrogen, the mixture was stirred at 50° C. for 1 hour and 30 minutes. Insoluble materials were removed by filtration through Celite, and the filtrate was concentrated under reduced pressure. A solution of the residue in methanolchloroform (1:10) was washed with saturated aqueous sodium hydrogencarbonate and brine, dried over anhydrous sodium sulfate, and concentrated under reduced pressure. To a solution of the residue in methanol (2.0 mL) was added a 1.0 M aqueous methanesulfonic acid (0.20 mL, 0.20 mmol), and the reaction mixture was concentrated under reduced pressure. Ethanol (5.0 mL) was added to the residue, and the mixture was concentrated under reduced pressure. The residue was recrystallized from methanol-diethyl ether to afford the title compound as a yellow crystalline powder (melting point: ≧300.0°) (20.0 mg, yield: 31% based on N,N'-bis[2-(4-benzyloxy-3,5-dimethoxyphenyl)-5-pyridyl]-N,N'-dimethylethylenediamine).

$^1$H-NMR [DMSO, 120° C.](neither ammonium salt $NH^+$ protons nor phenol OH protons were observed) δ: 2.38(s, 6H), 3.04(s, 6H), 3.70(s, 4H), 3.85(s, 12H), 7.15(s, 4H), 7.43(dd, J=2.9, 9.0 Hz, 2H), 7.80(d, J=9.0 Hz, 2H), 7.99(d, J=2.9 Hz, 2H).

EXAMPLE 15

N,N'-Bis[2-(4-butyryloxy-3,5-dimethoxyphenyl)-5-pyridyl]-N,N'-dimethylethylenediamine dimethanesulfonate To a solution of N,N'-bis[2-(4-hydroxy-3,5-dimethoxyphenyl)-5-pyridyl]-N,N'-dimethylethylenediamine (74.0 mg, 0.135 mmol) synthesized as described in Example 14 in pyridine(1.5 mL)wasaddedbutyricanhydride(101.mg,0.640 mmol). After stirring at room temperature for 12 hours, the reaction mixture was concentrated under reduced pressure. Saturated aqueous sodium hydrogen carbonate was added to the residue, and the mixture was extracted with chloroform. The organic layer was washed with brine, dried over anhydrous sodium carbonate, and concentrated under reduced pressure. To a solution of the residue in methanol (2.0 mL) was added a 1.0 M aqueous methanesulfonic acid (0.27 mL, 0.27 mmol), and the reaction mixture was concentrated under reduced pressure. Ethanol (5.0 mL) was added to the residue, and the mixture was concentrated under reduced pressure. The residue was recrystallized from chloroform-diethyl ether to afford the title compound as a yellow crystalline powder (melting point: 196.0–200.0° C.)(70.0 mg, yield: 59%).

$^1$H-NMR ($CDCl_3$)(ammonium salt $NH^+$ protons were not observed) δ: 1.07(t, J=7.3 Hz, 6H), 1.82(tq, J=7.3, 7.3 Hz, 4H), 2.61(t, J=7.3 Hz, 4H), 2.85(s, 6H), 3.32(s, 6H), 3.81(s, 4H), 3.92(s, 12H), 7.08(s, 4H), 7.70(dd, J=2.9, 9.3 Hz, 2H), 7.89(d, J=9.3 Hz, 2H), 8.72(d, J=2.9 Hz, 2H).

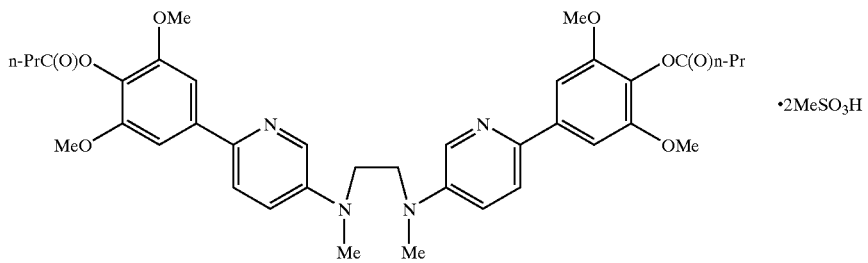

EXAMPLE 16

N,N'-Bis[2-(3-methoxy-4,5-methylenedioxyphenyl)-5-pyridyl]-N,N'-dimethylethylenediamine dimethanesulfonate

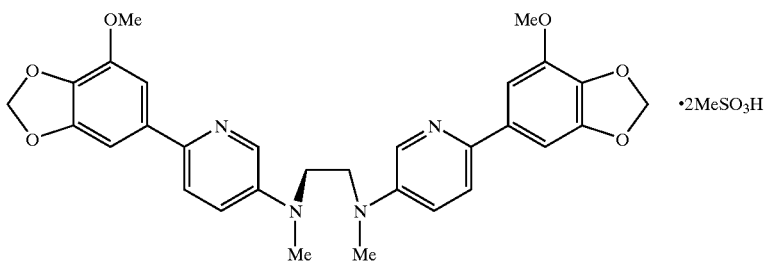

Following the procedure of Example 1, N,N'-bis[2-(3-methoxy-4,5-methylenedioxyphenyl)-5-pyridyl]-N,N'-dimethylethylenediamine was obtained as a colorless oil (109.0 mg, yield: 72%) from N,N'-bis(2-trifluoromethanesulfonyloxy-5-pyridyl)-N,N'-dimethylethylenediamine (150.0 mg, 0.280 mmol) synthesized as described in Reference Example 1 and 3-methoxy-4,5-methylenedioxyphenylboronic acid (115.0 mg, 0.590 mmol).

To a solution of N,N'-bis[2-(3-methoxy-4,5-methylenedioxyphenyl)-5-pyridyl]-N,N'-dimethylethylenediamine (109.0 mg, 0.200 mmol) in methanol (3.0 mL) was added a 1.0 M aqueous solution of methanesulfonic acid (0.40 mL, 0.40 mmol), and the reaction mixture was concentrated under reduced pressure. Ethanol (5.0 mL) was added to the residue, and the mixture was concentrated under reduced pressure. The residue was recrystallized from methanol-diethyl ether to yield the title compound as a yellow crystalline powder (melting point: 275.0°–276.0° C.)(109.0 mg, yield: 79%).

$^1$H-NMR [CD$_3$OD-CDCl$_3$(1:10)](ammonium salt NH$^+$ protons were not observed) δ: 2.84(s, 6H), 3.20(s, 6H), 3.85(s, 4H), 4.02(s, 6H), 6.09(s, 4H), 6.93(d, J=1.7 Hz, 2H), 7.06(d, J=1.7 Hz, 2H), 7.74(dd, J=2.9, 9.5 Hz, 2H), 7.82(d, J=9.5 Hz, 2H), 8.34(d, J=2.9 Hz, 2H).

EXAMPLE 17

N,N'-Bis[2-(3,4,5-triethoxyphenyl)-5-pyridyl]-N,N'-dimethylethylenediamine dimethanesulfonate

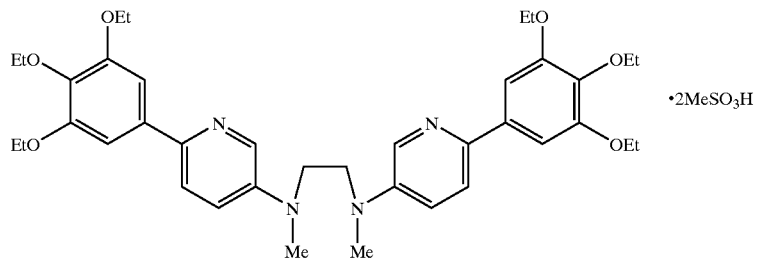

Following the procedure of Example 1, N,N'-bis[2-(3,4,5-triethoxyphenyl)-5-pyridyl]-N,N'-dimethylethylenediamine was obtained as a pale yellow oil (123.0 mg, yield: 93%) from N,N'-bis(2-trifluoromethanesulfonyloxy-5-pyridyl)-N,N'-dimethylethylenediamine (108.0 mg, 0.200 mmol) synthesized as described in Reference Example 1 and 3,4,5-triethoxyphenylboronic acid (122.0 mg, 0.480 mmol).

To a solution of N,N'-bis[2-(3,4,5-triethoxyphenyl)-5-pyridyl]-N,N'-dimethylethylenediamine (123.0 mg, 0.186 mmol) in methanol (3.0 mL) was added a 1.0 M solution of methanesulfonic acid in methanol (0.38 mL, 0.38 mmol), and the reaction mixture was concentrated under reduced pressure. Chloroform-diethyl ether was added to the residue and the resulting precipitate was collected by filtration to afford the title compound as a yellow crystalline powder [melting point: 237.0° C. (decomposed)](110.0 mg, yield: 70%).

$^1$H-NMR [CDCl$_3$](ammonium salt NH$^+$ protons were not observed) δ: 1.37(t, J=7.0 Hz, 6H), 1.46(t, J=6.8 Hz, 12H), 2.87(s, 6H), 3.31(s, 6H), 3.79(s, 4H), 4.12(q, J=7.0 Hz, 4H), 4.17(q, J=6.8 Hz, 8H), 7.01(s, 4H), 7.67(br d, J=9.0 Hz, 2H), 7.82(d, J=9.0 Hz, 2H), 8.69(br s, 2H).

EXAMPLE 18

N,N'-Bis[2-(3,5-dimethoxy-4-methylthiophenyl)-5-pyridyl]-N,N'-dimethylethylenediamine dimethanesulfonate

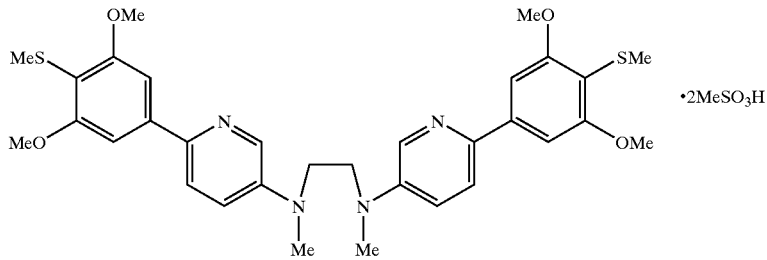

Following the procedure of Example 1, N,N'-bis[2-(3,5-dimethoxy-4-methylthiophenyl)-5-pyridyl]-N,N'-dimethylethylenediamine was obtained as a colorless viscous oil (61.0 mg, yield: 80%) from N,N'-bis(2-trifluoromethane-sulfonyloxy-5-pyridyl)-N,N'-dimethylethylenediamine (70.0 mg, 0.130 mmol) synthesized as described in Reference Example 1 and 3,5-dimethoxy-4-methylthiophenylboronic acid (60.0 mg, 0.260 mmol).

To a solution of N,N'-bis[2-(3,5-dimethoxy-4-methylthiophenyl)-5-pyridyl]-N,N'-dimethylethylenediamine (61.0 mg, 0.100 mmol) in methanol (2.0 mL) was added a 1.0 M aqueous solution of methanesulfonic acid (0.20 mL, 0.20 mmol), and the reaction mixture was concentrated under reduced pressure. Ethanol (5.0 mL) was added to the residue, and the mixture was concentrated under reduced pressure. The residue was recrystallized from methanol-diethyl ether to yield the title compound as a yellow crystalline powder (melting point: 242.0–244.0° C.)(41.0 mg, yield: 51%).

$^1$H-NMR (CDCl$_3$)(ammonium salt NH$^+$ protons were not observed) δ: 2.42(s, 6H), 2.86(s, 6H), 3.34(s, 6H), 3.82(s, 4H), 4.00(s, 12H), 7.01(s, 4H), 7.72(dd, J=2.9, 9.3 Hz, 2H),7.93(d, J=9.3 Hz, 2H), 8.79(d, J=2.9 Hz, 2H).

EXAMPLE 19

N,N'-Bis[2-[3,5-dimethoxy-4-(1-pyrrolidinyl)phenyl]-5-pyridyl]-N,N'-dimethylethylenediamine

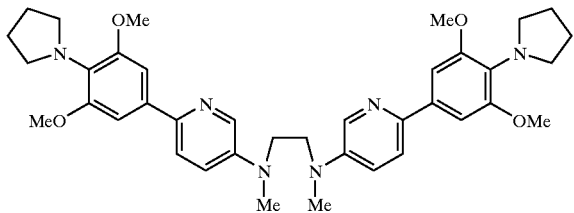

Following the procedure as described in Example 1, an oil was obtained from N,N'-bis(2-trifluoromethanesulfonyloxy-5-pyridyl)-N,N'-dimethylethylenediamine (120.0 mg, 0.220 mmol) synthesized as described in Reference Example 1 and (1-bromo-)3,5-dimethoxy-4-(1-pyrrolidinyl)benzene (138.0 mg, 0.550 mmol). Methanol was added to the oil and the resulting precipitate was collected by filtration to yield the title compound as a pale brown crystalline powder (melting point: 221.0–225.0° C. )(81.0 mg, yield: 56%).

$^1$H-NMR (CDCl$_3$) δ: 1.89–1.97(m, 8H), 3.01(s, 6H), 3.28–3.37(m, 8H), 3.65(s, 4H), 3.91(s, 12H), 6.97(dd, J=2.9, 8.8 Hz, 2H), 7.14(s, 4H), 7.54(d, J=8.8 Hz, 2H), 8.21(d, J=2.9 Hz, 2H).

EXAMPLE 20

N,N'-Bis[2-(4-dimethylamino-3,5-dimethoxyphenyl)-5-pyridyl]-N,N'-dimethylethylenediamine

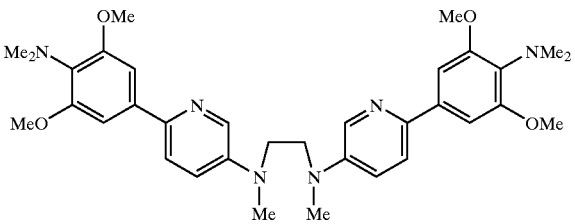

Following the procedure of Example 1, an oil was obtained from N,N'-bis(2-trifluoromethanesulfonyloxy-5-pyridyl)-N,N'-dimethylethylenediamine (129.0 mg, 0.240 mmol) synthesized as described in Reference Example 1 and 4-dimethylamino-3,5-dimethoxyphenylboronic acid (135.0 mg, 0.600 mmol). Methanol was added to the oil and the resulting precipitate was collected by filtration to yield the title compound as a pale brown crystalline powder (melting point: 194.0–196.0°)(84.0 mg, yield: 58%).

$^1$H-NMR (CDCl$_3$) δ 2.85(s, 12H), 3.02(s, 6H), 3.66(s, 4H), 3.93(s, 12H), 6.98(dd, J=2.9, 9.0 Hz, 2H), 7.12(s, 4H), 7.55(d, J=9.0 Hz, 2H), 8.22(d,J=2.9 Hz, 2H).

EXAMPLE 21

N,N'-Bis[2-(3,5-dimethoxy-4-methylphenyl)-5-pyridyl]-N,N'-dimethylethylenediamine dimethanesulfonate

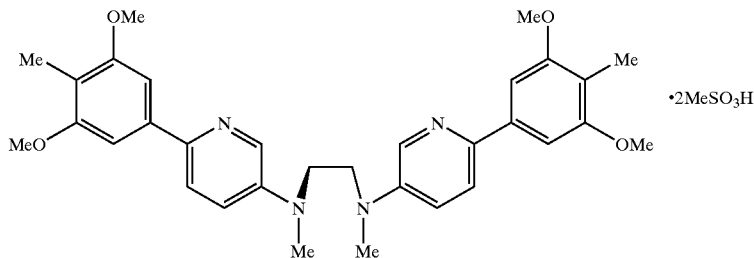

Following the procedure of Example 7, N,N'-bis[2-(3,5-dimethoxy-4-methylphenyl)-5-pyridyl]-N,N'-dimethylethylenediamine was obtained as a colorless oil (37.0 mg, yield: 40%) from 5-chloro-2-(3,5-dimethoxy-4-methylphenyl)pyridine (99.0 mg, 0.370 mmol) synthesized by a similar procedure as described in Reference Example 2.

To a solution of N,N'-bis[2-(3,5-dimethoxy-4-methylphenyl)-5-pyridyl]-N,N'-dimethylethylenediamine (37.0 mg, 0.070 mmol) in methanol (2.0 mL) was added a 1.0 M aqueous methanesulfonic acid (0.15 mL, 0.15 mmol), and the reaction mixture was concentrated under reduced pressure. Ethanol (5.0 mL) was added to the residue, and the mixture was concentrated under reduced pressure. The residue was recrystallized from methanol-chloroform to yield the title compound as a yellow crystalline powder (melting point: 272.0–274.0° C.)(22.0 mg, yield: 44%).

$^1$H-NMR [$CD_3OD$-$CDCl_3$(1:10)](ammonium salt $NH^+$ protons were not observed) δ: 2.12(s, 6H), 2.83(s, 6H), 3.24(s, 6H), 3.85(s, 4H), 3.91(s, 12H), 7.23(s, 4H), 7.76(dd, J=2.9, 9.3 Hz, 2H), 7.94(d, J=9.3 Hz, 2H), 8.45(d, J=2.9 Hz, 2H).

EXAMPLE 22

N,N'-Bis[2-(4-fluoro-3,5-dimethoxyphenyl)-5-pyridyl]-N,N'-dimethyletylenediamine dimethanesulfonate

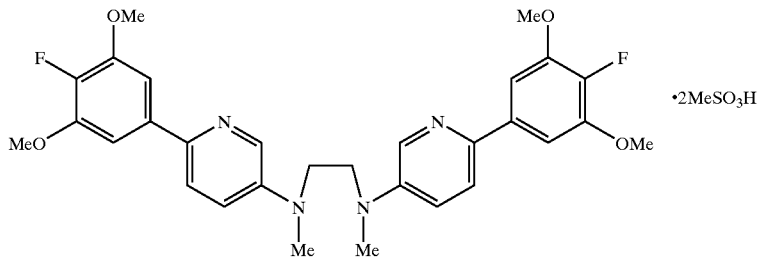

Following the procedure of Example 1, an oil was obtained from N,N'-bis(2-trifluoromethanesulfonyloxy-5-pyridyl)-N,N'-dimethylethylenediamine (150.0 mg, 0.280 5 mmol) synthesized as described in Reference Example 1 and 4-fluoro-3,5-dimethoxyphenylboronic acid (167.0 mg, 0.840 mmol). Hexane was added to the oil and the resulting precipitate was collected by filtration to provide N,N'-bis[2-(4-fluoro-3,5-dimethoxyphenyl)-5-pyridyl]-N,N'-dimethylethylenediamine as a yellow crystalline powder (160.0 mg; quantitative).

To a solution of N,N'-bis[2-(4-fluoro-3,5-dimethoxyphenyl)-5-pyridyl]-N,N'-dimethylethylenediamine (150.0 mg, 0.270 mmol) in chloroform (30 mL) was added a 1.0 M aqueous methanesulfonic acid solution (0.60 mL, 0.60 mmol), and the reaction mixture was concentrated under reduced pressure. Ethanol (5.0 mL) was added to the residue, and the mixture was concentrated under reduced pressure. Diethyl ether was added to the residue and the resulting precipitate was collected by filtration to yield the title compound as a yellow crystalline powder (melting point:≧300.0° C.)(1 81.0 mg, yield: 90%).

$^1$H-NMR (DMSO-$d_6$)(ammonium salt $NH^+$ protons were not observed) δ: 2.33(s, 6H), 3.03(s, 6H), 3.77(br s, 4H), 3.89(s, 12H), 7.25(d, $^4J_{HF}$=7.0 Hz, 4H), 7.50–7.59(m, 2H), 7.99–8.06(m, 4H).

EXAMPLE 23

N,N'-Bis[2-(4-chloro-3,5-dimethoxyphenyl)-5-pyridyl]-N,N'-dimethylethylenediamine dimethanesulfonate

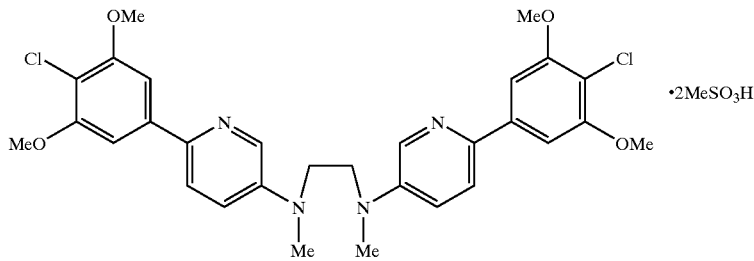

Following the procedure of Example 1, N,N'-bis[2-(4-chloro-3,5-dimethoxyphenyl)-5-pyridyl]-N,N'-dimethylethylenediamine was obtained as a pale yellow amorphous powder (101.0 mg, yield: 86%) from N,N'-bis(2-trifluoromethanesulfonyloxy-5-pyridyl)-N,N'-dimethylethylenediamine (108.0 mg, 0.200 mmol) synthesized as described in Reference Example 1 and 4-chloro-3,5-dimethoxyphenylboronic acid (95.0 mg, 0.440 mmol).

To a solution of N,N'-bis[2-(4-chloro-3,5-dimethoxyphenyl)-5-pyridyl]-N,N'-dimethylethylenediamine (78.0 mg, 0.130 mmol) in methanol-chloroform (1:2, 50 mL) was added a 1.0 M aqueous methanesulfonic acid solution (0.27 mL, 0.27 mmol), and the reaction mixture was concentrated under reduced pressure. Ethanol (5.0 mL) was added to the residue, and the mixture was concentrated under reduced pressure. The residue was recrystallized from methanol-chloroform-diethyl ether to yield the title compound was obtained as a yellow crystalline powder (melting point: 280.0–285.0° C.) (83.0 mg, yield: 80%).

$^1$H-NMR (DMSO-$d_6$, 120° C.) (ammonium salt NH$^+$ protons were not observed) δ: 2.45(s, 6H), 3.05(s, 6H), 3.72(s, 4H), 3.91(s, 12H), 7.26(s, 4H), 7.37(dd, J=3.1, 9.0 Hz, 2H), 7.87(d, J=9.0 Hz, 2H), 814(d,J=3.1 Hz, 2H).

EXAMPLE 24

N,N'-Bis[2-(4-cyano-3,5-dimethoxyphenyl)-5-pyridyl]-N,N'-dimethylethylenediamine dimethanesulfonate

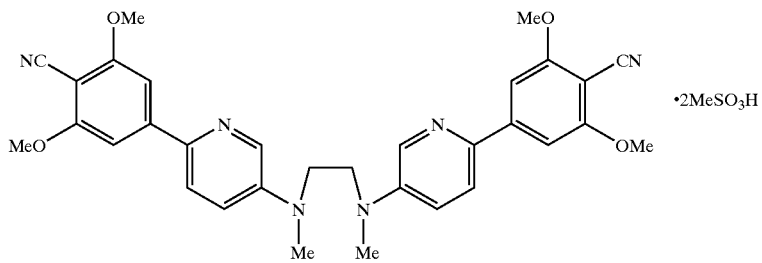

Following the procedure of Example 1, N,N'-bis[2-(4-cyano-3,5-dimethoxyphenyl)-5-pyridyl]-N,N'-dimethylethylenediamine was obtained as a colorless oil (125.0 mg, yield: 79%) from N,N'-bis(2-trifluoromethanesulfonyloxy-5-pyridyl)-N,N'-dimethylethylenediamine (150.0 mg, 0.280 mmol) synthesized as described in Reference Example 1 and 4-cyano-3,5-dimethoxyphenylboronic acid (145.0 mg, 0.700 mmol).

To a solution of N,N'-bis[2-(4-cyano-3,5-dimethoxyphenyl)-5-pyridyl]-N,N'-dimethylethylenediamine (125.0 mg, 0.220 mmol) in methanol (2.0 mL) was added a 1.0 M aqueous methanesulfonic acid solution (0.44 mL, 0.44 mmol), and the reaction mixture was concentrated under reduced pressure. Ethanol (5.0 mL) was added to the residue, and the mixture was concentrated under reduced pressure. Methanol (2.5 mL) was added to the residue, and the resulting suspension was stirred in a bath maintained at 70° C. After cooling, the resulting precipitate was collected by filtration to afford the title compound as a yellow crystalline powder (melting point:≧300.0° C.)(72.0 mg, yield: 43%).

$^1$H-NMR [CD$_3$OD-CDCl$_3$(1:10)](ammonium salt NH$^+$ protons were not observed) δ: 2.35(s, 6H), 3.04(s, 6H), 3.77(s, 4H), 3.97(s, 12H), 7.32(s, 4H), 7.28–7.34(m, 2H), 8.06(d, J=9.0 Hz, 2H), 8.19(d, J=3.2 Hz, 2H).

EXAMPLE 25

N,N'-Bis[2-[3,5-dimethoxy-4-(N-methoxy-N-methylcarbamoyl)phenyl]-5-pyridyl]-N,N'-dimethylethylenediamine

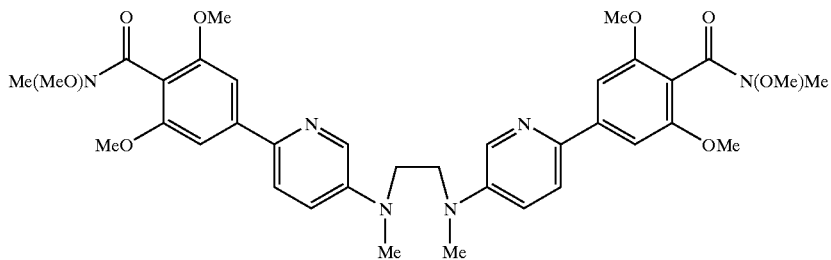

Following the procedure of Example 1, an oil was obtained from N,N'-bis(2-trifluoromethanesulfonyloxy-5-pyridyl)-N,N'-dimethylethylenediamine (76.0 mg, 0.140 mmol) synthesized as described in Reference Example 1 and 3,5-dimethoxy-4-(N-methoxy-N-methylcarbamoyl)phenylboronic acid (91.0 mg, 0.340 mmol) synthesized in Reference Example 7. Chloroform-hexane was added to the oil and the resulting precipitate was collected by filtration to yield the title compound as a yellow crystalline powder (melting point: 217.0–220.0° C.)(34.0 mg, yield: 36%).

$^1$H-NMR (CDCl$_3$)(mixture of geometrical isomers of the amide, data for the major isomer) δ: 3.04(s, 6H), 3.40(s, 6H), 3.51(s, 6H), 3.68(s, 4H), 3.91(s, 12H), 7.01(dd, J=2.5, 8.6 Hz, 2H), 7.15(s, 4H), 7.59(d, J=8.6 Hz, 2H), 8.23(d, J=2.5 Hz, 2H).

EXAMPLE 26

N,N'-Bis[2-(4-t-butoxycarbonyl-3,5-dimethoxyphenyl)-5-pyridyl]-N,N'-dimethylethylenediamine dimethylethylenediamine

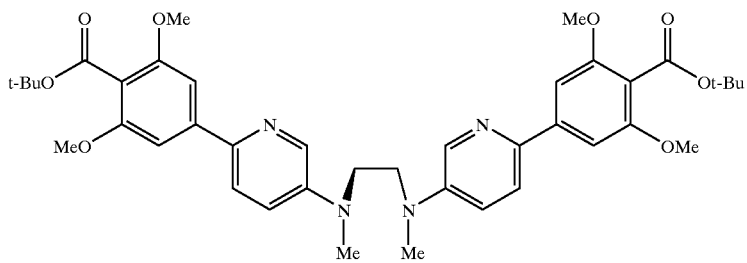

Following the procedure of Example 1, crude crystals were obtained from N,N'-bis(2-trifluoromethanesulfonyloxy-5-pyridyl)-N,N'-dimethylethylenediamine (167.0 mg, 0.300 mmol) synthesized as described in Reference Example 1 and 4-t-butoxycarbonyl-3,5-dimethoxyphenylboronic acid (187.0 mg, 0.660 mmol). The crude crystals were recrystallized from methylene chloride-diethyl ether-hexane to yield the title compound as a colorless crystalline powder (melting point: 211.0–213.0° C.)(195.0 mg, yield: 90%).

$^1$H-NMR (CDCl$_3$) δ: 1.59(s, 18H), 3.02(s, 6H), 3.66(s, 4H), 3.90(s, 12H), 6.98(dd, J=3.1, 8.7 Hz, 2H), 7.11 (s, 4H), 7.55(d, J=8.7 Hz, 2H), 8.22(d, J=3.1 Hz, 2H).

EXAMPLE 27

N,N'-Bis[2-(4-carboxy-3,5-dimethoxyphenyl)-5-pyridyl]-N,N'-dimethylethylenediamine ditrifluoroacetate

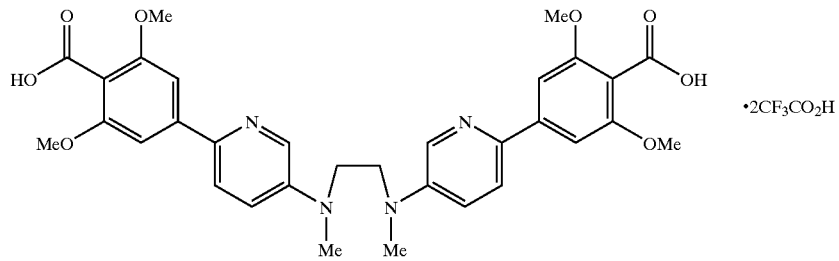

To a solution of N,N'-bis[2-(4-t-butoxycarbonyl-3,5-dimethoxyphenyl)-5-pyridyl]-N,N'-dimethylethylenediamine (72.0 mg, 0.100 mmol) synthesized as described in Example 26 in methylene chloride (1.0 mL) was added trifluoroacetic acid (1.0 mL), and the resulting mixture was stirred for 3 hours. Diethyl ether was added to the ice-cold reaction mixture and the resulting precipitate was collected by filtration to yield the title compound as a pale yellow crystalline powder [melting point: 235.0° C. (decomposed)](72.0 mg, yield: 86%).

$^1$H-NMR (DMSO-d$_6$, 120° C.) (neither ammonium salt NH$^+$ protons nor carboxylic acid CO$_2$H protons were observed) δ: 3.03(s, 6H), 3.68(s, 4H), 3.84(s, 12H), 7.19(dd, J=3.1, 8.7 Hz, 2H), 7.22(s, 4H), 7.76(d, J=8.7 Hz, 2H), 8.18(d, J=3.1 Hz, 2H).

EXAMPLE 28

N,N'-Bis[2-(4-ethoxycarboxy-3,5-dimethoxyphenyl)-5-pyridyl]-N,N'-dimethylethylenediamine

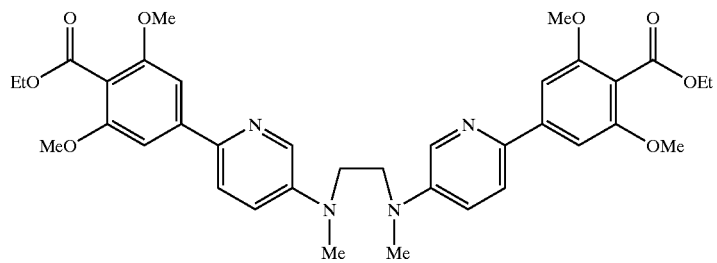

To a solution of N,N'-bis[2-(4-carboxy-3,5-dimethoxyphenyl)-5-pyridyl]-N,N'-dimethylethylenediamine ditrifluoroacetate (42.0 mg, 0.050 mmol) synthesized as described in Example 27 in methylene chloride (5.0 mL) were added dimethylformamide (0.1 mL, 1.29 mmol) and oxalyl chloride (0.21 mL, 2.5 mmol). After the resulting mixture was stirred at room temperature for 30 minutes, ethanol (2.0 mL, 35 mmol) and N,N-diisopropylethyl amine (0.51 mL, 3.0 mmol) were added. The reaction mixture was stirred for 1 hour and concentrated under reduced pressure. The residue was purified by column chromatography on silica gel and crude crystals were obtained. The crude crystals were recrystallized from methylene chloride-diethyl ether-hexane to yield the title compound as a pale yellow crystalline powder (melting point: 206.0–208.0° C.)(30.0 mg, yield: 86%).

$^1$H-NMR (CDCl$_3$) δ: 1.38(t, J=7.0 Hz, 6H), 3.03(s, 6H), 3.67(s, 4H), 3.91(s, 12H), 4.40(q, J=7.0 Hz, 4H), 7.00(dd, J=2.9, 8.7 Hz, 2H), 7.14(s, 4H), 7.57(d, J=8.7 Hz, 2H), 8.23(d, J=2.9 Hz, 2H).

EXAMPLE 29

N,N'-Bis[2-(4-acetyl-3,5-dimethoxyphenyl)-5-Pyridyl]-N,N'-dimethylethylenediamine dimethanesulfonate

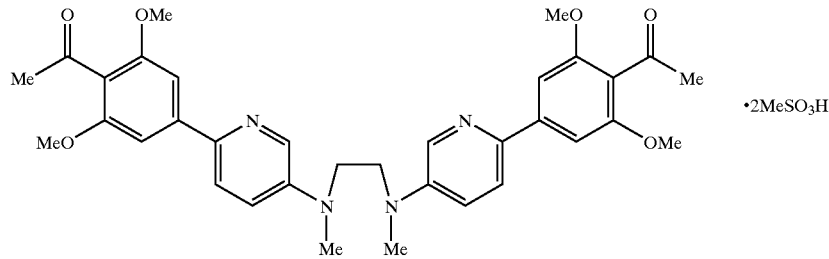

Under nitrogen, to a solution of (4-acetyl-3,5-dimethoxyphenyl)trimethyltin (235.0 mg, 0.760 mmol) synthesized as described in Reference Example 8 in toluene (10 mL) were added crude N,N'-bis(2-chloro-5-pyridyl)-N,N'-dimethylethylenediamine(78.0 mg, approx. 0.25 mmol) synthesized as described in Reference Example 9 and tetrakis(triphenylphosphine)palladium (116.0 mg, 0.100 mmol). After stirring at 130° C. for 22 hours, a saturated aqueous potassium fluoride was added to the reaction mixture and the mixture was stirred for 1 hour. Insoluble materials were removed by filtration through Celite. The residue was washed with chloroform, and the aqueous layer of the filtrate was extracted with chloroform. The washing and the organic layer of the filtrate were combined, dried over anhydrous sodium sulfate, and concentrated under reduced pressure. The residue was purified by column chromatography on silica gel to yield N,N'-bis[2-(4-acetyl-3,5-dimethoxyphenyl)-5-pyridyl]-N,N'-dimethylethylenediamine as a pale yellow crystalline powder [41.4 mg, yield: 23% based on N,N'-bis(2-hydroxy-5-pyridyl)-N,N'-dimethylethylenediamine ditrifluoroacetate].

To a solution of N,N'-bis[2-(4-acetyl-3,5-dimethoxyphenyl)-5-pyridyl]-N,N'-dimethylethylenediamine (76.4 mg, 0.128 mmol) in chloroform (5.0 mL) was added a 1.0 M solution of methanesulfonic acid in methanol (0.32 mL, 0.32 mmol), and the reaction mixture was concentrated under reduced pressure. Chloroform-diethyl ether was added to the residue and the resulting precipitate was collected by filtration to yield the title compound as a yellow crystalline powder (melting point: 261.0–265.5° C.)(75.1 mg, yield: 74%).

$^1$H-NMR (CDCl$_3$)(ammonium salt NH$^+$ protons were not observed) δ: 2.49(s, 6H), 2.86(s, 6H), 3.35(s, 6H), 3.80(s, 4H), 3.92(s, 12H), 7.03(s, 12H), 7.72(br d, J=9.2 Hz, 2H), 7.94(d, J=9.2 Hz, 2H), 8.82(br s, 2H).

EXAMPLE 30

1,4-Bis[2-(3,4,5-trimethoxyphenyl)-5-pyridyl]hexahydro-1,4-diazepine dimethanesulfonate

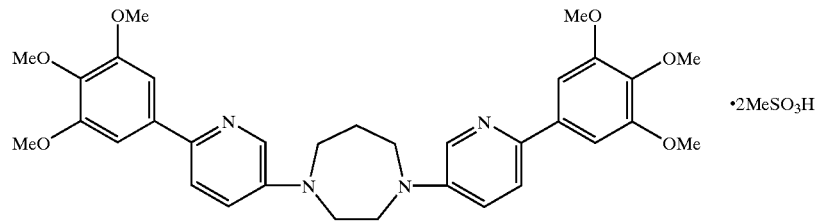

Following the procedure of Example 7, 1,4-bis[2-(3,4,5-trimethoxyphenyl)-5-pyridyl]hexahydro-1,4-diazepine was obtained as a yellow amorphous powder (174.0 mg, yield: 59%) from 5-chloro-2-(3,4,5-trimethoxypheny)pyridine (335.0 mg, 1.20 mmol) synthesized as described in Reference Example 2 and hexahydro-1,4-diazepine (50.0 mg, 0.500 mmol).

To a solution of 1,4-bis[2-(3,4,5-trimethoxyphenyl)-5-pyridyl]hexahydro-1,4-diazepine (88.0 mg, 0.150 mmol) in methanol-methylene chloride (1:1, 4.0 mL) was added a 1.0 M aqueous methanesulfonic acid solution (0.30 mL, 0.30 mmol), and the reaction mixture was concentrated under reduced pressure. Ethanol (5.0 mL) was added to the residue, and the mixture was concentrated under reduced pressure. The residue was recrystallized from methanol-methylene chloride-diethyl ether to yield the title compound as yellow prisms (melting point: 246.0–248.0° C.)(93.0 mg, yield: 79%).

$^1$H-NMR (DMSO-d$_6$, 120° C. ) (ammonium salt NH$^+$ protons were not observed) δ: 2.04(tt, J=5.8, 5.8 Hz, 2H), 2.42(s, 6H), 3.64(dd, J=5.8, 5.8 Hz, 4H), 3.75(s, 6H), 3.83(s, 4H), 3.84(s, 12H), 7.14(s, 4H), 7.52(dd, J=3.1, 9.0 Hz, 2H), 7.82(d, J=9.0 Hz, 2H), 8.14(d, J=3.1 Hz, 2H).

EXAMPLE 31

1,4-Bis[2-(3,4,5-trimethoxyphenyl)-5-pyridyl]piperazine dimethanesulfonate

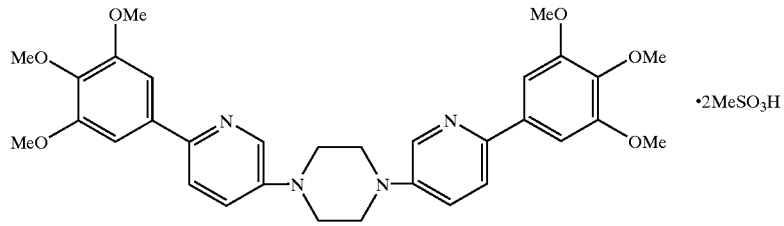

Following the procedure of Example 7, 1,4-bis[2-(3,4,5-trimethoxyphenyl)-5-pyridyl]piperazine was obtained as pale yellow needles (174.0 mg, yield: 61%) from 5-chloro-2-(3,4,5-trimethoxypheny)pyridine (335.0 mg, 1.20 mmol) synthesized as described in Reference Example 2 and piperazine (43.0 mg, 0.500 mmol).

To a solution of 1,4-bis[2-(3,4,5-trimethoxyphenyl)-5-pyridyl]piperazine (143.0 mg, 0.250 mmol) in methanol-methylene chloride (1:2, 6.0 mL) was added a 1.0 M aqueous methanesulfonic acid solution (0.50 mL, 0.50 mmol), and the reaction mixture was concentrated under reduced pressure. Ethanol (5.0 mL) was added to the residue, and the mixture was concentrated under reduced pressure. The residue was recrystallized from methanol-chloroform-diethyl ether to yield the title compound as yellow needles [melting point: 262.0° C. (decomposed)] (171.0 mg, yield: 89%).

$^1$H-NMR (CDCl$_3$) (data for the free base of the title compound) δ: 3.46(s, 8H), 3.89(s, 6H), 3.96(s, 12H), 7.19(s, 4H), 7.32(dd, J=3.1, 8.7 Hz, 2H), 7.63(d, J=8.7 Hz, 2H), 8.43(d, J=3.1 Hz, 2H).

EXAMPLE 32

1,3-Bis[4-[2-(3,4,5-trimethoxyphenyl)-5-pyridyl]-1-piperazinyl]propane tetrahydrochloride Following the procedure of Example 7, 1,3-bis[4-[2-(3,4,5-trimethoxyphenyl)-5-pyridyl]-1-piperazinyl]propane was obtained as a pale yellow oil (44.0 mg, yield: 25%) from 5-chloro-2-(3,4,5-trimethoxypheny)pyridine (166.0 mg, 0.600 mmol) synthesized in Reference Example 2 and 1,3-bis(1-piperazinyl)propane (90.0 mg, 0.250 mmol).

To a solution of 1,3-bis[4-[2-(3,4,5-trimethoxyphenyl)-5-pyridyl]-1-piperazinyl]propane (44.0 mg, 0.060 mmol) in methanol-methylene chloride (1:2, 3.0 mL) was added 1.0 M hydrochloric acid solution (0.30 mL, 0.30 mmol), and the reaction mixture was concentrated under reduced pressure. Ethanol (5.0 mL) was added to the residue, and the mixture was concentrated under reduced pressure. The residue was recrystallized from methanol-diethyl ether to yield the title compound as a yellow crystalline powder [melting point: 264.0° C. (decomposed)](35.0 mg, yield: 69%).

$^1$H-NMR (CDCl$_3$)(ammonium salt NH$^+$ protons were not observed) δ: 1.72–1.87(m, 2H), 2.46–2.56(m, 4H), 2.61–2.71(m, 8H), 3.24–3.35(m, 8H), 3.88(s, 6H), 3.95(s, 12H), 7.16(s, 4H), 7.24(dd, J=2.9, 8.7 Hz, 2H), 7.58(d, J=8.7 Hz, 2H), 8.37(d, J=2.9 Hz, 2H).

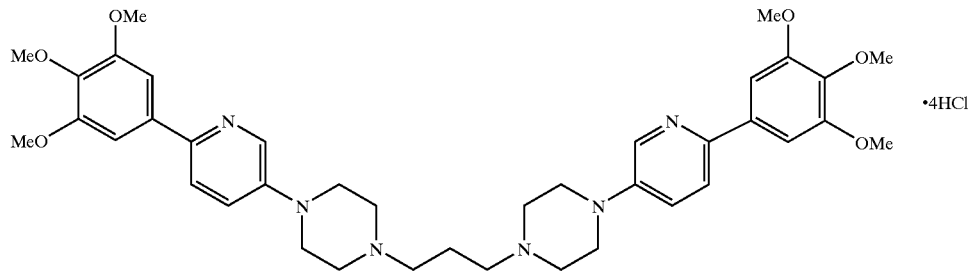

EXAMPLE 33

N,N'-Bis[2-(3,4,5-trimethoxyphenyl)-5-pyridyl]ethylenediamine

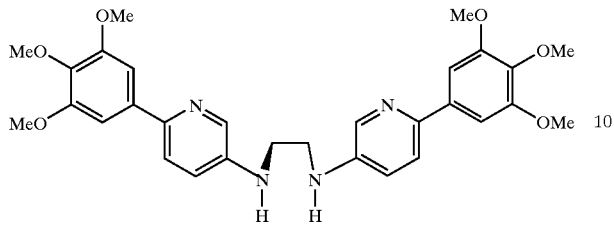

Following the procedure of Example 7, the title compound was obtained as a pale yellow amorphous powder (21.0 mg, yield: 7%) from 5-chloro-2-(3,4,5-trimethoxypheny)pyridine (335.0 mg, 1.20 mmol) synthesized as described in Reference Example 2 and ethylenediamine (30.0 mg, 0.500 mmol).

$^1$H-NMR (CDCl$_3$) δ: 3.50(s, 4H), 3.88(s, 6H), 3.95(s, 12H), 4.01–4.09(br s, 2H), 7.01(dd, J=2.9, 8.5 Hz, 2H), 7.14(s, 4H), 7.53(d, J=8.5 Hz, 2H), 8.16(d, J=2.9 Hz, 2H).

EXAMPLE 34 cis-N,N'-Bis[2-(3,4,5-trimethoxyphenyl)-5-pyridyl]-1,2-cyclohexanediamine

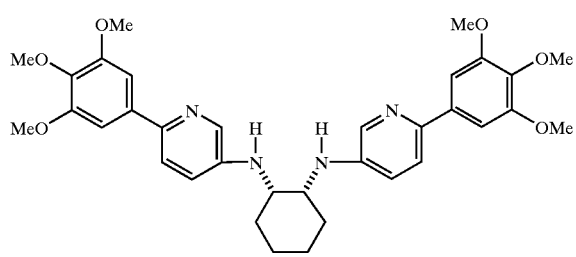

Following the procedure of Example 7, the title compound was obtained as a pale yellow amorphous powder (37.0 mg, yield: 12%) from 5-chloro-2-(3,4,5-trimethoxypheny)pyridine (166.0 mg, 0.600 mmol) synthesized as described in Reference Example 2 and cis-1,2-cyclohexanediamine (24.0 mg, 0.200 mmol).

$^1$H-NMR (CDCl$_3$) δ: 1.53–1.72(m, 6H), 1.79–1.91(m, 2H), 3.75–3.85(m, 2H), 3.88(s, 6H), 3.94(s, 12H), 3.94–4.02 (m, 2H), 6.96(dd, J=2.6, 8.5 Hz, 2H), 7.13(s, 4H), 7.48(d, J=8.5 Hz, 2H), 8.13(d, J=2.6 Hz, 2H).

EXAMPLE 35 trans-N,N'-Bis[2-(3,4,5-trimethoxyphenyl)-5-pyridyl]-1,4-cyclohexanediamine

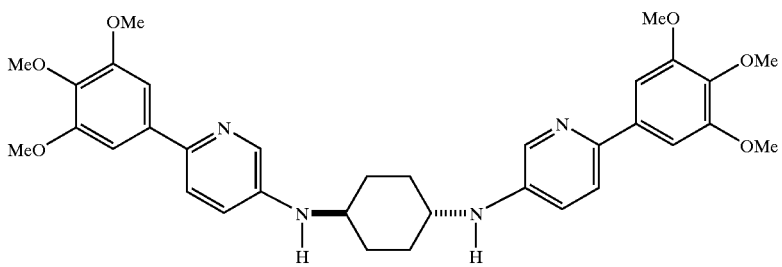

Following the procedure of Example 7, crude crystals was obtained (66.0 mg, yield: 21%) from 5-chloro-2-(3,4,5-trimethoxypheny)pyridine (335.0 mg, 1.20 mmol) synthesized as described in Reference Example 2 and trans-1,4-cyclohexanediamine (57.0 mg, 0.500 mmol). The crude crystals were recrystallized from chloroform-diethyl ether-hexane to yield the title compound as a pale brown crystalline powder (melting point: 264.0–267.0° C.) (27.0 mg, yield: 9%).

$^1$H-NMR [CD$_3$OD-CDCl$_3$(1 :10)] (amine NH protons were not observed) δ: 1.34–1.46(m, 4H), 2.19–2.31(m, 4H), 3.27–3.35(m, 2H), 3.87(s, 6H), 3.95(s, 12H), 7.00(dd, J=2.9, 8.7 Hz, 2H), 7.07(s, 4H), 7.51(d, J=8.7 Hz, 2H), 8.03(d, J=2.9 Hz, 2H).

EXAMPLE 36

N,N'-Bis[2-(3,4,5-trimethoxyphenyl)-5-pyridyl]-N,N'-diethylethylenediamine dimethanesulfonate

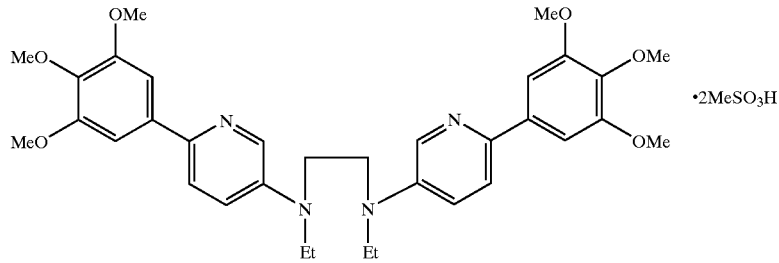

Following the procedure of Example 7, N,N'-bis[2-(3,4,5-trimethoxyphenyl)-5-pyridyl]-N,N'-diethylethylenediamine was obtained as a pale yellow crystalline powder (100.0 mg, yield: 33%) from 5-chloro-2-(3,4,5-trimethoxypheny)-pyridine (335.0 mg, 1.20 mmol) synthesized as described in Reference Example 2 and N,N'-diethylethylenediamine (58.0 mg, 0.500 mmol).

To a solution of N,N'-bis[2-(3,4,5-trimethoxyphenyl)-5-pyridyl]-N,N'-diethylethylenediamine (100.0 mg, 0.165 mmol) in methanol-chloroform (1:1, 6.0 mL) was added a 1.0 M aqueous methanesulfonic acid solution (0.33 mL, 0.33 mmol), and the reaction mixture was concentrated under reduced pressure. Ethanol (5.0 mL) was added to the residue, and the mixture was concentrated under reduced pressure. The residue was recrystallized from methanol-diethyl ether to yield the title compound as a yellow crystalline powder (melting point: 254.0–256.0° C. )(90.0 mg, yield: 69%).

$^1$H-NMR (DMSO-$d_6$, 120° C. )(ammonium salt NH$^+$ protons were not observed) δ: 1.17(t, J=6.8 Hz, 6H), 2.41(s, 6H), 3.50(q, J=6.8 Hz, 4H), 3.66(s, 4H), 3.76(s, 6H), 3.86(s, 12H), 7.18(s, 4H), 7.45(dd, J=2.9, 9.0 Hz, 2H),7.85(d, J=9.0 Hz, 2H), 8.09(d, J=2.9 Hz, 2H).

EXAMPLE 37

N,N'-Bis[2-(3,4,5-trimethoxyphenyl)-5-pyridyl]-N,N'-dimethyl-1,3-propanediamine dimethanesulfonate Following the procedure of Example 7, crude N,N'-bis[2-(3,4,5-trimethoxyphenyl)-5-pyridyl]-N,N'-dimethyl-1,3-propanediamine was obtained as a pale brown oil (275.0 mg) from 5-chloro-2-(3,4,5-trimethoxypheny)pyridine (335.0 mg, 1.20 mmol) synthesized as described in Reference Example 2 and N,N'-dimethyl-1,3-propanediamine (65.0 mg, 0.500 mmol).

To a solution of the crude N,N'-bis[2-(3,4,5-trimethoxyphenyl)-5-pyridyl]-N,N'-dimethyl-1,3-propanediamine (275.0 mg, approx. 0.46 mmol) in methanol-chloroform (1:1, 6.0 mL) was added a 1.0 M aqueous methanesulfonic acid solution (0.93 mL, 0.93 mmol), and the reaction mixture was concentrated under reduced pressure. Ethanol (5.0 mL) was added to the residue, and the mixture was concentrated under reduced pressure. The residue was recrystallized from methanol-diethyl ether to yield the title compound as yellow needles (melting point: 216.0–219.0° C.)(255.0 mg, yield: 70% based on N,N'-dimethyl-1,3-propanediamine).

$^1$H-NMR (DMSO-$d_6$, 120° C.)(ammonium salt NH$^+$ protons were not observed) δ: 1.94(tt, J=7.3 Hz, 2H), 2.43(s, 6H), 3.05(s, 6H), 3.52(t, J=7.3 Hz, 4H), 3.76(s, 6H), 3.86(s, 12H), 7.15(s, 4H), 7.53(dd, J=3.1, 9.2 Hz, 2H), 7.88(d, J=9.2 Hz, 2H), 8.10(d,J=3.1 Hz, 2H).

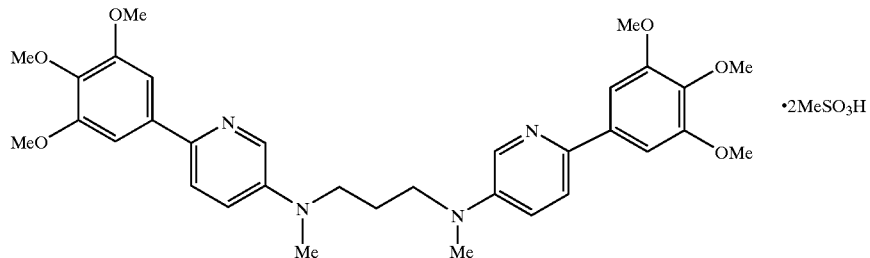

EXAMPLE 38

N,N'-Bis[2-(3,4,5-trimethoxyphenyl)-5-pyridyl]-N,N'-diethyl-1,3-propanediamine dimethanesulfonate

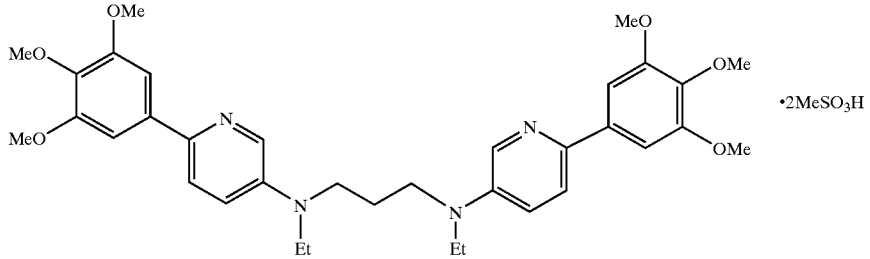

Following the procedure of Example 7, crude N,N'-bis[2-(3,4,5-trimethoxyphenyl)-5-pyridyl]-N,N'-diethyl-1,3-propanediamine was obtained as a pale brown crystalline powder (160.0 mg) from 5-chloro-2-(3,4,5-trimethoxypheny)pyridine (335.0 mg, 1.20 mmol) synthesized as described in Reference Example 2 and N,N'-diethyl-1,3-propanediamine (65.0 mg, 0.500 mmol).

To a solution of the crude N,N'-bis[2-(3,4,5-trimethoxyphenyl)-5-pyridyl]-N,N'-diethyl-1,3-propanediamine (160.0 mg, approx. 0.26 mmol) in methanol-chloroform (1:1, 6.0 mL) was added a 1.0 M aqueous methanesulfonic acid solution (0.51 mL, 0.51 mmol), and the reaction mixture was concentrated under reduced pressure. Ethanol (5.0 mL) was added to the residue, and the mixture was concentrated under reduced pressure. The residue was recrystallized from methanol-methylene chloride-diethyl ether to yield the title compound as a yellow crystalline powder (melting point: 239.0–242.0° C.)(92.0 mg, yield: 45% based on N,N'-diethyl-1,3-propanediamine).

$^1$H-NMR (DMSO-$d_6$, 120° C. )(ammonium salt $NH^+$ protons were not observed) δ: 1.14–1.21(m, 6H), 1.88–1.97 (m, 2H), 2.43(s, 6H), 3.44–3.54(m, 8H), 3.76(s, 6H), 3.86(s, 12H), 7.16(s, 4H), 7.48–7.54(m, 2H), 7.83–7.90(m, 2H), 8.08–8.14(m, 2H).

EXAMPLE 39

N,N'-Bis[2-(3,4,5-trimethoxyphenyl)-5-pyridyl]-N,N',2,2-tetramethyl-1,3-propanediamine dimethanesulfonate Following the procedure of Example 7, N,N'-bis[2-(3,4,5-trimethoxyphenyl)-5-pyridyl]-N,N',2,2-tetramethyl-1,3-propanediamine was obtained as a pale yellow oil (210.0 mg, yield: 68%) from 5-chloro-2-(3,4,5-trimethoxypheny)pyridine (335.0 mg, 1.20 mmol) synthesized as described in Reference Example 2 and N,N',2,2-tetramethyl-1,3-propanediamine (65.0 mg, 0.500 mmol).

To a solution of N,N'-bis[2-(3,4,5-trimethoxyphenyl)-5-pyridyl]-N,N',2,2-tetramethyl-1,3-propanediamine (210.0 mg, 0.340 mmol) in methanol-chloroform (1:1, 6.0 mL) was added a 1.0 M aqueous methanesulfonic acid (0.68 mL, 0.68 mmol), and the reaction mixture was concentrated under reduced pressure. Ethanol (5.0 mL) was added to the residue, and the mixture was concentrated under reduced pressure. The residue was recrystallized from methanol-diethyl ether to yield the title compound as a yellow crystalline powder (melting point: 123.0–128.0° C.)(161.0 mg, yield: 59%).

$^1$H-NMR (DMSO-$d_6$, 120° C. )(ammonium salt $NH^+$ protons were not observed) δ: 1.08(s, 6H), 2.44(s, 6H), 3.15(s, 6H), 3.49(s, 4H), 3.76(s, 6H), 3.87(s, 12H), 7.18(s, 4H), 7.65(dd, J=3.1, 9.2 Hz, 2H), 7.90(d, J=9.2 Hz, 2H), 8.19(d, J=3.1 Hz, 2H).

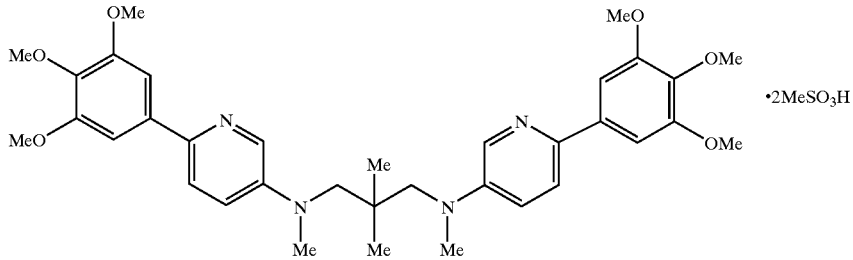

EXAMPLE 40

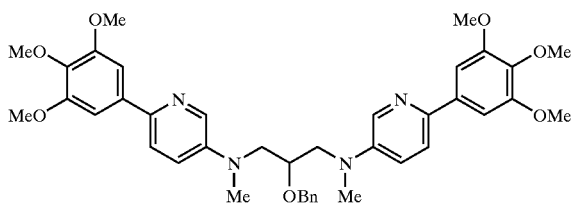

Following the procedure of Example 7, the title compound was obtained as a pale yellow amorphous powder (69.0 mg, yield: 59%) from 5-chloro-2-(3,4,5-trimethoxypheny)pyridine (113.0 mg, 0.400 mmol) synthesized as described in Reference Example 2 and 2-benzyloxy-N,N'-dimethyl-1,3-propanediamine (35.0 mg, 0.160 mmol) synthesized as described in Reference Example 10.

$^1$H-NMR (CDCl$_3$) δ: 3.04(s, 6H), 3.49–3.51(m, 4H), 3.88(s, 6H), 3.93(s, 12H), 4.03–4.1 1(m, 1H), 4.52(s, 2H), 7.00(dd, J=3.1, 8.7 Hz, 2H), 7.11–7.16(m, 2H), 7.16(s, 4H), 7.23–7.26(m, 3H), 7.49(d, J=8.7 Hz, 2H), 8.21(d, J=3.1 Hz, 2H).

EXAMPLE 41

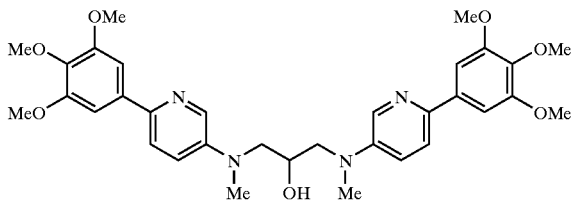

To a solution of 2-benzyloxy-N,N'-bis[2-(3,4,5-trimethoxyphenyl)-5-pyridyl]-N,N'-dimethyl-1,3-propanediamine (40.0 mg, 0.050 mmol) synthesized as described in Example 40 in methanol (5.0 mL) were added 1.0 M hydrochloric acid (2.5 mL, 2.5 mmol) and 10% palladium on charcoal (25.0 mg), and the resulting mixture was stirred at 45° C. for 15 hours under hydrogen. Insoluble materials were removed by filtration through Celite. The filtrate was rendered basic by the addition of saturated aqueous sodium hydrogencarbonate and extracted with chloroform. The organic layer was washed with water, dried over anhydrous sodium sulfate, and concentrated under reduced pressure. The residue was purified by column chromatography on silica gel to yield the title compound as a pale yellow amorphous powder (27.0 mg, yield: 89%).

$^1$H-NMR (CDCl$_3$)(alcohol OH protons were not observed) δ: 3.08(s, 6H), 3.40–3.55(m, 4H), 3.88(s, 6H), 3.94(s, 12H), 4.26–4.35(m, 1H), 7.12(dd, J=2.9, 9.0 Hz, 2H), 7.14(s, 4H), 7.55(d, J=9.0 Hz, 2H), 8.25(d, J=2.9 Hz, 2H).

EXAMPLE 42

N,N-Bis[N-[2-(3,4,5-trimethoxyphenyl)-5-pyridyl]-N-methyl-2-aminoethyl]methylamine trihydrochloride.

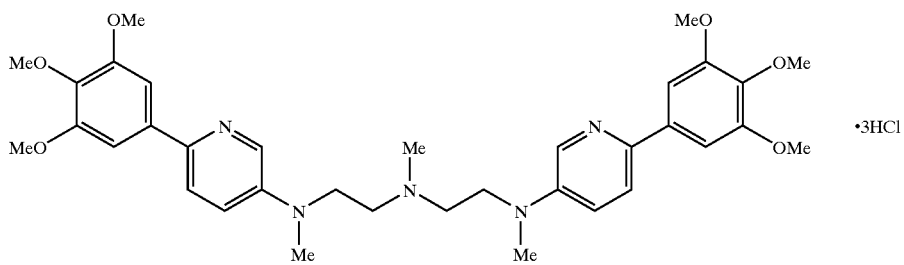

To a solution of methyliminodiacetic acid (74.0 mg, 0.503 mmol) in methylene chloride (2.5 mL) were added dimethylformamide (25 mg, 0.34 mmol) and oxalyl chloride (0.22 mL, 2.3 mmol). The reaction mixture was stirred at room temperature for 2 hours and then concentrated under reduced pressure. To an ice-cold solution of the residue in methylene chloride (5 mL) were added N,N-diisopropylethylamine (0.90 mL, 5.2 mmol) and 5-amino-2-(3,4,5-trimethoxyphenyl)pyridine (262 mg, 1.00 mmol) synthesized as described in Reference Example 11. After being stirred in ice for 2 hours, saturated aqueous sodium hydrogencarbonate was added, and the mixture was extracted with chloroform. The organic layer was dried over anhydrous sodium sulfate and concentrated under reduced pressure. The residue was purified by column chromatography on silica gel to yield N,N-bis[N-[2-(3,4,5-trimethoxyphenyl)-5-pyridyl]carbamoylmethyl]methylamine as a colorless oil (94.5 mg, yield: 30%).

Under nitrogen, lithium aluminum hydride (23.1 mg, 0.609 mmol) was added to a solution of N,N-bis[N-[2-(3,4,5-trimethoxyphenyl)-5-pyridyl]carbamoylmethyl] methylamine (88.1 mg, 0.139 mmol) in anhydrous tetrahydrofuran (5.0 mL), and the resulting mixture was stirred at 65° C. for 1 hour. Methanol (0.2 mL, 4.9 mmol) was added to the ice-cold reaction mixture, and the ice bath was removed. Water (0.2 mL), diethyl ether (20 mL), and anhydrous magnesium sulfate (1.5 g) were added, and the mixture was stirred at room temperature for 2 hours. Insoluble materials were removed by filtration through Celite, and the filtrate was concentrated under reduced pressure. The residue was purified by column chromatography on silica gel to yield N,N-bis[N-[2-(3,4,5-trimethoxyphenyl)-5-pyridyl]-2-aminoethyl]methylamine as a colorless oil (58.2 mg, yield: 69%).

To an ice-cold solution of N,N-bis[N-[2-(3,4,5-trimethoxyphenyl)-5-pyridyl]-2-aminoethyl]methylamine (58.2 mg, 0.0964 mmol) in tetrahydrofuran (1.0 mL) were added paraformaldehyde (67.4 mg, 2.24 mmol) and sodium borohydride (46.4 mg, 1.23 mmol), followed by the gradual addition of trifluoroacetic acid (1.0 mL) over about 15 minutes. The ice bath was removed, and the mixture was stirred at room temperature for 16 hours. Paraformaldehyde (33.2 mg, 1.11 mmol) and sodium borohydride (24.0 mg, 0.634 mmol) were added in several portions, and the resulting mixture was stirred at room temperature for additional 6 hours. To the ice-cold reaction mixture was added a 2.5 M aqueous sodium hydroxide (5.0 mL), and mixture was extracted with chloroform. The organic layer was dried over anhydrous sodium sulfate and concentrated under reduced pressure. The residue was purified by preparative thin-layer chromatography on silica gel to yield N,N-bis[N-[2-(3,4,5-trimethoxyphenyl)-5-pyridyl]-N-methyl-2-aminoethyl]methylamine as a colorless oil (37.2 mg, yield: 61%).

To a solution of N,N-bis[N-[2-(3,4,5-trimethoxyphenyl)-5-pyridyl]-N-methyl-2-aminoethyl]methylamine (42.0 mg, 0.059 mmol) in ethanol (10 mL) was added 1.0 M hydrochloric acid (0.30 mL, 0.30 mmol), and the reaction mixture was concentrated under reduced pressure. Ethanol (10 mL) was added to the residue, and the mixture was concentrated under reduced pressure. The residue was recrystallized from ethanol-diethyl ether to yield the title compound as a yellow crystalline powder [melting point: 187.0° C. (decomposed)] (37.1 mg, yield: 75%).

$^1$H-NMR (CDCl$_3$)(ammonium salt NH$^+$ protons were not observed) δ: 3.07(br s, 3H), 3.19(br s, 6H), 3.49–3.70(m, 4H), 3.87(br s, 6H), 3.96(br s, 12H), 4.03–4.25(m, 4H), 7.17(br s, 4H), 7.83–7.97(m, 2H), 7.94–8.08(m, 2H), 8.16–8.30(m, 2H).

EXAMPLE 43

N,N-Bis[N-[2-(3,4,5-trimethoxyphenyl)-5-pyridyl]-N-methyl-3-aminopropyl]methylamine

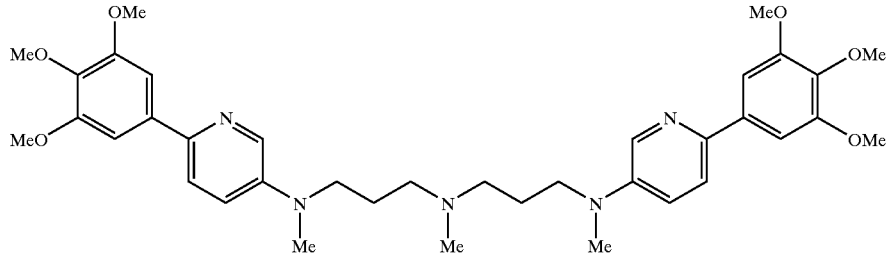

Following the procedure of Example 7, the title compound was obtained as a pale yellow amorphous powder (94.0 mg, yield: 28%) from 5-chloro-2-(3,4,5-trimethoxypheny)pyridine (335.0 mg, 1.20 mmol) synthesized as described in Reference Example 2 and N,N-bis(N-methyl-3-aminopropyl)methylamine (87.0 mg, 0.500 mmol).

$^1$H-NMR (CDCl$_3$) δ: 1.75–1.85(m, 4H), 2.23(s, 3H), 2.35–2.45(m, 4H), 2.99(s, 6H), 3.39–3.48(m, 4H), 3.87(s, 6H), 3.93(s, 12H), 7.04(dd, J=2.9, 8.7 Hz, 2H),7.14(s, 4H), 7.54(d, J=8.7 Hz, 2H), 8.20(d, J=2.9 Hz, 2H).

EXAMPLE 44

Bis[N-[2-(3,4,5-trimethoxyphenyl)-5-pyridyl]-2-aminoethyl]ether dimethanesulfonate

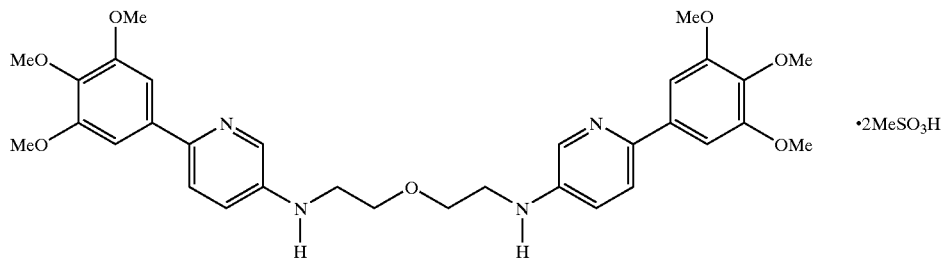

To an ice-cold solution of 5-amino-2-(3,4,5-trimethoxyphenyl)pyridine (203.6 mg, 0.783 mmol) synthesized as described in Reference Example 11 in methylene chloride (4 mL) were added N,N-diisopropylethylamine (0.20 mL, 1.1 mmol) and diglycolyl chloride (75.8 mg, 0.443 mmol). After being stirred in ice for 30 minutes, water was added to the reaction mixture. The mixture was extracted with methanol-chloroform (1:20), and the organic layer was dried over anhydrous sodium sulfate and concentrated under reduced pressure. The residue was purified by column chromatography on silica gel to yield bis[N-[2-(3, 4,5-trimethoxyphenyl)-5-pyridyl]carbamoylmethyl]ether as a colorless oil (224.3 mg, yield: 93%).

Under nitrogen, lithium aluminum hydride (33.2 mg, 0.875 mmol) was added to a solution of bis[N-[2-(3,4,5-trimethoxyphenyl)-5-pyridyl]carbamoylmethyl]ether (121.3 mg, 0.196 mmol) in anhydrous tetrahydrofuran (6 mL), and the mixture was stirred at 65° C. for 2 hours. Methanol (0.2 mL, 4.9 mmol) was added to the ice-cold reaction mixture, and the ice bath was removed. Water (0.2 mL), diethyl ether (20 mL), and anhydrous magnesium sulfate (1.5 g) were added, and the mixture was stirred at room temperature for 1 hour. Insoluble materials were removed by filtration through Celite, and the filtrate was concentrated under reduced pressure. The residue was purified by column chromatography on silica gel to yield bis[N-[2-(3,4,5-trimethoxyphenyl)-5-pyridyl]-2-aminoethyl]ether as a colorless oil (98.5 mg, yield: 85%).

To a solution of bis[N-[2-(3,4,5-trimethoxyphenyl)-5-pyridyl]-2-aminoethyl]ether (53.1 mg, 0.0900 mmol) in ethanol (5.0 mL) was added a 1.0 M aqueous methanesulfonic acid solution (0.20 mL, 0.20 mmol), and the reaction mixture was concentrated under reduced pressure. Ethanol (10 mL) was added to the residue, and the mixture was concentrated under reduced pressure. The residue was suspended in ethanol-diethyl ether and the resulting precipitate was collected by filtration to provide the title compound as a pale brown amorphous powder (49.9 mg, yield: 71%).

$^1$H-NMR (CDCl$_3$)(ammonium salt NH$^+$ protons were not observed) δ: 2.90(s, 6H), 3.38(br t, J=4.4 Hz, 4H), 3.77(br t, J=4.4 Hz, 4H), 3.89(s, 6H), 3.93(s, 12H), 6.93(s, 4H), 7.44(d, J=9.1 Hz, 2H), 7.73(br d, J=9.1 Hz, 2H), 8.38(br s, 2H).

EXAMPLE 45

Bis[N-[2-(3,4,5-trimethoxyphenyl)-5-pyridyl]-N-methyl-2-aminoethyl]ether dimethaesulfonate

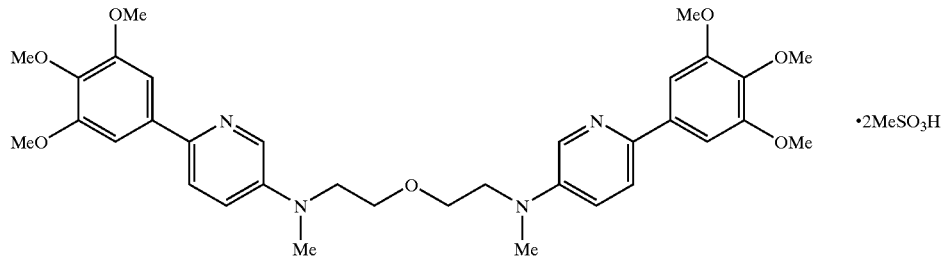

To an ice-cold solution of bis[N-[2-(3,4,5-trimethoxyphenyl)-5-pyridyl]-2-aminoethyl]ether (23.6 mg, 0.0400 mmol) synthesized as described in Example 44 in tetrahydrofuran (0.5 mL) were added paraformaldehyde (25.9 mg, 0.862 mmol) and sodium borohydride (18.0 mg, 0.476 mmol). After a solution of trifluoroacetic acid (0.25 mL) in tetrahydrofuran (0.50 mL) was gradually added over about 10 minutes, the ice bath was removed and the mixture was stirred at room temperature for 30 minutes. Paraformaldehyde (25.0 mg, 0.833 mmol) and sodium borohydride (17.8 mg, 0.47 mmol) were added in several portions, and the resulting mixture was stirred for 20 hours. To the ice-cold reaction mixture was added a 2.5 M aqueous sodium hydroxide solution (5.0 mL), and the mixture was extracted with chloroform. The organic layer was dried over anhydrous sodium sulfate and concentrated under reduced pressure. The residue was purified by preparative thin-layer chromatography on silica gel to yield bis[N-[2-(3,4,5-trimethoxyphenyl)-5-pyridyl]-N-methyl-2-aminoethyl]ether as a colorless oil (18.8 mg, yield: 76%).

To a solution of bis[N-[2-(3,4,5-trimethoxyphenyl)-5-pyridyl]-N-methyl-2-aminoethyl]ether (47.5 mg, 0.0769 mmol) in ethanol (5.0 mL) was added a 1.0 M aqueous methanesulfonic acid solution (0.17 mL, 0.17 mmol), and the reaction mixture was concentrated under reduced pressure. Ethanol (10 mL) was added to the residue, and the mixture was concentrated under reduced pressure. The residue was recrystallized from ethanol-diethyl ether to provide the title compound as a yellow crystalline powder (melting point: 165.5–169.0° C.) (38.8 mg, yield: 62%).

$^1$H-NMR (CDCl$_3$)(ammonium salt NH$^+$ protons were not observed) δ: 2.89(s, 6H), 3.07(s, 6H), 3.63(br t, J=4.9 Hz, 4H), 3.77(br t, J=4.9 Hz, 4H), 3.88(s, 6H), 3.94(s, 12H), 6.98(s, 4H), 7.74(br dd, J=2.9, 9.3 Hz, 2H), 7.87(br d, J=9.3 Hz, 2H), 8.40(br s, 2H).

EXAMPLE 46

N,N'-Bis[2-(3,4,5-trimethoxyphenyl)-5-pyridyl]-N, N'-dimethyl-3-(1-pyrrolidinyl)-1,5-pentanediamine trihydrochloride

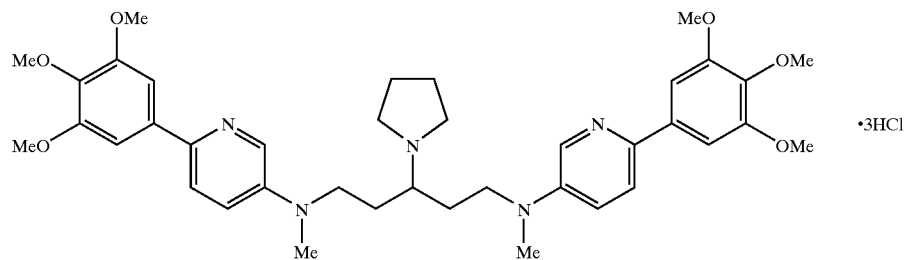

Following the procedure of Example 7, N,N'-bis[2-(3,4,5-trimethoxyphenyl)-5-pyridyl]-N,N'-dimethyl-3-(1-pyrrolidinyl)-1,5-pentanediamine was obtained as a colorless oil (49.6 mg, yield: 27%) from 2-(3,4,5-trimethoxyphenyl)-5-chloropyridine (182.6 mg, 0.635 mmol) synthesized as described in Reference Example 2 and N,N'-dimethyl-3-(1-pyrrolidinyl)-1,5-pentanediamine (54.0 mg, 0.217 mmol).

To a solution of N,N'-bis[2-(3,4,5-trimethoxyphenyl)-5-pyridyl]-N,N'-dimethyl-3-(1-pyrrolidinyl)-1,5-pentanediamine (49.6 mg, 0.0724 mmol) in ethanol (5.0 mL) was added 1.0 M hydrochloric acid solution (0.40 mL, 0.40 mmol), and the reaction mixture was concentrated under reduced pressure. Ethanol (10 mL) was added to the residue, and the resulting mixture was concentrated under reduced pressure to yield the title compound as a pale yellow amorphous powder (46.0 mg, yield: 71%).

$^1$H-NMR (CDCl$_3$)(ammonium salt NH$^+$ protons were not observed) δ: 2.00–2.35(m, 8H), 3.10–3.25(m, 2H), 3.17(br s, 6H),3.65–3.80(m, 3H), 3.82–3.98(m, 4H), 3.90(s, 6H), 3.99 (s, 12H), 7.24(s, 4H), 7.79(br d, J=8.8 Hz, 2H), 7.90(br d, J=8.8 Hz, 2H), 8.20(br s, 2H).

EXAMPLE 47

2-(Dimethylamino)methyl-1,4-bis[2-(,3,4,5-trimethoxyphenyl)-5-pyridyl]piperazine trihydrochloride

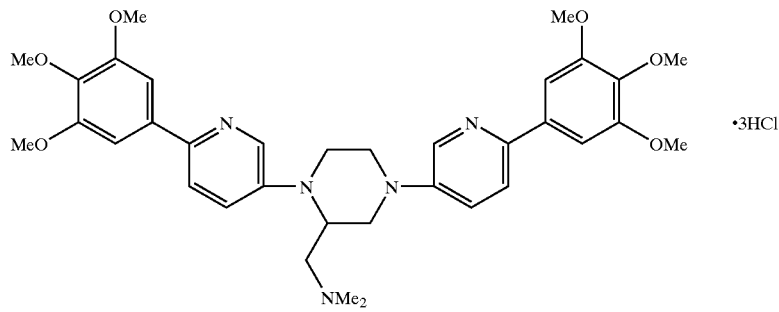

Following the procedure of Example 7, 2-(dimethylamino)methyl-1,4-bis [2-(3,4,5-trimethoxyphenyl)-5-pyridyl]piperazine was obtained as a colorless oil (32.3 mg, yield: 20%) from 2-(3,4,5-trimethoxypheny)-5-chloropyridine (198.9 mg, 0.712 mmol) synthesized as described in Reference Example 2 and 2-(dimethylaminomethyl)piperazine (37.0 mg, 0.259 mmol).

To a solution of 2-(dimethylamino)methyl-1,4-bis[2-(3,4,5-trimethoxyphenyl)-5-pyridyl]piperazine (32.3 mg, 0.0512 mmol) in ethanol (5.0 mL) was added 1.0 M hydrochloric acid (0.20 mL, 0.20 mmol), and the reaction mixture was concentrated under reduced pressure. Ethanol (10 mL) was added to the residue, and the mixture was concentrated under reduced pressure. The residue was recrystallized from ethanol-diethyl ether to yield the title compound as a pale yellow crystalline powder [melting point: 199.5° C. (decomposed)](25.7 mg, yield: 68%).

$^1$H-NMR (CDCl$_3$)(data for the free base of the title compound) δ: 2.21 (br d, J=11.5 Hz, 1H), 2.24–2.33(m, 1H), 2.27(s, 6H), 2.95(dd, J=11.5, 11.5 Hz, 1H), 3.14(ddd, J=3.5, 11.5, 11.5 Hz, 11H), 3.18(dd, J=3.5, 11.5 Hz, 1H), 3.34(ddd, J=3.5, 11.5, 11.5 Hz, 1H), 3.57(br ddd, J=3.5, 3.5, 11.5 Hz, 1H), 3.74(br d, J=11.5 Hz, 1H), 3.90(s, 6H), 3.97(s, 12H), 4.11(br d, J=11.5 Hz, 1H), 7.19(s, 2H), 7.19(s, 2H), 7.26(dd, J=2.9, 8.8 Hz, 1H), 7.33(dd, J=2.9, 8.8 Hz, 1H), 7.61(d, J=8.8 Hz, 1H), 7.62(d, J=8.8 Hz, 1H), 8.38(d, J=2.9 Hz, 1H), 8.43(d, J=2.9 Hz, 1H).

EXAMPLE 48

N,N'-Bis[2-(3,4,5-trimethoxyphenyl)-5-pyridyl]-4,4'-bipiperidine dimethanesulfonate

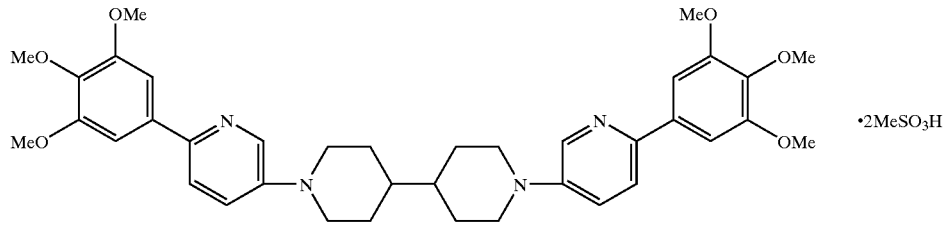

Following the procedure of Example 7, N,N'-bis[2-(3,4,5-trimethoxyphenyl)-5-pyridyl]-4,4'-bipiperidine was obtained as a pale yellow crystalline powder (228.0 mg, yield: 69%) from 5-chloro-2-(3,4,5-trimethoxypheny)

pyridine (335.0 mg, 1.20 mmol) synthesized as described in Reference Example 2 and 4,4'-bipiperidine (84.0 mg, 0.500 mmol).

To a solution of N,N'-bis[2-(3,4,5-trimethoxyphenyl)-5-pyridyl]-4,4'-bipiperidine (228.0 mg, 0.340 mmol) in methanol-chloroform(1:1, 6.0 mL) was added a 1.0 M aqueous methanesulfonic acid (0.70 mL, 0.70 mmol), and the reaction mixture was concentrated under reduced pressure. Ethanol (5.0 mL) was added to the residue, and the mixture was concentrated under reduced pressure. The residue was recrystallized from methanol-methylene chloride-diethyl ether to yield the title compound as yellow needles (melting point: 226.0–228.0° C.)(170.0 mg, yield: 59%).

$^1$H-NMR (DMSO-$d_6$, 120° C. )(ammonium salt NH$^+$ protons were not observed) δ: 1.35–1.50(m, 6H), 1.81–1.92 (m, 4H), 2.44(s, 6H), 2.81–2.97(m, 4H), 3.77(s, 6H), 3.88(s, 12H), 3.90–3.92(m, 4H), 7.20(s, 4H), 7.73(dd, J=2.9, 9.0 Hz, 2H), 7.93(d, J=9.0 Hz, 2H), 8.25(d, J=2.9 Hz, 2H).

EXAMPLE 49

N,N'-Bis[2-(3,4,5-trimethoxypheyl)-5-pyridyl]-N,N'-dimethyl-1,6-hexanediamine dimethanesulfonate

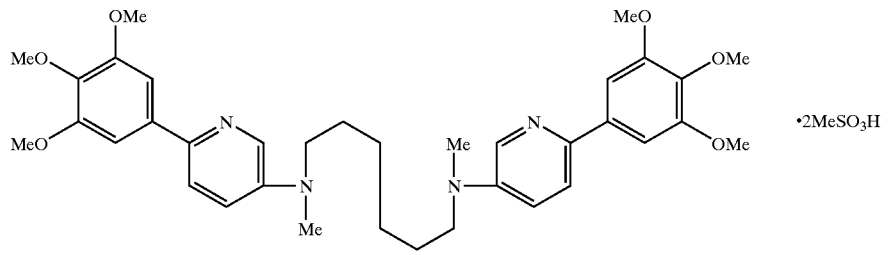

Following the procedure of Example 7, N,N'-bis[2-(3,4,5-trimethoxyphenyl)-5-pyridyl]-N,N'-dimethyl-1,6-hexanediamine was obtained as a pale yellow crystalline powder (243.0 mg, yield: 75%) from 5-chloro-2-(3,4,5-trimethoxyphenyl)pyridine (335.0 mg, 1.20 mmol) synthesized as described in Reference Example 2 and N,N'-dimethyl-1,6-hexanediamine (72.0 mg, 0.500 mmol).

To a solution of N,N'-bis[2-(3,4,5-trimethoxyphenyl)-5-pyridyl]-N,N'-dimethyl-1,6-hexanediamine (243.0 mg, 0.370 mmol) in methanol-methylene chloride (6:1, 3.5 mL) was added a 1.0 M aqueous methanesulfonic acid (0.76 mL, 0.76 mmol), and the reaction mixture was concentrated under reduced pressure. Ethanol (5.0 mL) was added to the residue, and the mixture was concentrated under reduced pressure. The residue was recrystallized from methanol-diethyl ether to yield the title compound as yellow needles (melting point: 192.0–195.0° C.) (251.0 mg, yield: 81%).

$^1$H-NMR (DMSO-$d_6$, 120° C. )(ammonium salt NH$^+$ protons were not observed) δ: 1.37–1.45(m, 4H), 1.56–1.67 (m, 4H), 2.42(s, 6H), 3.02(s, 6H), 3.40–3.47(m, 4H), 3.76(s, 6H), 3.87(s, 12H), 7.17(s, 4H), 7.50(dd, J=3.1, 9.0 Hz, 2H), 7.89(d, J=9.0 Hz, 2H), 8.04(d, J=3.1 Hz, 2H).

EXAMPLE 50

N,N'-Bis[2-(3,5-dimethoxyphenyl)-5-pyridyl]-N,N'-diethylethylenediamine dimethanesulfonate

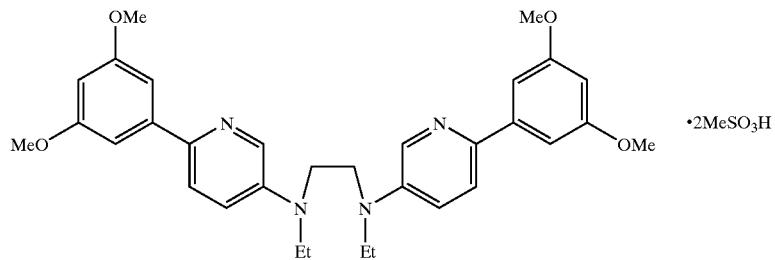

Following the procedure of Example 1, N,N'-bis[2-(3,5-dimethoxyphenyl)-5-pyridyl]-N,N'-diethylethylenediamine was obtained as a colorless oil (55.0 mg, yield: 42%) from N,N'-bis(2-trifluoromethanesulfonyloxy-5-pyridyl)-N,N'-diethylethylenediamine (136.0 mg, 0.240 mmol) synthesized by a similar procedure to that described in Reference Example 1 and 3,5-dimethoxyphenylboronic acid (80.0 mg, 0.530 mmol).

To a solution of N,N'-bis[2-(3,5-dimethoxyphenyl)-5-pyridyl]-N,N'-diethylethylenediamine (55.0 mg, 0.100 mmol) in methanol (2.0 mL) was added a 1.0 M aqueous methanesulfonic acid (0.20 mL, 0.20 mmol), and the reaction mixture was concentrated under reduced pressure. Ethanol (5.0 mL) was added to the residue, and the mixture was concentrated under reduced pressure. The residue was recrystallized from methanol-diethyl ether to yield the title compound as a yellow crystalline powder (melting point: 280.0–282.0° C.) (48.0 mg, yield: 64%).

¹H-NMR [CD₃OD-CDCl₃,(1:10)](ammonium salt NH⁺ protons were not observed) δ: 1.26(t, J=6.8 Hz, 6H), 2.83(s, 6H), 3.64(q, J=6.8 Hz, 4H), 3.77(s, 4H), 3.89(s, 12H), 6.60(t, J=2.2 Hz, 2H), 6.93(d, J=2.2 Hz, 4H), 7.75(dd, J=2.9, 10.3 Hz, 2H), 7.92(d, J=10.3 Hz, 2H), 8.45(d, J=2.9 Hz, 2H).

EXAMPLE 51

N,N'-Diethyl-N,N'-bis[2-(4-isopropoxy-3,5-dimethoxypheyl)-5-pyridyl]ehtylenediamine dimethanesulfonate

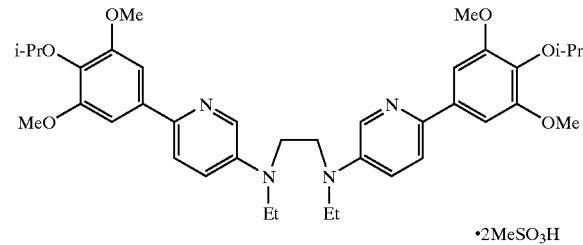

Following the procedure of Example 1, N,N'-diethyl-N,N'-bis[2-(4-isopropoxy-3,5-dimethoxyphenyl)-5-pyridyl]ethylenediamine was obtained as a colorless oil (129.0 mg, yield: 98%) from N,N'-bis(2-trifluoromethanesulfonyloxy-5-pyridyl)-N,N'-diethylethylenediamine (113.0 mg, 0.200 mmol) synthesized by a similar procedure as described in Reference Example 1 and 4-isopropoxy-3,5-dimethoxyphenylboronic acid (106.0 mg, 0.440 mmol).

To a solution of N,N'-diethyl-N,N'-bis[2-(4-isopropoxy-3,5-dimethoxyphenyl)-5-pyridyl]ethylenediamine (129.0 mg, 0.200 mmol) in methanol (2.0 mL) was added a 1.0 M aqueous methanesulfonic acid solution (0.40 mL, 0.40 mmol), and the reaction mixture was concentrated under reduced pressure. Ethanol (5.0 mL) was added to the residue, and the mixture was concentrated under reduced pressure. The residue was recrystallized from methanol-diethyl ether to afford the title compound as a yellow crystalline powder (melting point: 260.0–261.0° C.) (102.0 mg, yield: 60%).

¹H-NMR (CDCl₃)(ammonium salt NH⁺ protons were not observed) δ: 1.27(t, J=6.8 Hz, 6H), 1.32(d, J=6.1 Hz, 12H), 2.85(s, 6H), 3.72(s, 4H), ³.⁷⁶(q, J=6.8 Hz, 4H), 3.94(s, 12H), 4.47(qq, J=6.1, 6.1 Hz, 2H), 7.07(s, 4H),7.69(dd, J=2.9, 9.3 Hz, 2H), 7.88(d, J=9.3 Hz, 2H), 8.72(d, J=2.9 Hz, 2H).

EXAMPLE 52

N,N'-Bis[2-(3,5-dimethoxyphenyl)-5-pyridyl]-N,N'-dimethyl-1,3-propanediamine dimethanesulfonate

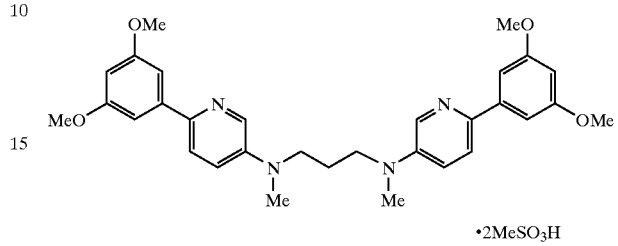

Following the procedure of Example 1, N,N'-bis[2-(3,5-dimethoxyphenyl)-5-pyridyl]-N,N'-dimethyl-1,3-propanediamine was obtained as a colorless oil (35.0 mg, yield: 35%) from N,N'-bis(2-trifluoromethanesulfonyloxy-5-pyridyl)-N,N'-dimethyl-1,3-propanediamine (95.0 mg, 0.190 mmol) synthesized by a similar procedure to that described in Reference Example 1 and 3,5-dimethoxyphenylboronic acid (63.0 mg, 0.420 mmol).

To a solution of N,N'-bis[2-(3,5-dimethoxyphenyl)-5-pyridyl]-N,N'-dimethyl-1,3-propanediamine (35.0 mg, 0.070 mmol) in methanol (2.0 mL) was added a 1.0 M aqueous methanesulfonic acid (0.15 mL, 0.15 mmol), and the reaction mixture was concentrated under reduced pressure. Ethanol (5.0 mL) was added to the residue, and the mixture was concentrated under reduced pressure. The residue was recrystallized from ethanol to afford the title compound as a yellow crystalline powder (melting point: 228.0–231.0° C.) (21.0 mg, yield: 43%).

¹H-NMR (CDCl₃)(ammonium salt NH⁺ protons were not observed) δ: 2.07(tt, J=7.3, 7.3 Hz, 2H), 2.90(s, 6H), 3.21(s, 6H), 3.58(t, J=7.3 Hz, 4H), 3.85(s, 12H), 6.78(t, J=2.2 Hz, 2H), 6.86(d, J=2.2 Hz, 4H), 7.81(dd, J=3.2, 9.3 Hz, 2H), 7.91(d, J=9.3 Hz, 2H), 8.71(d, J=3.2 Hz, 2H).

EXAMPLE 53

N,N'-Bis[2-(4-isopropoxy-3,5-diethxyphenyl)-5-pyridyl]-N,N'-dimethyl-1,3-propanediamine dimethanesulfonate

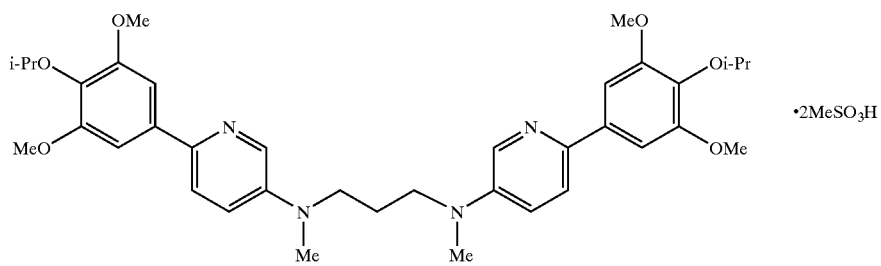

Following the procedure of Example 1, N,N'-bis[2-(4-isopropoxy-3,5-dimethoxyphenyl)-5-pyridyl]-N,N'-dimethyl-1,3-propanediamine was obtained as a colorless viscous oil (27.0 mg, yield: 33%) from N,N'-bis(2-trifluoromethanesulfonyloxy-5-pyridyl)-N,N'-dimethyl-1,3-propanediamine (61.0 mg, 0.125 mmol) synthesized by a similar procedure to that described in Reference Example 1 and 4-isopropoxy-3,5-dimethoxyphenylboronic acid (66.0 mg, 0.275 mmol).

To a solution of N,N'-bis[2-(4-isopropoxy-3,5-dimethoxyphenyl)-5-pyridyl]-N,N'-dimethyl-1,3-propanediamine (27.0 mg, 0.040 mmol) in methanol (2.0 mL) was added a 1.0 M aqueous methanesulfonic acid (0.10 mL, 0.10 mmol), and the reaction mixture was concentrated under reduced pressure. Ethanol (5.0 mL) was added to the residue, and the mixture was concentrated under reduced pressure. The residue was recrystallized from methanol-diethyl ether to afford the title compound as a yellow crystalline powder (melting point: 191.0–192.0° C.)(15.0 mg, yield: 42%).

$^1$H-NMR (CDCl$_3$)(data for the free base of the title compound) δ: 1.31 (d, J=6.1 Hz, 12H), 1.96(tt, J=7.6, 7.6 Hz, 2H), 3.01(s, 6H), 3.45(t, J=7.6 Hz, 4H), 3.91(s, 12H), 4.40(qq, J=6.1 Hz, 2H), 7.14(s, 4H), 7.48(dd, J=2.9, 7.8 Hz, 2H), 7.54(d, J=7.8 Hz, 2H), 8.20(d, J=2.9 Hz, 2H).

EXAMPLE 54

N,N'-Bis[2-(4-hydroxy-3,5-dimethoxyphenyl)-5-pyridyl]-N,N'-dimethyl-1,3-propanediamine dimethanesulfonate ride (1.0 mL) was added trifluoroacetic acid (1.0 mL). The reaction mixture was stirred at room temperature for 30 minutes, and concentrated under reduced pressure. A solution of the residue in chloroform was washed with saturated aqueous sodium hydrogencarbonate and brine, dried over anhydrous sodium sulfate, and concentrated under reduced pressure. The residue was purified by column chromatography on silica gel to yield N,N'-bis[2-(4-hydroxy-3,5-dimethoxyphenyl)-5-pyridyl]-N,N'-dimethyl-1,3-propanediamine as a pale yellow oil (43.0 mg, yield: 86%).

To a solution of N,N'-bis[2-(4-hydroxy-3,5-dimethoxyphenyl)-5-pyridyl]-N,N'-dimethyl-1,3-propanediamine (43.0 mg, 0.076 mmol) in methanol-chloroform (1:2, 3.0 mL) was added a 1.0 M aqueous methanesulfonic acid (0.16 mL, 0.16 mmol), and the reaction mixture was concentrated under reduced pressure. Ethanol (5.0 mL) was added to the residue, and the mixture was concentrated under reduced pressure. The residue was recrystallized from ethanol-diethyl ether to provide the title compound as a yellow crystalline powder (melting point: 198.0–202.0° C.)(17.0 mg, yield: 30%).

$^1$H-NMR (DMSO-d$_6$, 120° C. )(neither ammonium salt NH$^+$ protons nor phenol OH protons were observed) δ: 1.93(tt, J=7.0, 7.0 Hz, 2H), 2.41(s, 6H), 3.05(s, 6H), 3.52(t, J=7.0 Hz, 4H), 3.85(s, 12H), 7.15(s, 4H), 7.59(dd, J=2.9, 9.2 Hz, 2H), 7.88(d, J=9.2 Hz, 2H), 8.09(d, J=2.9 Hz, 2H).

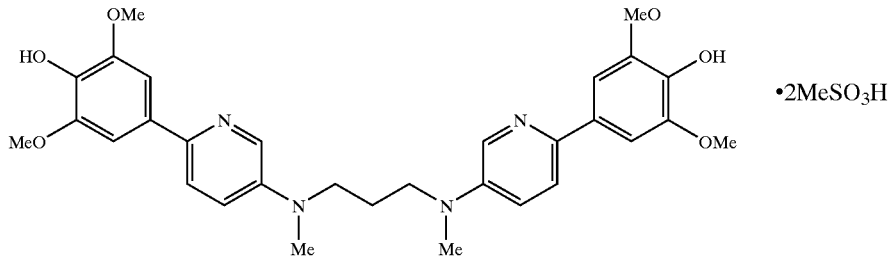

Following the procedure of Example 1, N,N'-bis[2-[4-(4-methoxybenzyloxy)-3,5-dimethoxyphenyl]-5-pyridyl]-N,N'-dimethyl-1,3-propanediamine was obtained as a pale brown oil (75.0 mg, yield: 23%) from N,N'-bis(2-trifluoromethanesulfonyloxy-5-pyridyl)-N,N'-dimethyl-1,3-propanediamine (220.0 mg, 0.400 mmol) synthesized by a similar procedure to that described in Reference Example 1 and 4-(4-methoxybenzyloxy)-3,5-dimethoxyphenylboronic acid (308.0 mg, 0.970 mmol) synthesized by a similar procedure to that described in Reference Example 3.

To a solution of N,N'-bis[2-[4-(4-methoxybenzyloxy)-3,5-dimethoxyphenyl]-5-pyridyl]-N,N'-dimethyl-1,3-propanediamine (72.0 mg, 0.089 mmol) in methylene chlo-

EXAMPLE 55

N,N'-Bis[2-(3-methoxy-4,5-ethylenedioxyphenyl)-5-pyridyl]-N,N'-dimethyl-1,3-propanediamine dimethanesulfonate

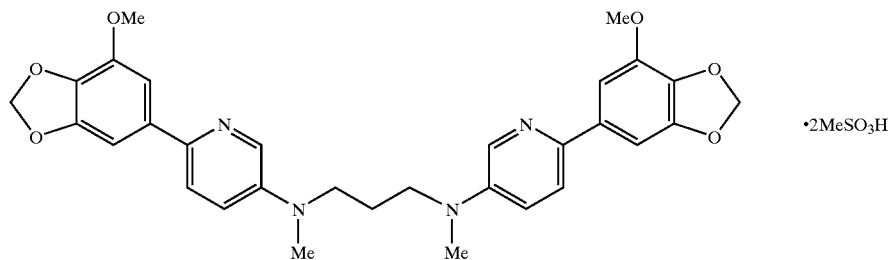

Following the procedure of Example 1, N,N'-bis[2-(3-methoxy-4,5-methylenedioxyphenyl)-5-pyridyl]-N,N'-dimethyl-1,3-propanediamine was obtained as a colorless oil (46.0 mg, yield: 52%) from N,N'-dimethyl-N,N'-bis(2-trifluoromethanesulfonyloxy-5-pyridyl)-1,3-propanediamine (78.0 mg, 0.160 mmol) synthesized by a similar procedure to that described in Reference Example 1 and 3-methoxy-4,5-methylenedioxyphenylboronic acid (66.0 mg, 0.340 mmol).

To a solution of N,N'-bis[2-(3-methoxy-4,5-methylenedioxyphenyl)-5-pyridyl]-N,N'-dimethyl-1,3-propanediamine (46.0 mg, 0.080 mmol) in methanol (2.0 mL) was added a 1.0 M aqueous methanesulfonic acid solution (0.20 mL, 0.20 mmol), and the reaction mixture was concentrated under reduced pressure. Ethanol (5.0 mL) was added to the residue, and the mixture was concentrated under reduced pressure. Diethyl ether was added to a solution of the residue in methanol and the resulting precipitate was collected by filtration to yield the title compound as a yellow amorphous powder (29.0 mg, yield: 46%).

$^1$H-NMR [CD$_3$OD-CDCl$_3$(1:10)](ammonium salt NH$^+$ protons were not observed) δ: 2.04(tt, J=7.3, 7.3 Hz, 2H), 2.86(s, 6H), 3.17(s, 6H), 3.58(t, J=7.3 Hz, 4H), 3.99(s, 6H), 6.08(s, 4H), 6.87(d, J=1.7 Hz, 2H), 6.97(d, J=1.7 Hz, 2H), 7.78(dd, J=3.2, 9.5 Hz, 2H), 7.88(d, J=9.5 Hz, 2H), 8.38(d, J=3.2 Hz, 2H).

EXAMPLE 56

N,N'-Diethyl-N,N'-bis[2-(4-isopropoxy-3,5-dimethoxyphenyl)-5-pyridyl]-1,3-propanediamine dimethanesulfonate

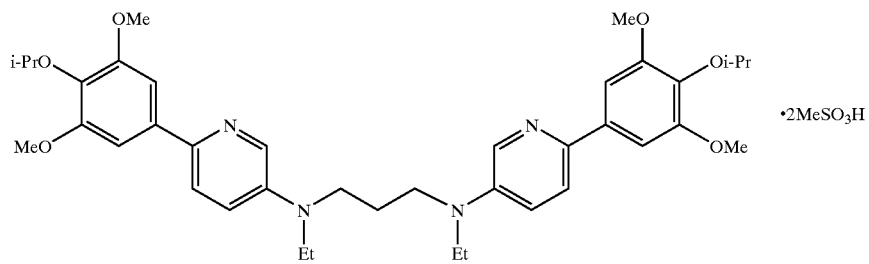

Following the procedure of Example 1, N,N'-diethyl-N,N'-bis[2-(4-isopropoxy-3,5-dimethoxyphenyl)-5-pyridyl]-1,3-propanediamine was obtained as a pale yellow oil (78.0 mg, yield: 58%) from N,N'-diethyl-N,N'-bis(2-trifluoromethanesulfonyloxy-5-pyridyl)-1,3-propanediamine (116.0 mg, 0.200 mmol) synthesized by a similar procedure to that described in Reference Example 1 and 4-isopropoxy-3,5-dimethoxyphenylboronic acid (96.0 mg, 0.400 mmol).

To a solution of N,N'-diethyl-N,N'-bis[2-(4-isopropoxy-3,5-dimethoxyphenyl)-5-pyridyl]-1,3-propanediamine (78.0 mg, 0.110 mmol) in methanol-chloroform (2:1, 3.0 mL) was added a 1.0 M aqueous methanesulfonic acid (0.24 mL, 0.24 mmol), and the reaction mixture was concentrated under reduced pressure. Ethanol (5.0 mL) was added to the residue, and the mixture was concentrated under reduced pressure. The residue was recrystallized from methanol-diethyl ether-hexane to yield the title compound as yellow flakes (melting point: 173.0–175.0° C.) (66.0 mg, yield: 66%).

$^1$H-NMR (DMSO-d$_6$, 120° C. )(ammonium salt NH$^+$ protons were not observed) δ: 1.18(t, J=7.0 Hz, 6H), 1.23(d, J=6.0 Hz, 12H), 1.93(tt, J=7.0, 7.0 Hz, 2H), 2.42(s, 6H), 3.47–3.56(m, 4H), 3.50(q, J=7.0 Hz, 4H), 3.85(s, 12H), 4.38(qq, J=6.0, 6.0 Hz, 2H), 7.15(s, 4H), 7.56(dd, J=3.1, 9.0 Hz, 2H), 7.90(d, J=9.0 Hz, 2H), 8.09(d, J=3.1 Hz, 2H).

EXAMPLE 57

N,N-Bis[N-[2-(3,5-dimethoxy-4-(2,2,2-trifluoroethoxy)phenyl]-5-pyridyl]-N-methyl-3-aminopropyl]methylamine trihydrochloride

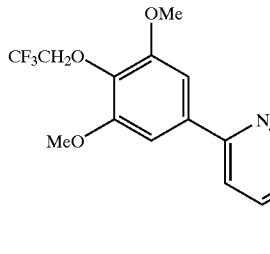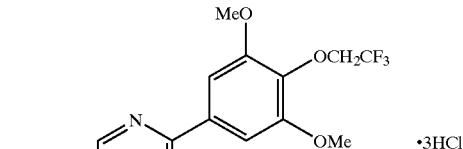

To a solution of 5-amino-2-[3,5-dimethoxy-4-(2,2,2-trifluoroethoxy)phenyl]pyridine (melting point: 176.0–177.5° C.)(28.2 g, 85.4 mmol) synthesized by a similar procedure to that described in Reference Example 11 in methylene chloride (550 mL) was added N,N-diisopropylethylamine (18.0 mL, 103 mmol). To the ice-cold stirred solution was added acryloyl chloride (7.00 mL, 86.0 mmol) dropwise over about 10 minutes. A saturated aqueous sodium hydrogencarbonate was added, and the resulting mixture was extracted with chloroform. The organic layer was dried over anhydrous sodium sulfate and concentrated under reduced pressure. Chloroform-hexane (1:2, 300 mL) was added to the residue and the resulting precipitate was collected by filtration to yield crude 5-acryloylamino-2-[3,5-dimethoxy-4-(2,2,2-trifluoroethoxy)phenyl]pyridine was obtained as colorless needles (melting point: 207.0–209.0° C.)(38.2 g).

To a 30% solution of methylamine in ethanol (100 mL, 970 mmol) was added the crude 5-acryloylamino-2-[3,5-dimethoxy-4-(2,2,2-trifluoroethoxy)phenyl]pyridine (19.2 g, approx. 50.2 mmol) obtained by the above-described procedure. After being stirred at room temperature for 1 hour, the reaction mixture was concentrated under reduced pressure. Chloroform (100 mL) was added to the residue, and the mixture was again concentrated under reduced pressure. To a solution of the residue in chloroform (100 mL) was added the crude 5-acryloylamino-2-[3,5-dimethoxy-4-(2,2,2-trifluoroethoxy)phenyl]pyridine (16.0 g, approx. 41.8 mmol) obtained by the above-described procedure, and the mixture was stirred at 60° C. for 12 hours. The solidified reaction mixture was dissolved in chloroform (600 mL), and the resulting solution was heated at 80° C. for 2 hours, then the solvent was removed by distillation. The residue was again dissolved in chloroform (600 mL) and the solution was concentrated to about 200 mL. Hexane (100 mL) was added to the solution stirred at 80° C. After cooling, the precipitated crystals were collected by filtration to yield N,N-bis[2-[N-[2-[3,5-dimethoxy-4-(2,2,2-trifluoroethoxy)phenyl]-5-pyridyl]carbamoyl]ethyl]methylamine as a colorless crystalline powder [melting point: 99.0° C.(decomposed)] [22.67 g, yield: 72% based on 5-amino-2-[3,5-dimethoxy-4-(2,2,2-trifluoroethoxy)phenyl]pyridine].

Under nitrogen, lithium aluminum hydride (4.28 g, 113 mmol) was added to an ice-cold solution of N,N-bis[2-[N-[2-[3,5-dimethoxy-4-(2,2,2-trifluoroethoxy)phenyl]-5-pyridyl]carbamoyl]ethyl]methylamine (22.50 g, 28.3 mmol) in anhydrous tetrahydrofuran (500 mL). The ice bath was removed, and the reaction mixture was stirred at 65° C. for 1 hour. Methanol (20 mL, 490 mmol) was added to the ice-cold reaction mixture, and the ice bath was removed. Water (20 mL), diethyl ether (2 L), and anhydrous magnesium sulfate (130 g) were added, and the mixture was stirred overnight at room temperature. Insoluble materials were removed by filtration through Celite, and the filtrate was concentrated under reduced pressure. The residue was purified by column chromatography on silica gel to provide N,N-bis[N-[2-[3,5-dimethoxy-4-(2,2,2-trifluoroethoxy)phenyl]-5-pyridyl]-3'-aminopropyl]methylamine as a colorless oil (20.32 mg, yield: 94%).

To a solution of N,N-bis[N-[2-[3,5-dimethoxy-4-(2,2,2-trifluoroethoxy)phenyl]-5-pyridyl]-3-aminopropyl]methylamine (2.11 g, 2.75 mmol) in acetonitrile (10 mL) were added formalin (2.1 mL, 28 mmol) and sodium cyanoborohydride (0.55 g, 8.8 mmol). To the mixture was added to a solution of acetic acid (0.3 mL) in acetonitrile (1 mL) dropwise over about 10 minutes, and the resulting mixture was stirred at room temperature for 1 hour. To the reaction mixture were added formalin (2.1 mL, 28 mmol) and sodium cyanoborohydride (0.65 g, 10 mmol), then was added a solution of acetic acid (0.6 mL) in acetonitrile (0.5 mL) dropwise over about 10 minutes. After stirring at room temperature for 1 hour, 1.0 M aqueous sodium hydroxide solution (100 mL) was added to the reaction mixture, and the mixture was extracted with methylene chloride. The organic layer was concentrated under reduced pressure, and a solution of the residue in pyridine (15 mL) was stirred at 45° C. for 1 hour, and then concentrated under reduced pressure. Toluene was added to the residue, and the mixture was concentrated under reduced pressure. The residue was purified by column chromatography on silica gel to yield N,N-bis[N-[2-[3,5-dimethoxy-4-(2,2,2-trifluoroethoxy)phenyl]-5-pyridyl]-N-methyl-3-aminopropyl]methylamine was obtained as a colorless oil (984 mg, yield: 45%).

To a solution of N,N-bis[N-[2-[3,5-dimethoxy-4-(2,2,2-trifluoroethoxy)phenyl]-5-pyridyl]-N-methyl-3-aminopropyl]methylamine (3.62 g, 4.55 mmol) in ethanol (50 mL) was added concentrated hydrochloric acid (1.4 mL, 17 mmol), and the reaction mixture was concentrated under reduced pressure. Ethanol (50 mL) was added to the residue, and the mixture was concentrated under reduced pressure.

Ethyl acetate (20 mL) was added to the residue, followed by concentration of the resultant mixture under reduced pressure. The residue was suspended in ethyl acetate and collected by filtration to yield the title compound as a yellow crystalline powder [melting point: 140.0° C. (decomposed)] (3.55 g, yield: 86%).

$^1$H-NMR (CD$_3$OD)(ammonium salt NH$^+$ protons were not observed) δ: 2.17(br dddd, J=7.3, 7.3, 7.3, 7.3 Hz, 4H), 2.94(s, 3H), 3.20(s, 6H), 3.23–3.32(m, 2H), 3.34–3.44(m, 2H), 3.65(dt, J=14.3, 7.3 Hz, 2H), 3.70(dt, J=14.3, 7.3 Hz, 2H), 3.97(s, 12H), 4 45(q, $^3J_{HF}$=8.8 Hz, 4H), 7.15(s, 4H), 8.00(br dd, J=3.0, 9.5 Hz, 2H), 8.12(br d, J=3.0 Hz, 2H), 8.14(br d, J=9.5 Hz, 2H).

EXAMPLE 58

N,N-Bis[N-[2-(3,5-dimethoxy-4-methylthiophenyl-5-pyridyl]-N-methyl-3-aminopropyl]methylamine trihydrochloride

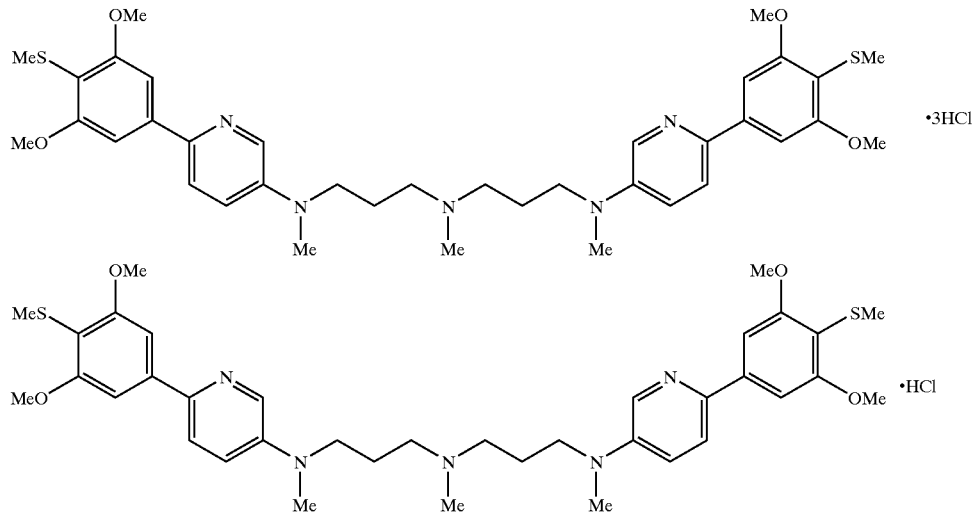

Synthesis followed the procedure of Example 57. From 5-amino-2-(3,5-dimethoxy-4-methylthiophenyl)pyridine (182.0 mg, 0.660 mmol) synthesized by a similar procedure to that described in Reference Example 11, N,N-bis[2-[N-[2-(3,5-dimethoxy-4-methylthiophenyl)-5-pyridyl]carbamoyl]ethyl]methylamine was obtained as a colorless viscous oil [136.0 mg, yield: 61% based on 5-amino-2-(3,5-dimethoxy-4-methylthiophenyl)pyridine]. From N,N-bis[2-[N-[2-(3,5-dimethoxy-4-methylthiophenyl)-5-pyridyl]carbamoyl]ethyl]methylamine (671.0 mg, 0.970 mmol), N,N-bis[N-[2-(3,5-dimethoxy-4-methylthiophenyl)-5-pyridyl]-3-aminopropyl]methylamine was obtained as a colorless oil (508.0 mg, yield: 79%). From N,N-bis[N-[2-(3,5-dimethoxy-4-methylthiophenyl)-5-pyridyl]-3-aminopropyl]methylamine (67.0 mg, 0.100 mmol), N,N-bis[N-[2-(3,5-dimethoxy-4-methylthiophenyl)-5-pyridyl]-N-methyl-3-aminopropyl]methylamine was obtained as a colorless oil (44.0 mg, yield: 64%). From N,N-bis[N-[2-(3,5-dimethoxy-4-methylthiophenyl)-5-pyridyl]-N-methyl-3-aminopropyl]methyl-amine (67.0 mg, 0.100 mmol), the title compound was obtained as a yellow amorphous powder (42.0 mg, yield: 52%).

$^1$H-NMR (CDCl$_3$)(data for the free base of the title compound) δ: 1.74–1.85(m, 4H), 2.23(s, 3H), 2.35–2.44(m, 4H), 2.39(s, 6H), 3.01(s, 6H), 3.45(t, J=7.3 Hz, 4H), 3.98(s, 12H), 7.04(dd, J=2.9, 8.8 Hz, 2H), 7.15(s, 4H), 7.59(d, J=8.8 Hz, 2H), 8.22(d,J=2.9 Hz, 2H).

Test 1 (Evaluation of IgE Antibody Production Inhibiting Activity)

From a mouse (Balb/C, male, 8 weeks old), the spleen was enucleated. The spleen was shredded in 10% FBS/RPMI 1640, and was then disintegrated into single cells through a 70-mesh screen. Those single cells were hemolyzed with Gey's solution, and using RPMI 1640 medium/25 mM HEPES/0.3% BSA, a spleen cell suspension (1×10$^7$ cells/mL) was prepared. After an aliquot of the suspension was reacted with a rat anti-mouse Thy-1.2 monoclonal antibody (product of Cedarlane Laboratories Limited) at 4° C. for 1 hour, centrifugation was conducted. Precipitated cells were suspended again (1×10$^7$ cells/mL, RPMI/HEPES/BSA). After the suspension was next reacted with a low-cytotoxic rabbit complement (product of Cedarlane Laboratories Limited) at 37° C. for 1 hour, dead cells were removed by specific gravity centrifugation using Lympholyte M (product of Cedarlane Laboratories Limited) so that a B cell fraction was obtained as viable cells.

Using a 96-well plate, the B cells (2×10$^5$ cells/0.2 mL/well) were incubated together with LPS (*E. coli* 026:B6, product of DIFCO Laboratories, Inc.) for 1 day. Mouse IL-4 (product of Genzyme Corp.) was then added, followed by further incubation for 6 days.

The IgE antibody production inhibiting activity of each drug was calculated by adding the drug Day 1 of the incubation and assaying the quantity of IgE in the culture supernatant by ELISA after the incubation. Inhibition activity (IC$_{50}$) is presented in Table 1.

Further, the solubility (%) of each compound in water was also estimated. The results are presented in Table 1.

TABLE 1

| Compound (Example No.) | IC$_{50}$($\mu$M) | Solubility (%) |
| --- | --- | --- |
| 7 | 0.04 | 5 |
| 14 | 0.04 | 0.1 |
| 30 | 0.10 | 0.1 |
| 36 | 0.03 | 10 |
| 37 | 0.10 | 10 |
| 39 | 0.08 | 10 |
| 41 | 0.05 | 0.1* |
| 42 | 0.10 | 10 |
| 43 | 0.10 | 10* |
| 44 | 0.10 | 10 |
| 47 | 0.05 | 0.1 |
| 49 | 0.04 | 10 |
| 57 | 0.10 | 1 |

*Solubility in 1M hydrochloric acid

INDUSTRIAL APPLICABILITY

The bis(2-aryl-5-pyridyl) derivatives (1) of the present invention and salts thereof have excellent IgE antibody production inhibiting activity and are useful as medicinal agents for the prevention or treatment of allergic immune diseases.

Obviously, numerous modifications and variations of the present invention are possible in light of the above teachings. It is therefore to be understood that within the scope of the appended claims, the invention may be practiced otherwise than as specifically described herein.

What is claimed as new and is intended to be secured by Letters Patent is:

1. A bis(2-aryl-5-pyridyl) compound having formula (1) or a salt thereof:

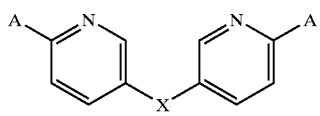

(1)

wherein A is a substituted or unsubstituted aromatic hydrocarbon group, and X is formula (4):

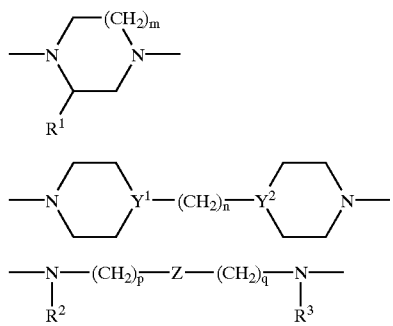

wherein, in formula (4), R$^2$ and R$^3$ each is a hydrogen atom or a lower alkyl group, Z represents a single bond, a substituted methylene group, a substituted imino group, an oxygen atom or a cycloalkylene group, and p and q each is 0 or an integer of 1 to 6.

2. A bis(2-aryl-5-pyridyl) compound or a salt thereof according to claim 1, wherein in the formula (1), A is a substituted or unsubstituted phenyl group.

3. The bis(2-aryl-5-pyridyl) compound or a salt thereof according to claim 1, wherein said aromatic hydrocarbon substituent is substituted by 1 to 3 substituents selected from the group consisting of lower alkyl groups, lower alkoxy groups, halogeno(lower alkyl) groups, lower alkoxy(lower alkyl) groups, hydroxy(lower alkyl) groups, carboxyl group, (lower alkoxy)carbonyl groups, unsubstituted or (lower alkyl)- and/or (lower alkoxy)-substituted carbamoyl groups, lower alkanoyl groups, formyl group, lower alkanoyloxy groups, halogen atoms, hydroxyl group, cyano, (lower alkyl) thio groups, amino group, mono- or di-(lower alkyl)amino groups, (low alkyl)sulfonylamino groups, pyrrolidinyl groups, and alkylenedioxy groups.

4. The bis(2-aryl-5-pyridyl) compound or a salt thereof according to claim 3, wherein the lower alkyl moiety in the lower alkyl group containing groups is methyl, ethyl, n-propyl, isopropyl, n-butyl, isobutyl, sec-butyl, tert-butyl, pentyl, hexyl, cyclopropyl or cyclohexyl.

5. The bis(2-aryl-5-pyridyl) compound or a salt thereof according to claim 1, wherein said aromatic hydrocarbon group (A) is phenyl or naphthyl.

6. The bis(2-aryl-5-pyridyl) compound or a salt thereof according to claim 1, wherein said aromatic hydrocarbon group is substituted with 1 to 3 substituents and wherein said 1 to 3 substituents are selected from the group consisting of methyl, methoxy, ethoxy, n-propoxy, isopropoxy, trifluoroethoxy, methoxyethoxy, hydroxyethoxy, hydroxy, cyano, methylthio, dimethylamino, pyrrolidinyl, carboxyl, ethoxycarbonyl, t-butoxycarbonyl, butyryloxy, N-methyl-N-methoxycarbomoyl, acetyl, and methylenedioxy.

7. The salt of the bis(2-aryl-5-pyridyl) compound according to claim 1, which is N,N'-bis[2-(3,4,5-trimethoxyphenyl)-5-pyridyl]-N,N'-dimethylethylenediamine dimethanesulfonate, N,N'-bis[2-(4-hydroxy-3,5-dimethoxyphenyl)-5-pyridyl]-N,N'-dimethylethylenediamine dimethanesulfonate, N,N-bis[2-(3,4,5-trimethoxyphenyl)-5-pyridyl]-N,N'-dimethyl-1,3-propanediamine dimethanesulfonate, N,N'-bis[2-(3,4,5-trimethoxyphenyl)-5-pyridyl]N,N',2,2-tetramethyl-1,3-propanediamine dimethanesulfonate, 2-hydroxy-N,N-bis[2-(3,4,5-trimethoxyphenyl)-5-pyridyl]-N,N'-dimethyl]-1,3-propanediamine, N,N-bis[N-[2-(3,4,5-trimethoxyphenyl)-5-pyridyl]-N-methyl-2-aminoethyl]methylamine trihydrochloride, N,N'-bis[N-[2-(3,4,5-trimethoxyphenyl)-5-pyridyl]-N-methyl-3-aminopropyl]methylamine, bis[N-[2-(3,4,5-trimethoxyphenyl)-5-pyridyl]-2-aminoethyl]ether dimethanesulfonate, N,N'-bis[2-(3,4,5-trimethoxyphenyl)-5-pyridyl]-N,N'-dimethyl-1,6-hexanediamine dimethanesulfonate, or N,N-bis[N-[2-[3,5-dimethoxy-4-(2,2,2-trifluoroethoxy)phenyl]-5-pyridyl]-N-methyl-3-aminopropyl]methylamine trihydrochloride.

8. A pharmaceutical composition comprising, as an active ingredient, an effective amount of a bis(2-aryl-5-pyridyl) compound or a salt thereof according to claim 1.

9. A method of treating, allergic immune disease in a subject, comprising administering the pharmaceutical composition according to claim 8 to a subject.

10. The method according to claim 9, wherein said allergic immune disease is at least one member selected from the group consisting of asthma, atopic dermatitis, allergic rhinitis, inflammatory bowel disease, contact dermatitis and an allergic opthalmopathy.

11. A method of inhibiting the production of IgE antibody in a subject comprising, administering the bis(2-aryl-5-pyridyl) compound of a salt thereof according to claim 1 to a subject.

12. A pharmaceutical composition, comprising: a bis(2-aryl-5-pyridyl) compound or a salt thereof according to claim 1 and a pharmacologically acceptable carrier.

13. A method of treating a subject suffering from an allergic immune disease, which comprises:

administering an effective amount of a bis(2-aryl-5-pyridyl) compound or a salt thereof according to claim 1 to said subject.

14. The method according to claim 13, wherein said allergic immune disease is at least one member selected from the group consisting of asthma, atopic dermatitis, allergic rhinitis, inflammatory bowel disease, contact dermatitis and an allergic opthalmopathy.

15. A method of treating the symptoms of allergic immune disease in a subject, comprising administering an effective amount of a bis(2-aryl-5-pyridyl) compound or a salt thereof according to claim 1 to said subject.

16. The method according to claim 15, wherein said allergic immune disease is at least one member selected from the up consisting of asthma, atopic dermatitis, allergic rhinitis, inflammatory bowel disease, contact dermatitis and an allergic opthalmopathy.

17. A method of treating the symptoms of allergic immune disease in a subject, comprising administering the pharmaceutical composition according to claim 8 to said subject.

18. The method according to claim 17, wherein said allergic immune disease is at least one member selected from the group consisting of asthma, atopic dermatitis, allergic rhinitis, inflammatory bowel disease, contact dermatitis and an allergic opthalmopathy.

19. A method of treating the symptoms of allergic immune disease in a subject, comprising administering the pharmaceutical composition according to claim 12 to said subject.

* * * * *

UNITED STATES PATENT AND TRADEMARK OFFICE
CERTIFICATE OF CORRECTION

PATENT NO. : 6,890,940 B2
DATED : May 10, 2005
INVENTOR(S) : Hiroyuki Ishiwata et al.

It is certified that error appears in the above-identified patent and that said Letters Patent is hereby corrected as shown below:

Column 79,
Lines 45-54, "wherein A is a substituted or unsubstituted aromatic hydrocarbon group, and X is formula (4):

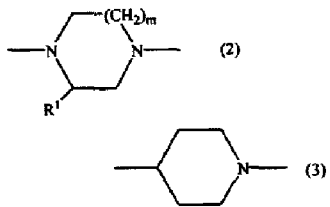

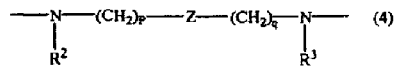

" should read
-- wherein A is a substituted or unsubstituted aromatic hydrocarbon group, and X is formula (4):

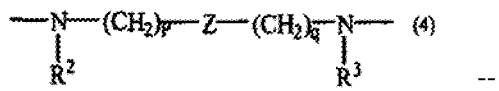

--

Signed and Sealed this

Twenty-sixth Day of July, 2005

JON W. DUDAS
*Director of the United States Patent and Trademark Office*